United States Patent
Yvin et al.

(10) Patent No.: US 8,367,641 B2
(45) Date of Patent: Feb. 5, 2013

(54) USE OF MODIFIED OLIGO-β-(1,3)-GLUCANS FOR TREATING DISEASES OF THE IMMUNE SYSTEM, OLIGO-β-(1,3)-GLUCAN-(1,3)-MANNOSE, OLIGO-β-(1,3)-GLUCAN-(1,3)-MANNITOL AND DERIVATIVES THEREOF, METHODS FOR PREPARING THEM AND MEDICAMENTS CONTAINING THEM

(75) Inventors: Jean-Claude Yvin, Saint Malo (FR); Karine Descroix, Saint-Colomban (FR); Vincent Ferrieres, Gahard (FR); Frank Jamois, La Chapelle des Fouegeretz (FR); Isabelle Laurent, Rennes (FR); Vaclav Vetvika, Louisville, KY (US)

(73) Assignee: ASE & BIO, Paris (FR)

( * ) Notice: Subject to any disclaimer, the term of this patent is extended or adjusted under 35 U.S.C. 154(b) by 479 days.

(21) Appl. No.: 12/520,612

(22) PCT Filed: Dec. 20, 2007

(86) PCT No.: PCT/FR2007/052595
§ 371 (c)(1),
(2), (4) Date: Mar. 12, 2010

(87) PCT Pub. No.: WO2008/087340
PCT Pub. Date: Jul. 24, 2008

(65) Prior Publication Data
US 2010/0286388 A1     Nov. 11, 2010

(30) Foreign Application Priority Data
Dec. 22, 2006  (FR) ..................................... 06 11333

(51) Int. Cl.
*A61K 31/702* (2006.01)
*A61K 31/716* (2006.01)
*C07H 3/06* (2006.01)

(52) U.S. Cl. ................ 514/61; 536/123.12; 536/123.13; 536/125

(58) Field of Classification Search ........................ None
See application file for complete search history.

(56) References Cited

U.S. PATENT DOCUMENTS

| | | | |
|---|---|---|---|
| 5,980,916 A * | 11/1999 | Yvin et al. | ............... 536/123.12 |
| 6,660,722 B2 | 12/2003 | Yvin et al. | |
| 2,804,684 A1 | 10/2005 | Yvin et al. | |
| 7,070,778 B2 | 7/2006 | Yvin et al. | |

FOREIGN PATENT DOCUMENTS

| | | |
|---|---|---|
| EP | 0 089 940 | 9/1983 |
| JP | 59 036691 | 2/1984 |

OTHER PUBLICATIONS

Annan, W. et al "The constitution of laminarin . . . " J. Chem. Soc. (1965) pp. 220-226.*
Goldstein et al, "Carbohydrate binding properties of banana (*Musa acuminate*) lectin II. Binding of laminaribiose oligosaccharides and β-glucans containing β 1,6-glucosyl end groups", 2001, pp. 2616-2619, 268, Eur. J. Biochem.

* cited by examiner

*Primary Examiner* — Leigh Maier
(74) *Attorney, Agent, or Firm* — B. Aaron Schulman, Esq.; Stites & Harbison PLLC

(57) ABSTRACT

The present invention relates to the use of at least one compound of formula (I) or (II), in which $R_1$ is H and n is an integer from 2 to 10, for the preparation of a medicament for treating diseases chosen from the group comprising tumour, cancer, viral disease, bacterial disease, fungal disease, disease of the immune system, auto-immune disease or disease linked to a deficiency in immunostimulation, in human beings and warm-blooded animals. The invention also relates to new products having a mannose or mannitol termination as well as a method for preparing them.

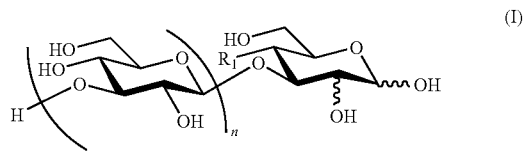

(I)

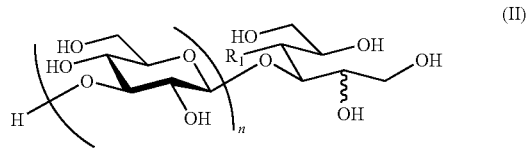

(II)

16 Claims, No Drawings

USE OF MODIFIED OLIGO-β-(1,3)-GLUCANS FOR TREATING DISEASES OF THE IMMUNE SYSTEM, OLIGO-β-(1,3)-GLUCAN-(1,3)-MANNOSE, OLIGO-β-(1,3)-GLUCAN-(1,3)-MANNITOL AND DERIVATIVES THEREOF, METHODS FOR PREPARING THEM AND MEDICAMENTS CONTAINING THEM

The present invention relates to the use of modified oligo-β-(1,3)-glucans of formula (I) or (II) below for the preparation of medicaments which are useful in treatments based on the stimulation of the immune system.

The glucans, which are natural products, have long been studied and the immunostimulant properties of certain glucans are known. However, not all the natural glucans are active.

The applicant company has shown, in particular in WO03/045414 that Laminarine, which is a polysaccharide extracted from the brown alga *Laminaria digitata* has immunostimulation activities. Laminarine is a polysaccharide with a low molecular weight constituted by a main linear β-(1,3)-glucan chain, of 20 to 30 glucose units weakly branched in position 6, which has at the terminal end either a glucose entity (G chain) or a mannitol entity (M chain).

Although the immunostimulant activity of Laminarine has been recognized, a major drawback of its use for therapeutic purposes is its natural origin. In fact, the composition of Laminarine is not constant and depends in particular on where and when it is collected, etc.

A real need therefore exists for synthetic products having the therapeutic properties of Laminarine.

The present inventors have turned more particularly to the M group oligosaccharides present in Laminarine. In the literature, it is mentioned that these oligosaccharides have a bond of β configuration between carbon number 1 of the terminal entity of the glucan and a primary carbon of the mannitol residue, and can be represented as follows:

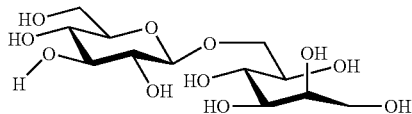

They have sought to synthesize these molecules in order to provide in particular the pharmaceutical industry with molecules the characterization of which is complete and the structure completely clarified, thus avoiding the difficulties inherent in the use of natural products as pharmaceutical products.

Unexpectedly and surprisingly, the present inventors found that the oligosaccharides of formula (I) or (II) below, which themselves have a β bond between carbon number 1 of the terminal glucose entity and a secondary carbon of the mannose or mannitol terminal entity, had immunostimulant activities.

A first subject of the invention therefore relates to the use of at least one modified oligo-β-(1,3)-glucan of formula (I) or (II)

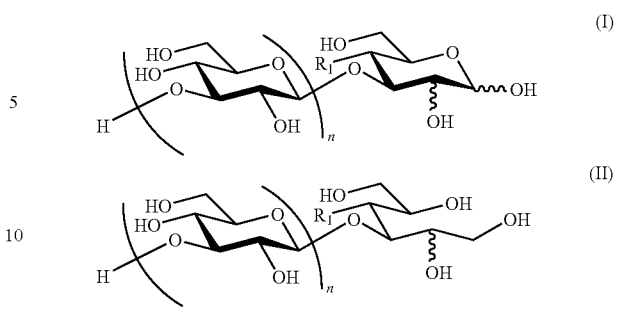

in which $R_1$ represents H or OH and n is an integer from 2 to 10, preferably from 2 to 7, and still more preferably equal to 3, 4 or 5, for the preparation of a composition intended for the treatment of diseases chosen from the group including tumour, cancer, viral disease, bacterial disease, fungal disease, disease of the immune system, auto-immune disease or disease linked to a deficiency in immunostimulation, in humans and warm-blooded animals. The action of the compounds of formula (I) or (II) is linked to the presence of receptors specific to these compounds at the surface of the macrophages and more generally of the different populations of leucocytes. This activity is attributed to the stimulation of immunocompetent cells of the organism and is measured via:

- the activation of the NK cells, T lymphocytes, and nuclear factor κB(NF-κB);
- the phagocytic activity;
- the secretion of cytokines such as the interleukins (IT), TNF-α, or also interferon γ;
- the production of reactive oxygen species such as the superoxide anion or hydrogen peroxide.

Advantageously, when in the compound of formula (II), $R_1$ represents OH, the terminal group is a mannitol.

The interaction mechanisms of numerous glucans have been broadly described, but have shown results which are often contradictory, making it impossible to predict which glucan is the best immunomodulator. As for the effects linked to functional or structural modifications, these are completely unpredictable.

According to the invention, the composition used according to the invention can be administered to the patient by intravenous, intraperitoneal or oral route.

The doses of compounds of formula (I'), (II') are a function of the pathology to be treated and the adopted administration method. They are generally from 25 to 70 IU/kg of bodyweight per day, more preferably from 35 to 45 FU/kg of bodyweight per day.

Useful medicaments which are administered by oral route are tablets, granules, syrup, gelatin capsules, gel.

According to another embodiment, the composition used according to the invention can also comprise a chemotherapeutic agent.

The chemotherapeutic agent is chosen from the group comprising cisplatin, vinblastine, paclitaxel, taxol and its derivatives, monoclonal antibodies such as in particular Rituximab and Cituximab.

When the composition comprises a chemotherapeutic agent and/or a potentiator, according to the invention, it can be used in a sequenced manner, i.e. the compound of formula (I) or (II) is administered at a certain point in time and the chemotherapeutic agent is administered at another point in time optionally with the potentiator.

The present invention also relates to certain derivatives of formula (I) and (II) above which are novel compounds. These novel compounds are oligo-β-(1,3)-glucan-(1,3)-mannose and oligo-β-(1,3)-glucan-(1,3)-mannitol and their deoxy derivatives in position 4, which have the general formula (I') or the general formula (II') respectively:

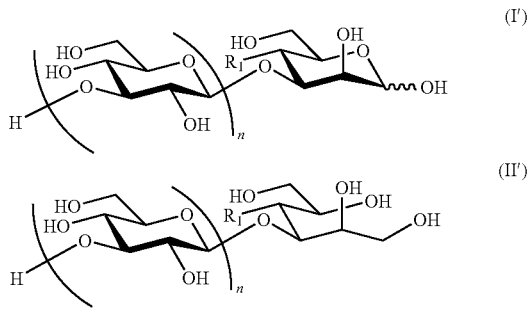

in which $R_1$ represents H or OH and n is an integer from 2 to 10, preferably from 2 to 7, and still more preferably equal to 3, 4 or 5.

More particularly, such compounds are the following compounds:

β-D-glucopyranosyl-(1→3)-β-D-glucopyranosyl-(1→3)-(α,β)-D-mannopyranose;

β-D-glucopyranosyl-(1→3)-β-D-glucopyranosyl-(1→3)-β-D-glucopyranosyl-(1→3)-β-D-glucopyranosyl-(1→3)-β-D-glucopyranosyl-(1→3)-β-D-mannopyranose;

β-D-glucopyranosyl-(1→3)-β-D-glucopyranosyl-(1→3)-4-deoxy-(α,β)-D-deoxy-mannopyranose;

β-D-glucopyranosyl-(1→3)—O-D-glucopyranosyl-(1→3)-mannitol;

β-D-glucopyranosyl-(1→3)-β-D-glucopyranosyl-(1→3)-4-deoxy-mannitol;

β-D-glucopyranosyl-(1→3)-β-D-glucopyranosyl-(1→3)—O-D-glucopyranosyl-(1→3)-β-D-glucopyranosyl-(1→3)—O-D-glucopyranosyl-(1→3)-mannitol;

β-D-glucopyranosyl-(1→3)-β-D-glucopyranosyl-(1→3)-β-D-glucopyranosyl-(1→3)-β-D-glucopyranosyl-(1→3)-β-D-glucopyranosyl-(1→3)-4-deoxy-(α,β)-D-mannopyranose;

β-D-glucopyranosyl-(1→3)-β-D-glucopyranosyl-(1→3)-(3-D-glucopyranosyl-(1→3)-β-D-glucopyranosyl-(1→3)-β-D-glucopyranosyl-(1→3)-4-deoxy-mannitol.

These novel compounds are useful as pharmaceutical compounds.

A subject of the invention is therefore also medicaments comprising these novel compounds with at least one excipient chosen as a function of the adopted administration method and dosage.

These medicaments can be medicaments intended for administration by oral route, by intravenous route or by intraperitoneal route.

The doses of compounds of formula (I'), (II') are a function of the pathology to be treated and of the adopted method of administration. They are generally from 25 to 70 IU/kg of bodyweight per day, more preferably from 35 to 45 IU/kg of bodyweight per day.

Useful medicaments administered by oral route are tablets, granules, syrup, gelatin capsules, gel.

These medicaments can also comprise at least one chemotherapeutic agent chosen from the group comprising cisplatin, vinblastine, paclitaxel, taxol and its derivatives, monoclonal antibodies such as in particular Rituximab and Cituximab.

In particular, these compounds are useful as immunomodulatory agents.

Another subject of the invention relates to the use of at least one compound of formula (I') or (II') for the treatment of a disease chosen from the group including tumour, cancer, viral disease, bacterial disease, fungal disease, disease of the immune system, auto-immune disease or disease linked to a deficiency in immunostimulation, in warm-blooded animals and human beings.

These compounds have an original structure since the glucanic part is linked to the mannitol residue by one of these secondary hydroxyls via a bond of configuration β. The presence of the molecules of formula (I') and (II') in which $R_1$ represents —OH has been detected in *Laminaria digita*. No preparation method has been described.

The preparation by chemical route of the novel compounds of formula (I') or (II') is based mainly on epimerization of the D-glucose type terminal reducing entity to D-mannose type residue. This involves the singularization of the reducing entity with respect to the other glucose units of the oligosaccharide and the singularization of the hydroxyl 2 of this entity with respect to the other functions of the reducing unit. Two different synthesis routes are envisaged, an iterative synthesis and a synthesis by epimerization of the terminal entity.

According to the first embodiment, the method for the preparation of the novel compounds comprises a reaction between a glycosyl donor of formula (D) below and a glycosyl acceptor of formula (A) below:

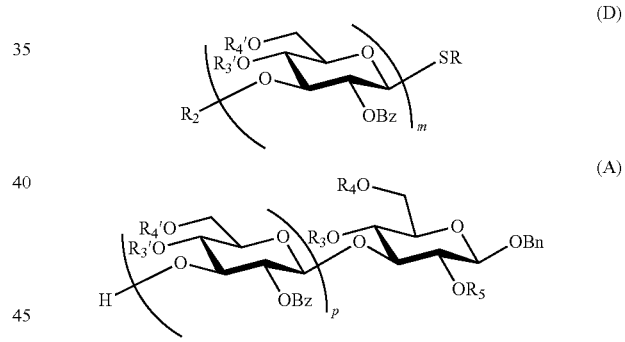

in which m is an integer from 1 to 9, preferably from 1 to 6, and still more preferably equal to 2, 3 or 4;

p is an integer from 0 to 9, preferably from 0 to 6, and still more preferably equal to 2, 3 or 4;

R represents alkyl such as ethyl, methyl, propyl or butyl, or aryl such as phenyl or tolyl;

$R_2$ represents allyl, methylnaphthyl, benzyl, paramethoxybenzyl, halogenoacetyl (chloroacetyl, bromoacetyl, iodoacetyl);

$R_3$ and $R_4$, on the one hand, and $R_3'$ and $R_4'$, on the other hand, together form an ethylidyl, isopropylidyl, hexafluoroisopropylidyl, cyclopentylidyl, cyclohexylidyl, cycloheptylidyl, butylidyl, 1-tertiobutylethylidyl, benzylidyl, methoxybenzylidyl, 1-phenylbenzylidyl radical or $R_3$, $R_4$, $R_3'$ and $R_4'$ each represent independently of each other a benzyl, chlorobenzyl, nitrobenzyl, allyl, triarylmethyl, trialkylsilyl such as triethylsilyl, tri-isopropylsilyl, tertiobutyldimethylsilyl, ester such as acetyl, chloroacetyl, benzoyl, pivaloyl;

$R_5$ represents H, a levulinoyl, acetyl, chloroacetyl, fluorenylmethyloxycarbonyl, trialkylsilyl group such as triethylsilyl, tri-isopropylsilyl, tertiobutyldimethylsilyl, preferably a levulinoyl group, provided that none of $R_3$, $R_4$, $R_3'$, $R_4'$ is identical to $R_5$.

In the present application the following abbreviations are used:

Bn: benzyl, NAP: 2-methylnaphthyl, Bz: benzoyl, X: halogen, SEt: Ethylthio-, Ac: acetyl, Lev: levulinoyl.

Advantageously, the compound of formula (A) is

Advantageously, the compound of formula (D) is

This stage of the method can be included in an iterative synthesis which differs from that described in FR2804684 by the necessary use of a first acceptor comprising in position 2 a protective group orthogonal to all the other groups present on the oligomers synthesized after elongation of the chain, which makes regioselective epimerization possible.

This iterative synthesis can be described according to the reaction diagram (reaction diagram 1) as given hereafter:

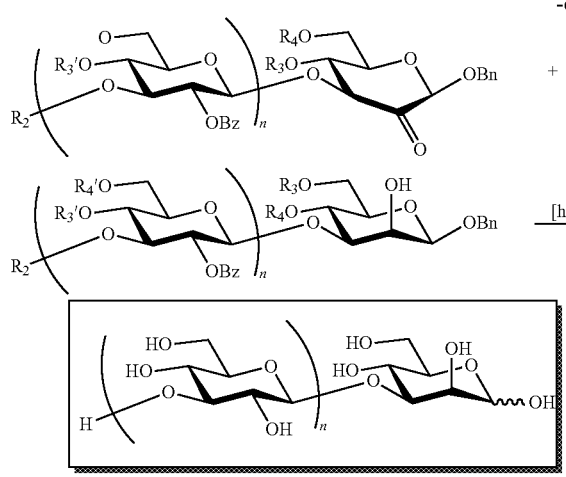
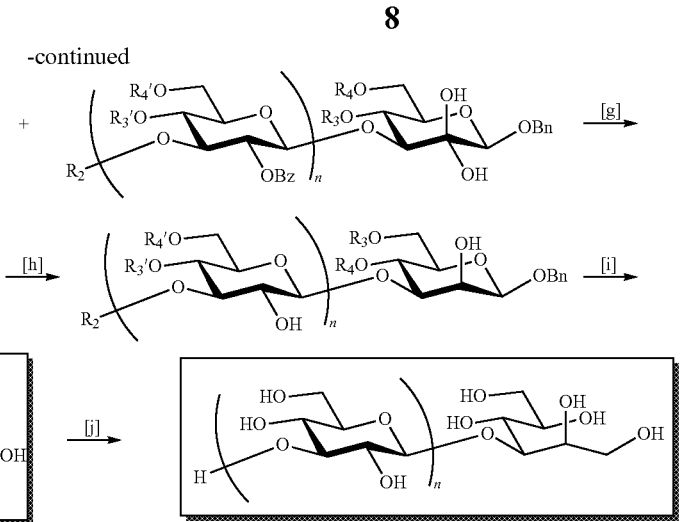

Reaction diagram 1 above comprises in the following order:
- the preparation [a'] from a compound 1 as obtained in FR2804694, of a compound 2 the —SEt group of which has been replaced by an —OBn group;
- the substitution [a] in position 2 of —OBz by —ORhd 5, $R_5$ preferably being levulinoyl, and the selective deprotection [b] of the hydroxyl in position 3;
- the reaction between the donor 1 and the acceptor 4 [c], or glycosylation;
- optionally the selective deprotection [d] in position 3 of the hydroxyl and the glycosylation between compound 1 and compound 6, these two stages being able to be reiterated until the desired number n of glucose units is obtained;
- selective cleavage [e] of the levulinoyl (Lev) group; advantageously this cleavage is carried out with $NH_2NH_2$ in AcOH.
- oxidation [f], preferably with Dess-Martin periodinane;
- epimerizing reduction [g]; advantageously with L-selectride;
- deprotection [h] of all the ester groups, advantageously with MeONa/MeOH;
- cleavage [i] of all the hydrogenolyzable groups, advantageously with $H_2$, $Pd(OAc)_2$;
- optionally reduction [j] of the mannose to corresponding mannitol, advantageously with $NaBH_4$ in MeOH.

It is also possible to envisage the synthesis by utilizing a more convergent reaction diagram, as defined hereafter (reaction diagram 2).

In this reaction diagram, the donor D is a disaccharide, or a higher oligosaccharide, which is reacted with an acceptor A which is also a disaccharide or which is a higher oligosaccharide: tri-, tetra-, penta-, as obtained as compound 6 according to reaction diagram 1.

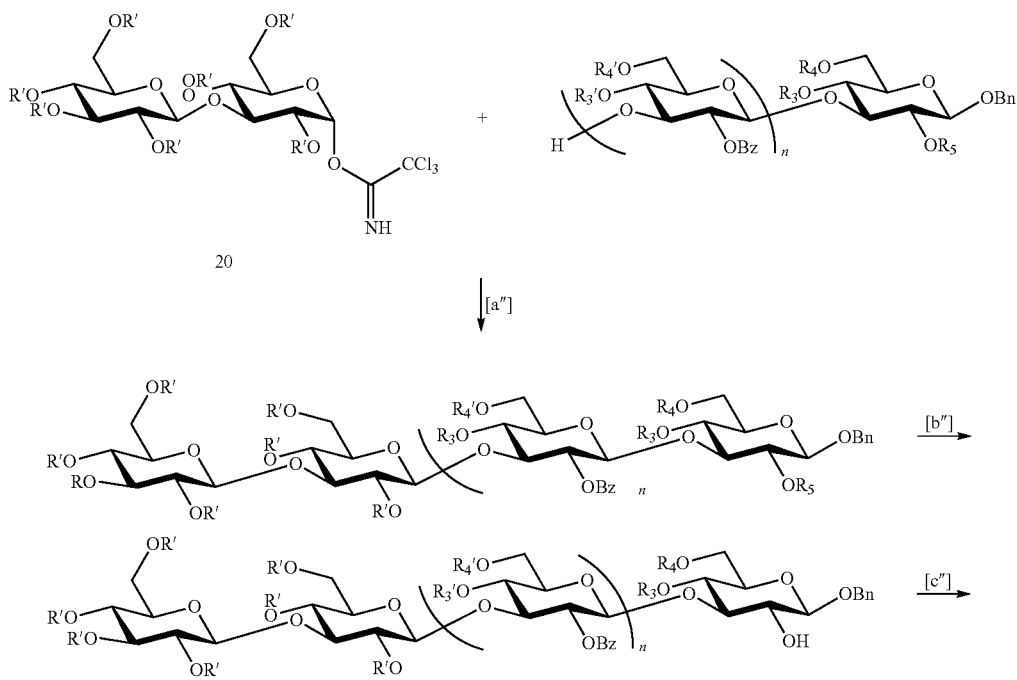

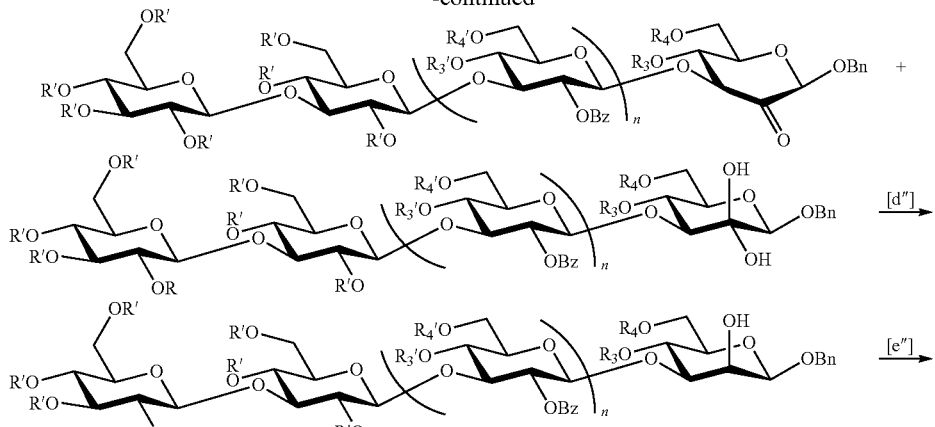

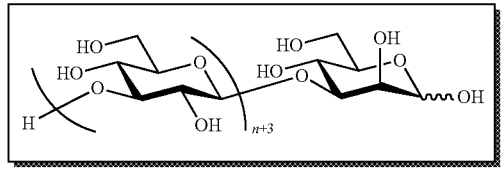

In this second reaction diagram, preferably R' is Ac, Bz or pivaloyl and $R_5$ is Lev.

This second reaction diagram comprises in the following order:

- the reaction [a"] between a glycosyl donor disaccharide (20) as obtained in FR2804694, and a glycosyl acceptor as prepared according to the first reaction diagram, advantageously in the presence of TMSOTf (trifluoromethanesulphonic acid);
- selective cleavage [b"] of the levulinoyl (Lev) group, advantageously with $NH_2NH_2$ in AcOH;
- Oxidation [c"], advantageously with Dess-Martin peridionane;
- epimerizing reduction [d"], advantageously with L-selectride;
- complete deprotection [e"], advantageously by MeONa/MeOH, reaction followed by $H_2$, $Pd(OAc)_2$.

According to a second embodiment, the method for preparing the novel compounds comprises a stage of epimerization in position 2 of the terminal member. This synthesis route also makes it possible to obtain the deoxygenated compounds in position 4.

Reaction diagram 3 below illustrates this embodiment:

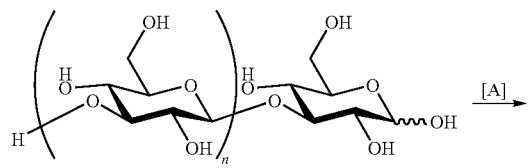

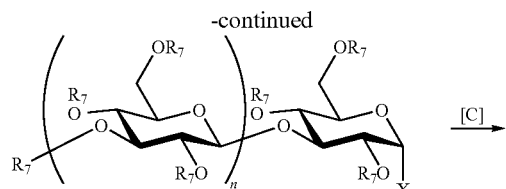

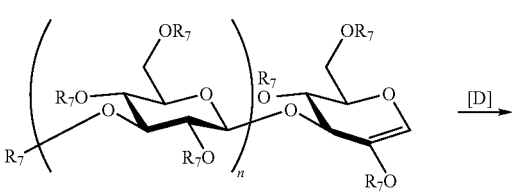

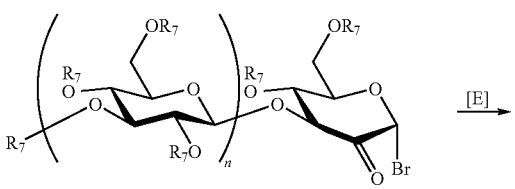

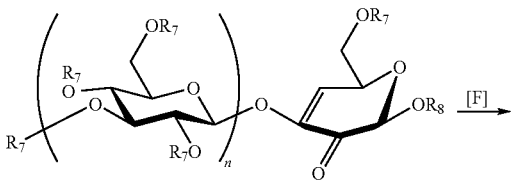

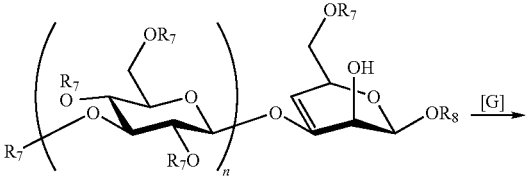

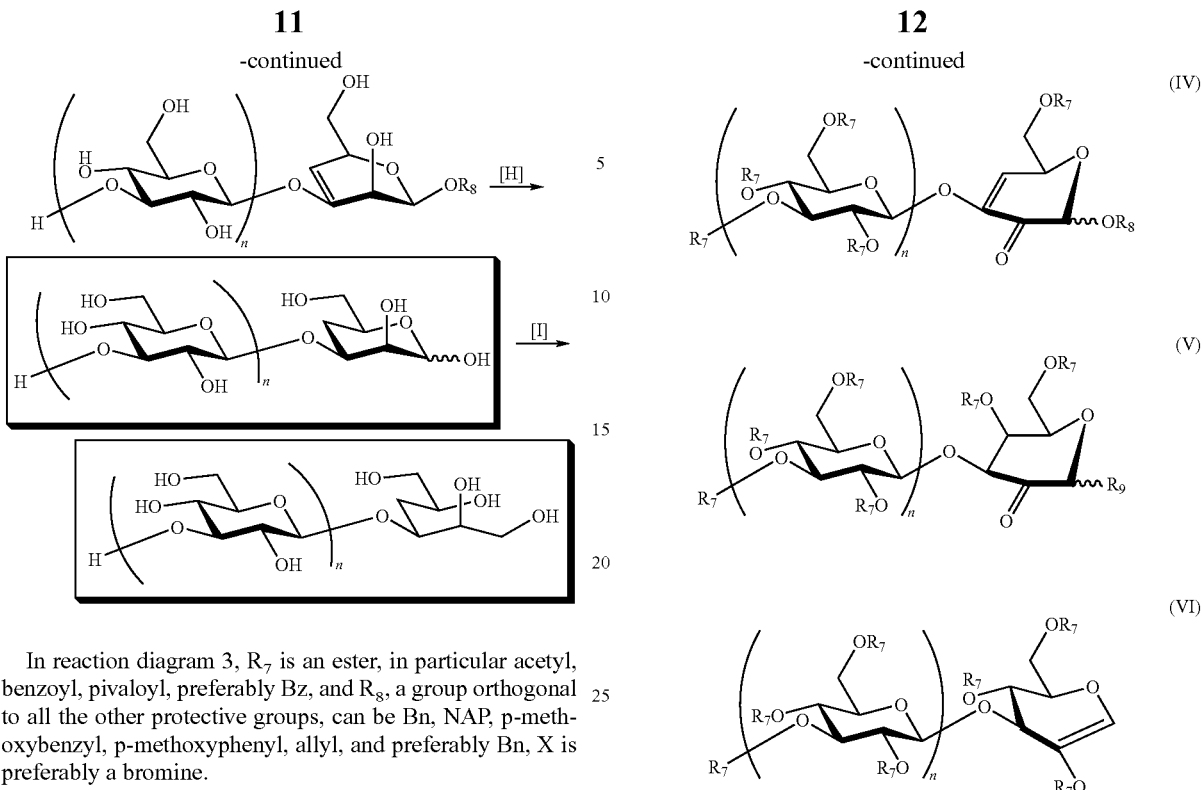

In reaction diagram 3, $R_7$ is an ester, in particular acetyl, benzoyl, pivaloyl, preferably Bz, and $R_8$, a group orthogonal to all the other protective groups, can be Bn, NAP, p-methoxybenzyl, p-methoxyphenyl, allyl, and preferably Bn, X is preferably a bromine.

This third reaction diagram comprises in the following order:
- the protection reaction [A] of all the OH groups, preferably the protective group is Bz and the reaction is then carried out with BzCl in pyridine,
- selective halogenation [B], advantageously bromination with HBr in AcOH;
- elimination [C], advantageously with DBU diazabicylcoundecene;
- addition [D], advantageously with N-bromosuccinimide in MeOH
- substitution in the anomeric position and elimination of the protected hydroxy group in position 4 of the terminal entity [E], advantageously with $Ph_3PO$ or a Lewis acid such as silver triflate in benzyl alcohol or any other alcohol including naphthalenemethanol, p-methoxybenzyl alcohol, p-methoxyphenol, allyl alcohol;
- epimerizing reduction [F], advantageously with L-selectride;
- selective deprotection [G] of the $R_7$ protective groups, advantageously in MeONa/MeOH;
- selective deprotection [H] of the $R_8$ protective group, advantageously with $H_2$ $Pd(OAc)_2$ when the group is hydrogenolyzable;
- reduction [I] of deoxy-mannose to deoxy-mannitol, advantageously with $NaBH_4$ in $EtOH/H_2O$.

The synthesis intermediates used in the methods described above are novel products. A subject of the invention is therefore also the compounds of formulae (III), (IV), (V) and (VI):

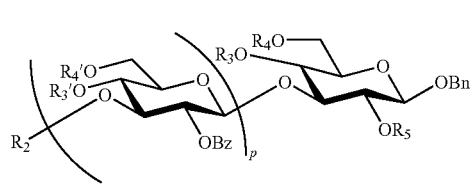

(III)

in which:

p is an integer from 0 to 9, preferably from 0 to 6, and still more preferably equal to 2, 3 or 4;

$R_2$ represents hydrogen, allyl, methylnaphthyl, benzyl, paramethoxybenzyl, halogenoacetyl (chloroacetyl, bromoacetyl, iodoacetyl);

$R_3$ and $R_4$, on the one hand, and $R'_3$ and $R'_4$, on the other hand, together form an ethylidyl, isopropylidyl, hexafluoroisopropylidyl, cyclopentylidyl, cyclohexylidyl, cycloheptylidyl, butylidyl, 1-tertiobutylethylidyl, benzylidyl, methoxybenzylidyl, 1-phenylbenzylidyl radical, or $R_3$, $R_4$, $R_3'$ and $R_4'$ each represent independently of each other a benzyl, chlorobenzyl, nitrobenzyl, allyl, triarylmethyl, trialkylsilyl such as triethylsilyl, tri-isopropylsilyl, tertiobutyldimethylsilyl, ester such as acetyl, chloroacetyl, benzoyl, pivaloyl;

$R_5$ represents H, a levulinoyl, acetyl, chloroacetyl, fluorenylmethyloxycarbonyl, trialkylsilyl group such as triethylsilyl, tri-isopropylsilyl, tertiobutyldimethylsilyl, preferably a levulinoyl group, provided that none of $R_3$, $R_4$, $R_3'$, $R_4'$ is identical to $R_5$;

$R_7$ represents an ester, in particular acetyl, benzoyl, pivaloyl, preferably Bz;

$R_8$, a group orthogonal to all the other protective groups, which can be chosen from Bn, NAP, p-methoxybenzyl, p-methoxyphenyl, allyl, and preferably $R_8$ represents Bn, $R_9$ represents $OR_8$ or X.

The compounds of formula (III) are acceptor compounds A as defined previously.

The invention will be still better understood with the aid of the remainder of the description which follows and examples which are in no way limitative but correspond to advantageous embodiments.

EXAMPLES

Examples 1 to 7 illustrate the methods for synthesis of the products of the invention, and Examples 8 to 11 show the biological activity of the compounds of the invention.

Example 1

Preparation According to Reaction Diagram 1 of β-D-glucopyranosyl-(1→3)-β-D-glucopyranosyl-(1→3)-(α,β)-D-mannopyranose (product A1)

Products 1 and 2 are prepared according to the method described in FR 2 804 684 and Jamois, F.; Ferrières, V.; Guégan, J.-P.; Yvin, J.-C.; Plusquellec, D.; Vetvicka, V. *Glycobiology* 2005, 15, 393-407.

[a]—Preparation of benzyl 4,6-O-benzylidene-3-O-(2-methylnaphthyl)-2-O-levulinoyl-β-D-glucopyranoside of (product 3)

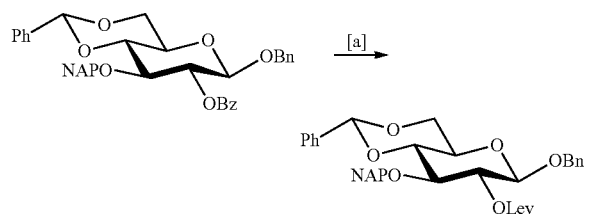

Compound 2 (1 g, 2.006 mmol) is put into solution in 50 mL of dichloromethane then DMAP (50 mg, 4.093 mmol), levulinoic acid (250 µL, 2.441 mmol) and DCC (500 mg, 2.423 mmol) are added. After stirring for 5 hours at ambient temperature, the DCU is eliminated by filtration, then the medium is taken up in 50 mL of dichloromethane and washed with an aqueous solution of 10% hydrochloric acid, a saturated aqueous solution of sodium bicarbonate and a saturated aqueous solution of sodium chloride. After drying the organic phase over $MgSO_4$ and concentration, the compound is purified on silica gel [petroleum ether/ethyl acetate (3:1; v/v)] in order to yield in a quantitative manner 1.2 g of the sought compound 3.

Product 3: white solid; MP (° C.) 133; Rf (EP/AcOEt, 3:1) 0.4; $[\alpha]_D^{20}$ −37.4 (c=1.0, $CH_2Cl_2$).

NMR $^1$H ($CDCl_3$, 400 MHz) δ (ppm): 7.83-7.74 (m, 4H, arom. H); 7.53-7.28 (m, 13H, arom. H); 5.61 (s, 1H, H7); 5.01 (d, 1H, H9, $J_{H9-H9'}$=12.4 Hz); 4.87 (d, 1H, H9'); 4.86 (d, 1H, H8, $J_{H8-H9'}$=12.4 Hz); 4.60 (d, 1H, H8'); 2.58 (t, 2H, H12, $J_{H11-H12}$=6.6 Hz); 2.44 (t, 2H, H11); 2.09 (s, 3H, H14) and Table 1a.

NMR $^{13}$C ($CDCl_3$, 100 MHz) δ (ppm): 206.2 (C13); 171.3 (C10); 137.1, 136.9, 135.6, 133.1, 132.9 (5C, quat. arom. C); 129.0, 128.4, 128.3, 128.2, 128.0, 127.9, 127.8, 127.7, 127.6, 126.8, 126.1, 126.0, 125.8 (arom. C); 101.3 (C7); 74.1 (C9); 70.7 (C8); 37.7 (C12); 29.8 (C14); 27.8 (C11) and Table 1b.

Ultimate analysis ($C_{36}H_{36}O_8$): Theoretical: C=72.47%, H=6.08%; Measured: C=72.05%, H=6.12%.

HRMS (ESI$^+$): [M+Na]$^+$ $C_{36}H_{36}NaO_8$: theoretical m/z: 619.2308, measured m/z: 619.2308; [M+K]$^+$ $C_{36}H_{36}KO_8$: theoretical m/z: 635.2047, measured m/z: 635.2050.

[b] Preparation of benzyl 4,6-O-benzylidene-2-O-levulinoyl-β-D-glucopyranoside (Product 4)

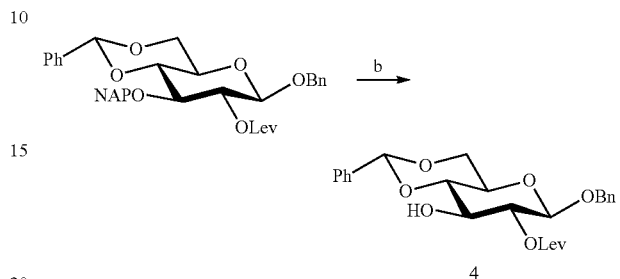

The monosaccharide 3 (1.1 g, 1.844 mmol) and 2,3-dichloro-5,6-dicyano-1,4-benzoquinone (DDQ) (810 mg, 3.568 mmol) are introduced into 50 mL of a dichloromethane/methanol mixture (4:1; v/v) at ambient temperature. After reaction for hour, the medium is diluted with 50 mL of dichloromethane and washed twice with a saturated aqueous solution of sodium bicarbonate. After drying ($MgSO_4$) and concentration of the organic phase, the residue is purified on silica gel [petroleum ether/ethyl acetate (3:1; v/v)]. In this way 690 mg of the sought product 4 is obtained with a yield of 82%.

Product 4: white solid; MP (° C.) 122; Rf (EP/AcOEt, 3:1) 0.2; $[\alpha]_D^{20}$ −62.2 (c=1.0, $CH_2Cl_2$).

NMR $^1$H ($CDCl_3$, 400 MHz) δ (ppm): 7.50-7.48 (m, 2H, arom. H); 7.38-7.28 (m, 8H, arom. H); 5.55 (s, 1H, H7); 4.89 (d, 1H, H8, $J_{H8-H8'}$=12.3 Hz); 4.62 (d, 1H, H8'); 3.05 (s, 1H, OH3); 2.79-2.73 (m, 2H, H11); 2.59-2.51 (m, 2H, H10); 2.09 (s, 3H, H14); 2.16 (s, 3H, H13) and Table 1a.

NMR $^{13}$C ($CDCl_3$, 100 MHz) δ (ppm): 207.1 (C12); 172.0 (C9); 136.9 (2C, quat. arom. C); 129.2, 128.4, 128.3, 127.9, 127.7, 126.3 (arom. C); 101.9 (C7); 70.8 (C8); 38.1 (C11); 29.8 (C13); 28.0 (C10) and Table 1b.

Ultimate analysis ($C_{25}H_{28}O_8$): Theoretical: C=65.78%, H=6.18%; Measured: C=66.04%, H=6.23%.

HRMS (ESI$^+$): [M+Na]$^+$ $C_{25}H_{28}NaO_8$: theoretical m/z: 479.1682, measured m/z: 479.1682; [M+K]$^+$ $C_{25}H_{28}KO_8$: theoretical m/z: 495.1421, measured m/z: 495.1395.

[c] Preparation of benzyl 2-O-benzoyl-4,6-O-benzylidene-3-O-(2-methylnaphthyl)-β-D-glucopyranosyl-(1→3)-4,6-O-benzylidene-2-O-levulinoyl-β-D-glucopyrano side (Product 5)

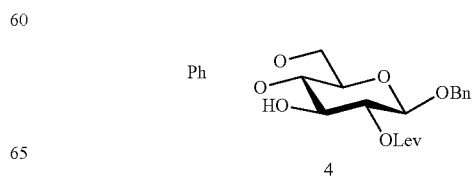

4

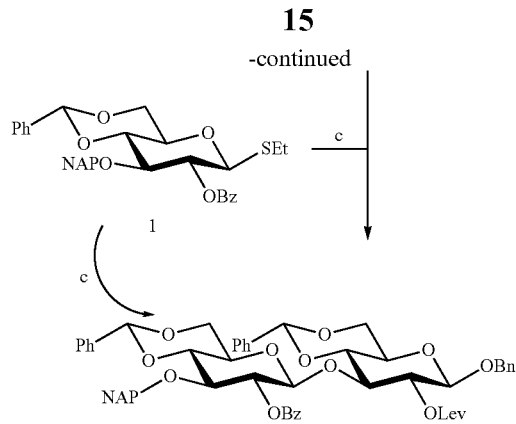

The donor 1 (1.73 g, 3.108 mmol) and the acceptor 4 (1.29 g, 2.826 mmol) are introduced into anhydrous dichloromethane in a flask at −60° C., in the presence of a 4 Å molecular sieve. N-iodosuccinimide (NIS) (763 mg, 3.390 mmol) and trimethylsilyl triflate (50 μL, 0.283 mmol) are then added to the medium. After reaction for 3 hours, the medium is neutralized with triethylamine, filtered then concentrated. After purification by silica gel chromatography [toluene/ethyl acetate (9:1; v/v)], 2.51 g of the sought product 5 is obtained with a yield of 94%.

Product 5: white solid; MP (° C.) 178-179; Rf (EP/AcOEt, 3:1) 0.2; $[\alpha]_D^{20}$ −21.0 (c=1.0, $CH_2Cl_2$).

NMR $^1$H ($CDCl_3$, 400 MHz) δ (ppm): 7.90-7.86 (m, 2H, arom. H); 7.70-7.67 (m, 1H, arom. H); 7.60-7.21 (m, 24H, arom. H); 5.53 (s, 1H, H7b); 5.28 (s, 1H, H7a); 4.94 (d, 1H, H8b, $J_{H8b-H8'b}$=12.1 Hz); 4.84 (d, 1H, H8'b); 4.80 (d, 1H, H8a, $J_{H8a-H8'a}$=12.2 Hz); 4.52 (d, 1H, H8'a); 2.66-2.46 (m, 2H, H10a); 2.40-2.27 (m, 2H, H11a); 2.08 (s, 3H, H13a) and Table 2a.

NMR $^{13}$C ($CDCl_3$, 100 MHz) δ (ppm): 206.4 (C12a); 171.1 (C9a); 165.0 (OCOPh); 137.3, 137.0, 136.7, 135.3, 133.1, 133.0 (7C, quat. arom. C); 132.8, 129.7, 129.4, 128.9, 128.3, 128.2, 127.9, 127.8, 127.7, 127.5, 126.7, 126.1, 126.0, 125.8, 125.6 (arom. C); 101.7 (C7b); 100.9 (C7a); 73.4 (C8b); 70.6 (C8a); 37.8 (C11a); 29.7 (C13a); 27.5 (C10a) and Table 2b.

Ultimate analysis ($C_{56}H_{54}O_{14}$): Theoretical: C=70.72%, H=5.72%; Measured: C=70.89%, H=5.72%.

HRMS (ESI$^+$): [M+Na]$^+$ $C_{56}H_{54}NaO_{14}$, theoretical m/z: 973.3411; measured m/z: 973.3412.

[d]—Preparation of benzyl 2-O-benzoyl-4,6-O-benzylidene-β-D-glucopyranosyl-(1→3)-4,6-O-benzylidene-2-O-levulinoyl-β-D-glucopyranoside (Product 6)

2,3-dichloro-5,6-dicyano-1,4-benzoquinone (820 mg, 3.600 mmol) is added to a solution of compound 5 (1.71 g, 1.800 mmol) in a dichloromethane/methanol mixture (4:1; v/v). After reaction for 16 hours, the medium is diluted with dichloromethane, washed with a saturated solution of sodium bicarbonate and water. The organic phase is dried (MgSO$_4$), evaporated and the sought product 6 is obtained after purification on silica gel [petroleum ether/ethyl acetate (2:1; v/v)] (1.325 g, yield=91%).

Product 6: white solid; MP (° C.) 214; Rf (EP/AcOEt, 2:1) 0.3; $[\alpha]_D^{20}$ −43.0 (c=1.0, $CH_2Cl_2$).

NMR $^1$H ($CDCl_3$, 400 MHz) δ (ppm): 8.06-8.01 (m, 2H, arom. H); 7.63-7.23 (m, 19H, arom. H); 5.57 (s, 1H, H7b); 5.31 (s, 1H, H7a); 4.83 (d, 1H, H8a, $J_{H8a-H8'a}$=12.2 Hz); 4.55 (d, 1H, H8'a); 2.72 (s, 1H, OH3b); 2.65-2.49 (m, 2H, H10a); 2.37-2.25 (m, 2H, H11a); 2.12 (s, 3H, H13a) and Table 2a.

NMR $^{13}$C ($CDCl_3$, 100 MHz) δ (ppm): 206.4 (C12a); 171.1 (C9a); 165.7 (OCOPh); 137.0, 136.9, 136.7 (3C, quat. arom. C); 133.3, 129.8 (arom. C); 129.5 (quat. arom. C); 129.3, 129.1, 128.4, 128.3, 128.2, 128.1, 127.8, 127.6, 126.2, 126.0 (arom. C); 101.6 (C7b); 101.5 (C7a); 70.6 (C8a); 37.7 (C11a); 29.7 (C13a); 27.5 (C10a) and Table 2b.

Ultimate analysis ($C_{45}H_{46}O_{14}$): Theoretical: C=66.66%, H=5.72%; Measured: C=66.53%, H=5.80%.

HRMS (ESI$^+$): [M+Na]$^+$ $C_{45}H_{46}NaO_{14}$: theoretical m/z: 833.2785; measured m/z: 833.2785; [M+K]$^+$ $C_{45}H46KO14$: theoretical m/z: 849.2525, measured m/z: 849.2530.

[c]—Preparation of benzyl 2-O-benzoyl-4,6-O-benzylidene-3-O-(2-methylnaphthyl)-β-D-glucopyranosyl-(1→3)-2-O-benzoyl-4,6-O-benzylidene-β-D-glucopyranosyl-(1→3)-4,6-O-benzylidene-2-O-levulinoyl-β-D-glucopyranoside (Product 7)

The donor 1 (226 mg, 0.406 mmol) and the acceptor 6 (300 mg, 0.370 mmol) are introduced into anhydrous dichloromethane in a flask at −80° C., in the presence of a 4 Å molecular sieve. N-iodosuccinimide (100 mg, 0.444 mmol) and of trimethylsilyl triflate (6.7 μL, 0.037 mmol) are then added to the medium. After stirring for 2 hours, the reaction is stopped and the medium is neutralized with triethylamine, filtered then concentrated. After purification by silica gel chromatography [toluene/ethyl acetate (9:1; v/v)], 328 mg of the expected trisaccharide 7 are obtained with a yield of 68%.

Product 7: white solid; MP (° C.) 115; Rf (EP/AcOEt, 2:1) 0.5; $[\alpha]_D^{20}$ +4.7 (c=1.0, $CH_2Cl_2$).

NMR $^1$H ($CDCl_3$, 400 MHz) δ (ppm): 7.95-7.86 (m, 4H, arom. H); 7.70-7.13 (m, 33H, arom. H); 5.51 (s, 1H, H7); 5.43 (s, 1H, H7); 4.94 (d, 1H, H8c, $J_{H8c-H8'c}$=12.2 Hz); 4.83 (d, 1H, H8'c); 4.78 (d, 1H, H8a, $J_{H8a-H8'a}$=12.4 Hz); 4.50 (s, 1H, H7); 4.49 (d, 1H, H8'a); 2.69-2.47 (m, 2H, H10a); 2.40-2.21 (m, 2H, H11a); 1.95 (s, 3H, H13a) and Table 3 a.

NMR $^{13}$C ($CDCl_3$, 100 MHz) δ (ppm): 206.6 (C12a); 171.1 (C9a); 165.0, 164.8 (2C, OCOPh); 137.3, 137.1, 137.0, 135.4 (quat. arom. C); 133.3, 133.1 (arom. C); 133.0, 132.8 (quat. arom. C); 129.8, 129.7 (arom. C); 129.4 (quat. arom. C); 129.4, 128.9, 128.7, 128.6, 128.3, 128.2, 128.1, 127.9, 127.8, 127.7, 127.6, 127.5, 126.6, 126.4, 126.1, 126.0, 125.7, 125.6 (arom. C); 102.1 (C7); 101.1 (C7); 100.9 (C7); 73.8 (C8c); 70.4 (C8a); 37.7 (C11a); 29.3 (C13a); 27.6 (C10a) and Table 3b.

Ultimate analysis ($C_{76}H_{72}O_{20}$): Theoretical: C=69.93%, H=5.56%; Measured: C=69.89%, H=5.63%.

HRMS (ESI$^+$): [M+Na]$^+$ $C_{76}H_{72}NaO_{20}$: theoretical m/z: 1327.4515, measured m/z: 1327.4522; [M+K]$^+$ $C_{76}H_{72}KO_{20}$: theoretical m/z: 1343.4254, measured m/z: 1343.4206.

[e]—Preparation of benzyl 2-O-benzoyl-4,6-O-benzylidene-3-O-(2-methylnaphthyl)-β-D-glucopyranosyl-(1→3)-2-O-benzoyl-4,6-O-benzylidene-β-D-glucopyranosyl-(1→3)-4,6-O-benzylidene-β-D-glucopyranoside (Product 12)

7.6 mL of a 1M solution of hydrazine in a pyridine/acetic acid mixture (3:2, v/v) are added dropwise to a solution of trisaccharide 7 (500 mg, 0.383 mmol) in pyridine (7.6 mL). After stirring for 3 hours, the reaction is stopped by the addition of 2.1 mL of 2,4-pentane-dione and the medium is concentrated under reduced pressure. The residue is then taken up in 50 mL of dichloromethane and washed with a 10% hydrochloric acid solution, a saturated aqueous solution of sodium bicarbonate and a saturated aqueous solution of sodium chloride. After drying ($MgSO_4$) and concentration, the product is purified by silica gel chromatography [petroleum ether/ethyl acetate (2:1; v/v)] in order to produce 377 mg of compound 12 with a yield of 82%.

Product 12: white solid; MP (° C.) 136; Rf (EP/AcOEt, 2:1) 0.5; $[\alpha]_D^{20}$ +13.4 (c=1.0, $CH_2Cl_2$).

NMR $^1$H ($CDCl_3$, 400 MHz) δ (ppm): 7.94-7.90 (m, 4H, arom. H); 7.68-7.66 (m, 1H, arom. H); 7.58-7.19 (m, 32H, arom. H); 5.54 (s, 1H, H7); 5.52 (s, 1H, H7); 4.95 (d, 1H, H8c, $J_{H8c-H8'c}$=12.4 Hz); 4.88 (d, 1H, H8a, $J_{H8a-H8'a}$=11.6 Hz); 4.83 (d, 1H, H8'c); 4.77 (s, 1H, H7); 4.53 (d, 1H, H8'a) and Table 3a.

NMR $^{13}$C ($CDCl_3$, 100 MHz) δ (ppm): 165.1, 164.7 (2C, OCOPh); 137.3, 137.2, 136.9, 135.3, 133.0, 132.8, 129.2 (8C, quat. arom. C); 133.4, 133.0, 129.8, 129.7, 129.3 (arom. C); 129.2 (quat. arom. C); 129.0, 128.7, 128.5, 128.4, 128.3, 128.2, 128.0, 127.9, 127.8, 127.5, 126.7, 126.4, 126.1, 126.0, 125.7, 125.6 (arom. C); 102.0 (C7); 101.2 (C7); 100.5 (C7); 73.8 (C8c); 71.2 (C8a) and Table 3b.

Ultimate analysis ($C_{71}H_{66}O_{18}$): Theoretical: C=70.64%, H=5.51%; Measured: C=70.49%, H=5.54%.

HRMS (ESI): [M+Na]$^+$ $C_{71}H_{66}NaO_{18}$: theoretical m/z: 1229.4147; measured m/z: 1229.4149; [M+K]$^+$ $C_{71}H_{66}KO_{18}$: theoretical m/z: 1245.3886: measured m/z: 1245.3944; [M-H+2Na]$^+$ $C_{71}H_{65}Na_2O_{18}$: theoretical m/z: 1251.3966; measured m/z: 1251.4040.

[f]—Preparation of benzyl 2-O-benzoyl-4,6-O-benzylidene-3-O-(2-methylnaphthyl)-β-D-glucopyranosyl-(1→3)-2-O-benzoyl-4,6-O-benzylidene-β-D-glucopyranosyl-(1→3)-4,6-O-benzylidene-β-D-glucopyranos-2-uloside (Product 15a)

benzyl 2-O-benzoyl-4,6-O-benzylidene-3-O-(2-methylnaphthyl)-β-D-glucopyranosyl-(1→3)-2-O-benzoyl-4,6-O-benzylidene-β-D-glucopyranosyl-(1→3)-4,6-O-benzylidene-2-C-hydroxyl-β-D-glucopyranoside (Product 15b)

9 mL of a DMSO/acetic acid mixture (2:1, v/v) is added to the deprotected compound 12 (330 mg, 0.273 mmol). After stirring for 48 hours at ambient temperature, the medium is diluted with 50 mL of dichloromethane and washed with a saturated aqueous solution of sodium bicarbonate and with water. After concentration and several co-evaporations with toluene, the medium is purified by silica gel chromatography [petroleum ether/ethyl acetate (3:1; v/v)], in order to produce 180 mg of the oxidized product 15a (yield=55%) in mixture 2:1 with its hydrated form 15b.

Product 15a: white solid; Rf (EP/AcOEt, 2:1) 0.3.

NMR $^1$H ($CDCl_3$, 400 MHz) δ (ppm): 7.95-7.91 (m, 4H, arom. H); 7.67-7.60 (m, 1H, arom. H); 7.57-7.10 (m, 32H, arom. H); 5.53 (s, 1H, H7); 5.41 (s, 1H, H7); 5.40 (dd, 1H, H2c, $J_{H1c-H2c}$=7.8 Hz, $J_{H2c-H3c}$=8.4 Hz); 5.32 (d, 1H, Mc); 5.27 (dd, 1H, H2b, $J_{H1b-H2b}$=2.4 Hz, $J_{H2b-H3b}$=1.6 Hz); 5.19 (d, 1H, H1b); 4.94 (d, 1H, H8c, $J_{H8c-H8'c}$=11.7 Hz); 4.82 (d, 1H, H8'c); 4.82 (d, 1H, H8a, $J_{H8a-H8'a}$=12.0 Hz); 4.64 (s, 1H, H1a); 4.61 (d, 1H, H8'a); 4.42 (s, 1H, H7); 4.35 (d, 1H, H3a, $J_{H3a-H4a}$=10.4 Hz); 4.35 (t, 1H, H6a, $J_{H5a-H6a}$=$J_{H6a-H6'a}$=5.5 Hz); 4.28 (dd, 1H, H6c, $J_{H5c-H6c}$=4.9 Hz, $J_{H6c-H6'c}$=10.4 Hz); 4.24 (dd, 1H, H4b, $J_{H3b-H4b}$=7.5 Hz, $J_{H4b-H5b}$=10.6 Hz); 4.11 (dd, 1H, H6b, $J_{H5b-H6b}$=4.8 Hz, $J_{H6b-H6'b}$=10.2 Hz); 4.01 (dd, 1H, H3b); 3.95 (t, 1H, H3c, $J_{H3c-H4c}$=8.4 Hz); 3.91 (t, 1H, H4c, $J_{H4c-H5c}$=8.4 Hz); 3.77 (t, 1H, H6'c, $J_{H5c-H6'c}$=10.4 Hz); 3.72 (ddd, 1H, H5b, $J_{H5b-H6'b}$=10.2 Hz); 3.63 (ddd, 1H, H5c); 3.56 (t, 1H, H6'a, $J_{H5a-H6'a}$=5.5 Hz); 3.55 (dt, 1H, H5a, $J_{H4a-H5a}$=9.0 Hz); 3.41 (t, 1H, H6'b); 2.98 (dd, 1H, H4a).

NMR $^{13}$C ($CDCl_3$, 100 MHz) δ (ppm): 165.2, 165.0 (2C, OCOPh); 137.3, 137.2, 136.8, 135.9, 135.4 (quat. arom. C); 133.5, 133.3 (arom. C); 133.0, 132.8 (quat. arom. C); 129.8, 129.7, 129.3, 129.2 (arom. C); 129.0 (quat. arom. C); 129.0, 128.9, 128.7, 128.5, 128.4, 128.3, 128.2, 128.1, 128.0, 127.9, 127.8, 127.5, 126.7, 126.4, 126.2, 126.1, 126.0, 125.7, 125.6 (arom. C); 101.6 (C7); 101.2 (C7); 100.6 (C7); 98.6 (C1a); 97.6 (C1c); 96.1 (C1b); 81.6 (C4c); 79.9 (C4a); 78.1 (C3c); 77.4 (C4b); 75.9 (C3a); 75.8 (C3b); 73.9 (C8c); 73.1 (C2c); 71.8 (C2b); 70.3 (C8a); 68.9 (C6b); 68.7 (C6c); 68.3 (C6a); 66.4 (C5a); 66.2 (C5c); 64.9 (C5b).

HRMS (ESI$^+$): [M+Na]$^+$ $C_{71}H_{64}NaO_{18}$: theoretical m/z: 1227.3990; measured m/z: 1227.3988; [M+Na+$CH_3OH$]$^+$ $C_{72}H_{68}NaO_{19}$: theoretical m/z: 1259.4252, measured m/z: 1259.4245.

Product 15b:

NMR $^1$H ($CDCl_3$, 400 MHz) δ (ppm): Characteristic signals at 5.24 (d, 1H, H3a, $J_{H3a-H4a}$=2.9 Hz); 4.30 (s, 1H, H1a).

NMR $^{13}$C ($CDCl_3$, 100 MHz) δ (ppm): Characteristic signals at 100.4 (C1a); 93.4 (C2a).

[g]—Preparation of benzyl 2-O-benzoyl-4,6-O-benzylidene-3-O-(2-methylnaphthyl)-β-D-glucopyranosyl-(1→3)-2-O-benzoyl-4,6-O-benzylidene-β-D-glucopyranosyl-(1→3)-4,6-O-benzylidene-β-D-mannopyranoside (Product 18)

The oxidized compound 15a/15b (180 mg, 0.149 mmol) is solubilized in a dichloromethane/THF mixture (1:1, v/v) then L-Selectride (1M in THF; 150 μL, 0.150 mmol) is added at −78° C. After 45 minutes at −78° C., the reaction is assumed to be completed and the medium neutralized by the addition of a few drops of acetic acid. Once the medium has returned to ambient temperature, 30 mL of dichloromethane are added and the organic phase is washed with a 10% aqueous hydrochloric acid solution, a saturated aqueous solution of sodium bicarbonate and finally with a saturated aqueous solution of sodium chloride. 180 mg of the desired reduced mannoside compound 18 are thus obtained after drying ($MgSO_4$) and concentration of the organic phase.

Product 18: white solid; MP (° C.) 180; Rf (EP/AcOEt, 2:1) 0.2; $[\alpha]_D^{20}$ −4.4 (c=1.0, $CH_2Cl_2$).

NMR $^1$H ($CDCl_3$, 400 MHz) δ (ppm): 7.85-7.83 (m, 2H, arom. H); 7.73-7.67 (m, 3H, arom. H); 7.62-7.17 (m, 32H, arom. H); 5.50 (s, 1H, H7); 5.42 (s, 1H, H7); 5.21 (s, 1H, H7); 4.90 (d, 1H, H8c, $J_{H8c-H8'c}$=12.4 Hz); 4.87 (d, 1H, H8a, $J_{H8a-H8'a}$=12.2 Hz); 4.80 (d, 1H, H8'c); 4.59 (d, 1H, H8'a) and Table 3'a.

NMR $^{13}$C ($CDCl_3$, 100 MHz) δ (ppm): 164.8, 164.8 (2C, OCOPh); 137.2, 137.1, 136.5, 135.2 (quat. arom. C); 133.2 (arom. C); 132.9, 132.8 (quat. arom. C); 132.8, 129.7, 129.6 (arom. C); 129.4, 129.1 (quat. arom. C); 129.0, 128.9, 128.7, 128.5, 128.4, 128.3, 128.2, 128.1, 128.0, 127.8, 127.5, 126.7, 126.4, 126.3, 126.1, 126.0, 125.7, 125.6 (arom. C); 101.5 (C7); 101.1 (2C, C7); 73.5 (C8c); 70.4 (C8a) and Table 3'b.

[h]—Preparation of benzyl 4,6-O-benzylidene-3-O-(2-methylnaphthyl)-β-D-glucopyranosyl-(1→3)-4,6-O-benzylidene-β-D-glucopyranosyl-(1→3)-4,6-O-benzylidene-β-D-mannopyranoside (Product 19)

Compound 18 (170 mg, 0.141 mmol) is dissolved in 15 mL of a methanol/dichloromethane mixture (2:1, v/v) then 2 equivalents of sodium methylate (0.1M in MeOH, 3 mL, 0.300 mmol) are added. After stirring for 6 hours at ambient temperature, the medium is neutralized by the addition of Amberlite IR120-H⁺ resin, filtered then concentrated under reduced pressure. After chromatography [dichloromethane/methanol (99:1; v/v)], compound 19 is obtained with a yield of 72% (126 mg).

Product 19: white solid; MP (° C.)>230; Rf (CH$_2$Cl$_2$/MeOH, 97:3) 0.4; $[\alpha]_D^{20}$ −43.5 (c=1.0, CH$_2$Cl$_2$).

NMR $^1$H (CDCl$_3$, 400 MHz) δ (ppm): 7.70-7.19 (m, 27H, arom. H); 5.47 (s, 1H, H7); 5.44 (s, 1H, H7); 5.42 (s, 1H, H7); 4.96 (d, 1H, H8c, $J_{H8c-H8'c}$=12.0 Hz); 4.88 (d, 1H, H8'c); 4.84 (d, 1H, H8a, $J_{H8a-H8'a}$=11.9 Hz); 4.56 (d, 1H, H8'a) and Table 3'a.

NMR $^{13}$C (CDCl$_3$, 100 MHz) δ (ppm): 137.1, 137.0, 136.9, 136.2, 135.8, 133.1, 132.8 (7C, quat. arom. C); 129.0, 128.9, 128.8, 128.5, 128.4, 128.3, 128.2, 128.1, 128.0, 127.9, 127.8, 127.6, 127.5, 127.4, 126.8, 126.5, 126.2, 126.1, 126.0, 125.9, 125.8, 125.7 (arom. C); 101.6 (C7); 101.2 (C7); 100.7 (C7); 74.4 (C8c); 70.7 (C8a) and Table 3'b.

HRMS (ESI): [M+Na]⁺ C$_{57}$H$_{58}$NaO$_{16}$: theoretical m/z: 1021.3623, measured m/z: 1021.3624; [M+K]⁺ C$_{57}$H$_{58}$KO$_{16}$: theoretical m/z: 1037.3362, measured m/z: 1037.3370; [M-H+2Na]⁺ C$_{57}$H57Na$_2$O$_{16}$: theoretical m/z: 1043.3442, measured m/z: 1043.3463.

[i]—β-D-glucopyranosyl-(1→3)-β-D-glucopyranosyl-(1→3)-(α,β)-D-mannopyranose (Product A1)

The trisaccharide 18 (90 mg, 0.090 mmol), then palladium acetate (60 mg, 0.267 mmol) are introduced into 10 mL of an ethyl acetate/methanol/dichloromethane mixture (2:2:1; v/v/v). The medium is then stirred vigorously at ambient temperature under a hydrogen atmosphere for 7 days. After filtration on celite, the hydro-organic phase is extracted with dichloromethane, then brought to dryness by azeotropic coevaporation with absolute ethanol in order to lead in quantitative manner to the deprotected compound (45 mg, 0.090 mmol). 25 mg of the compound formed are then purified by exclusion chromatography on Sephadex G-10 gel (eluent: water) and the fractions collected are freeze-dried in order to obtain the sought product which is presented in the form of a white foam.

NMR $^1$H (D$_2$O, 400 MHz) δ (ppm): 5.13 (d, 1H, H1 aα, $J_{H1a-H2a}$=1.8 Hz); 4.67 (d, 1H, H1c, $J_{H1c-H2c}$=7.7 Hz); 4.53 (d, 1H, H1b, $J_{H1b-H2b}$=8.0 Hz); 4.03 (dd, 1H, H2a, $J_{H2a-H3a}$=3.1 Hz); 3.96 (dd, 1H, H3a, $J_{H3a-H4a}$=9.5 Hz); 3.90-3.80 (m, 3H, H6a, H6b, H6c); 3.80-3.73 (m, 1H, H4a); 3.72-3.55 (m, 5H, H5a, H6'a, H3b, H6'b, H6'c); 3.53-3.36 (m, 5H, H2b, H64b, H5b, H3c, H5c); 3.32 (t, 1H, H4c, $J_{H3c-H4c}$=$J_{H4c-H5c}$=9.7 Hz); 3.27 (dd, 1H, H2c, $J_{H2c-H3c}$=9.3 Hz).

NMR $^{13}$C (D$_2$O, 100 MHz) δ (ppm): 103.1 (C1c); 100.5 (C1b); 94.1 (C1aα); 84.5 (C3b); 78.5 (C3a); 76.3 (C5c); 75.9 (2C, C3c, C5b); 75.8 (C2c); 73.1 (C2b); 72.7 (C4a); 69.9 (C4c); 68.6 (C2a); 68.4 (C4b); 65.5 (C5a); 61.2, 61.0 (3C, C6a, C6b, C6c).

HRMS (ER): [M+Na]⁺ C$_{18}$H$_{32}$NaO$_{16}$: theoretical m/z: 527.1588, measured m/z: 527.1587; [M+K]⁺ C$_{18}$H$_{32}$KO$_{16}$: theoretical m/z: 543.1327, measured m/z: 543.1343.

Example 2

Synthesis of Different Intermediates

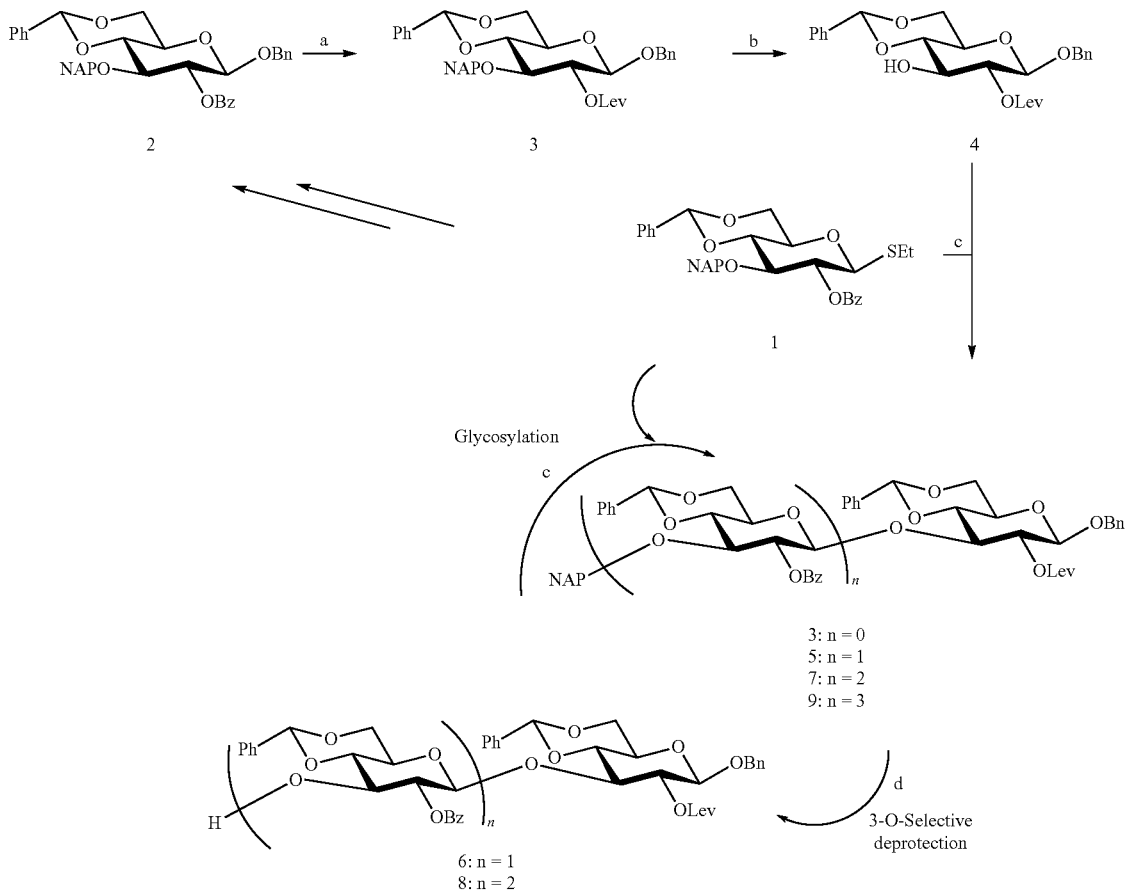

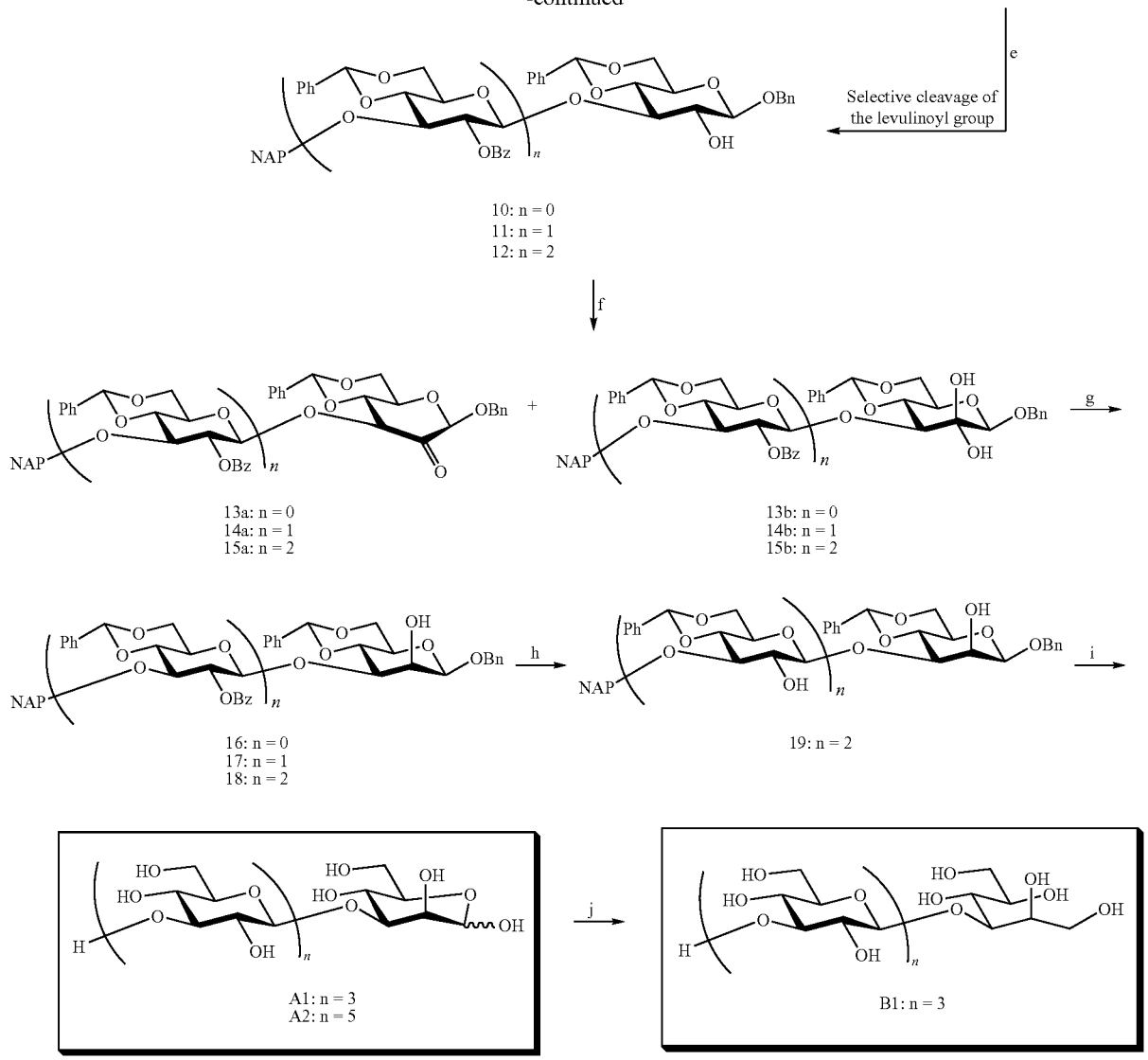

2.1/ benzyl 2-O-benzoyl-4,6-O-benzylidene-β-D-glucopyranosyl-(1→3)-2-O-benzoyl-4,6-O-benzylidene-β-D-glucopyranosyl-(1→3)-4,6-O-benzylidene-2-O-levulinoyl-β-D-glucopyranoside (Product 8)

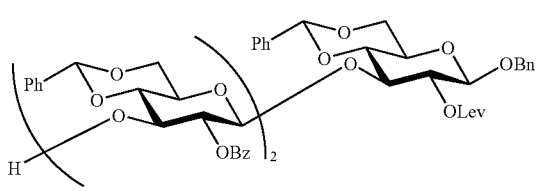

2,3-dichloro-5,6-dicyano-1,4-benzoquinone (176 mg, 0.774 mmol) is added to a solution of trisaccharide compound 7 (337 mg, 0.258 mmol) in a dichloromethane/methanol mixture (4:1; v/v). After stirring for 16 hours at ambient temperature, the reaction is stopped and the medium is diluted with dichloromethane, washed with a saturated solution of sodium bicarbonate then with water. The organic phase is dried over MgSO$_4$, concentrated and the sought product 8 is obtained after purification on silica gel [petroleum ether/ethyl acetate (2:1; v/v)] (185 mg, yield=72%).

Product 8: white solid; Rf (EP/AcOEt, 2:1) 0.2.

NMR $^1$H (CDCl$_3$, 400 MHz) δ (ppm): 8.01-7.95 (m, 2H, arom. H); 7.90-7.84 (m, 2H, arom. H); 7.53-7.18 (m, 24H, arom. H); 7.15-7.09 (m, 2H, arom. H); 5.39 (s, 1H, H7); 5.37 (s, 1H, H7); 4.74 (d, 1H, H8a, $J_{H8a-H8'a}$=12.2 Hz); 4.47 (s, 1H, H7); 4.45 (d, 1H, H8'a); 2.66 (s, 1H, OH3c); 2.66-2.44 (m, 2H, H10a); 2.36-2.20 (m, 2H, H11a); 1.91 (s, 3H, H13a) and Table 3a.

NMR $^{13}$C (CDCl$_3$, 100 MHz) δ (ppm): 206.1 (C12a); 171.1 (C9a); 165.7, 164.8 (2C, OCOPh); 137.3, 137.0, 136.9, 133.5, 133.2 (6C, quat. arom. C); 129.9, 129.7, 129.5, 129.4, 129.2, 128.7, 128.4, 128.3, 128.2, 127.9, 127.8, 127.7, 127.6, 126.4, 126.2, 126.0 (arom. C); 102.1, 101.7, 100.4 (3C, C7); 70.4 (C8a); 37.7 (C11a); 29.3 (C13a); 27.7 (C10a) and Table 3b.

2.2/ benzyl 2-O-benzoyl-4,6-O-benzylidene-3-O-(2-methylnaphthyl)-β-D-glucopyranosyl-(1→3)-2-O-benzoyl-4,6-O-benzylidene-β-D-glucopyranosyl-(1→3)-2-O-benzoyl-4,6-O-benzylidene-β-D-glucopyranosyl-(1→3)-4,6-O-benzylidene-2-O-levulinoyl-β-D-glucopyranoside (Product 9)

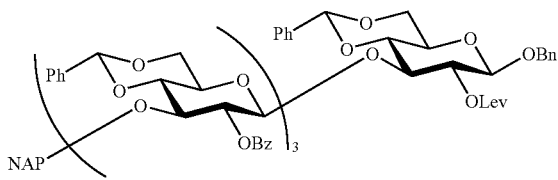

The donor 1 (26 mg, 0.047 mmol) and the trisaccharide acceptor 8 (50 mg, 0.043 mmol) are introduced into anhydrous dichloromethane in a flask at 0° C., in the presence of a 4 Å molecular sieve. After the addition of N-iodosuccinimide (NIS) (50 mg, 0.051 mmol) and trimethylsilyl triflate (0.65 µL, 0.004 mmol), the mixture is left under vigorous stirring for 30 minutes. Once reaction has stopped, the medium is neutralized with triethylamine, filtered then concentrated. After purification by silica gel chromatography [toluene/ethyl acetate (2:1; v/v)], 24 mg of desired tetrasaccharide 9 are obtained with a yield of 34%.

Product 9: white solid; MP (° C.) 138; Rf (EP/AcOEt, 2:1) 0.3; $[\alpha]_D^{20}$ 8.4 (c=1.0, $CH_2Cl_2$).

NMR $^1$H ($CDCl_3$, 400 MHz) δ (ppm): 7.94-7.74 (m, 6H, arom. H); 7.58-7.17 (m, 41H, arom. H); 5.48 (s, 1H, H7); 5.44 (s, 1H, H7); 5.33 (dd, 1H, H2d, $J_{H1d\text{-}H2d}$=6.9 Hz, $J_{H2d\text{-}H3d}$=8.2 Hz); 5.21 (t, 1H, H2c, $J_{H1c\text{-}H2c}$=5.8 Hz); 5.06 (d, 1H, H1c); 4.97 (d, 1H, H1b, $J_{H1b\text{-}H2b}$=5.8 Hz); 4.96 (d, 1H, H1d); 4.96 (s, 1H, H7); 4.90 (d, 1H, H8d, $J_{H8d\text{-}H8'd}$=12.4 Hz); 4.82 (t, 1H, H2b, $J_{H2b\text{-}H3b}$=5.8 Hz); 4.80 (d, 1H, H8'd); 4.79 (d, 1H, H8a, $J_{H8a\text{-}H8'a}$=12.4 Hz); 4.68 (dd, 1H, H2a, $J_{H1a\text{-}H2a}$=8.0 Hz, $J_{H2a\text{-}H3a}$=8.6 Hz); 4.63 (s, 1H, H7); 4.51 (d, 1H, H8'a); 4.35 (d, 1H, H1a); 4.31 (dd, 1H, H6a, $J_{H5a\text{-}H6a}$=4.9 Hz, $J_{H6a\text{-}H6'a}$=10.6 Hz); 4.21 (dd, 1H, H6d, $J_{H5d\text{-}H6d}$=4.9 Hz, $J_{H6d\text{-}H6'd}$=10.4 Hz); 4.16 (dd, 1H, H6c, $J_{H5c\text{-}H6c}$=5.6 Hz, $J_{H6c\text{-}H6'c}$=10.4 Hz); 4.11 (dd, 1H, H6b, $J_{H5b\text{-}H6b}$=5.3 Hz, $J_{H6b\text{-}H6'b}$=9.1 Hz); 4.08 (dd, 1H, H3c, $J_{H3c\text{-}H4c}$=8.8 Hz); 4.01 (dd, 1H, H3b, $J_{H3b\text{-}H4b}$=8.4 Hz); 3.98 (t, 1H, H4c, $J_{H4c\text{-}H5c}$=8.8 Hz); 3.90 (dd, 1H, H4d, $J_{H3d\text{-}H4d}$=8.2 Hz, $J_{H4d\text{-}H5d}$=9.1 Hz); 3.90 (dd, 1H, H3a, $J_{H3a\text{-}H4a}$=9.1 Hz); 3.82 (t, 1H, H3d); 3.73 (t, 1H, H6'd, $J_{H5d\text{-}H6'd}$=10.4 Hz); 3.67 (t, 1H, H6'a, $J_{H5a\text{-}H6'a}$=10.6 Hz); 3.62-3.58 (m, 2H, H5c, H6'c); 3.61 (dd, 1H, H4b, $J_{H4b\text{-}H5b}$=9.1 Hz); 3.50 (t, 1H, H6'b, $J_{H5b\text{-}H6'b}$=9.1 Hz); 3.48 (dt, 1H, H5b); 3.44 (ddd, 1H, H5d); 3.34 (ddd, 1H, H5a, $J_{H4a\text{-}H5a}$=9.1 Hz); 3.16 (t, 1H, H4a); 2.64-2.50 (m, 2H, H10a); 2.36-2.21 (m, 2H, H11a); 2.00 (s, 3H, H13a).

NMR $^{13}$C ($CDCl_3$, 100 MHz) δ (ppm): 206.0 (C12a); 171.1 (C9a); 164.9, 164.8, 164.5 (3C, OCOPh); 137.3, 137.1, 136.9, 135.3 (quat. arom. C); 133.3, 133.2 (arom. C); 133.0, 132.8 (quat. arom. C); 129.7 (arom. C); 129.4 (quat. arom. C); 129.4, 128.9, 128.8, 128.5, 128.4, 128.3, 128.2, 128.0, 127.9, 127.8, 127.7, 127.5, 126.6, 126.4, 126.2, 126.0, 125.9, 125.7, 125.6 (arom. C); 102.0 (C7); 101.1 (C7); 100.8 (2C, C7); 99.7 (C1a); 99.3 (C1d); 97.8 (C1b); 96.8 (C1c); 81.1 (C4d); 78.8 (C4a); 78.5 (C4c); 78.1 (C3d); 77.4 (C4b); 77.2 (C3c); 74.3 (2C, C3a, C3b); 73.6 (2C, C8d, C2a); 73.4 (C2d); 73.2 (C2b); 72.8 (C2c); 70.5 (C8a); 68.7 (3C, C6b, C6c, C6d); 68.5 (C6a); 66.3 (C5a); 65.9 (C5d); 65.7 (C5c); 65.3 (C5b); 37.7 (C11a); 29.5 (C13a); 27.6 (C10a).

Ultimate analysis ($C_{96}H_{90}O_{26}$): Theoretical: C=69.47%, H=5.47%; Measured: C=69.57%, H=5.58%.

HRMS (ESI$^+$): [M+Na]$^+$ $C_{96}H_{90}NaO_{26}$: theoretical m/z: 1681.5618, measured m/z: 1681.5619; [M+K]$^+$ $C_{96}H_{90}KO_{26}$: theoretical m/z: 1697.5357, measured m/z: 1697.5398.

2.3/ benzyl 4,6-O-benzylidene-3-O-(2-methylnaphthyl)-β-D-glucopyranoside (Product 10)

Sodium (0.7 g, 30.435 mmol) is added to a solution of 3 (5 g, 8.296 mmol) in anhydrous methanol (150 mL). The mixture is stirred at 50° C. until the starting product is completely consumed. The medium is then cooled down, neutralized by adding a stoichiometric quantity of acetic acid and concentrated. The residue is then dissolved in dichloromethane (250 mL), extracted 3 times with 50 mL of water. The organic phase is dried over $MgSO_4$ then concentrated. Purification on silica gel [petroleum ether/ethyl acetate (3:1; v/v)] makes it possible to obtain 3.7 g of the debenzoylated compound 10 with a yield of 83%.

Product 10: white solid; MP (° C.) 148; Rf (EP/AcOEt, 3:1) 0.7; $[\alpha]_D^{20}$ −48.1 (c=1.0, $CH_2Cl_2$).

NMR $^1$H ($CDCl_3$, 400 MHz) δ (ppm): 7.86-7.80 (m, 2H, arom. H); 7.78-7.72 (m, 1H, arom. H); 7.52-7.30 (m, 14H, arom. H); 5.60 (s, 1H, H7); 5.10 (d, 1H, H9, $J_{H9\text{-}H9'}$=12.0 Hz); 4.98 (d, 1H, H9'); 4.94 (d, 1H, H8, $J_{H8\text{-}H8'}$=11.8 Hz); 4.65 (d, 1H, H8'); 2.46 (s, 1H, OH) and Table 1a.

NMR $^{13}$C ($CDCl_3$, 100 MHz) δ (ppm): 137.2, 136.8, 135.7, 133.2, 133.0 (5C, quat. arom. C); 129.0, 128.5, 128.3, 128.2, 128.1, 128.0, 127.9, 127.6, 126.8, 126.2, 126.1, 126.0, 125.9, 125.8, 125.4, 125.1 (arom. C); 101.4 (C7); 74.6 (C9); 71.4 (C8) and Table 1a.

Ultimate analysis ($C_{31}O_{30}O_6$): Theoretical: C=74.68%, H=6.07%; Measured: C=74.76%, H=6.04%.

HRMS (ESI$^+$): [M+Na]$^+$ $C_{31}H_{30}NaO_6$: theoretical m/z: 521.1940, measured m/z: 521.1948; [M+K]$^+$ $C_{31}H_{30}KO_6$: theoretical m/z: 537.1679, measured m/z: 521.1999.

2.4/ benzyl 2-O-benzoyl-4,6-O-benzylidene-3-O-(2-methylnaphthyl)-β-D-glucopyranosyl-(1→3)-4,6-O-benzylidene-β-D-glucopyranoside (Product 11)

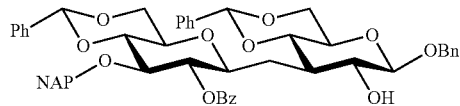

200 µL of a 1M solution of hydrazine in a pyridine/acetic acid mixture (3:2, v/v) are added dropwise to a solution of the disaccharide 5 (11 mg, 0.011 mmol) in pyridine (0.2 mL). After stirring for 1 hour, the reaction is stopped by the addition of 50 µL of 2,4-pentane-dione and the medium is concentrated under reduced pressure. The residue is then taken up in 20 mL of dichloromethane and washed with a 10% hydrochloric acid solution, a saturated aqueous solution of sodium bicarbonate and a saturated aqueous solution of sodium chloride. After drying the organic phase on MgSO$_4$ and evaporation of the solvent, the product is purified by silica gel chromatography [petroleum ether/ethyl acetate (2:1; v/v)] in order to produce 6 mg of compound 11 with a yield of 61%.
Product 10: white solid; Rf (EP/AcOEt, 2:1) 0.6.

NMR $^1$H (CDCl$_3$, 400 MHz) δ (ppm): 7.93-7.89 (m, 2H, arom. H); 7.70-7.23 (m, 25H, arom. H); 5.54 (s, 1H, H7b); 5.45 (s, 1H, H7a); 4.95 (d, 1H, H8b, $J_{H8b-H8'b}$=12.9 Hz); 4.86 (d, 1H, H8'b); 4.85 (d, 1H, H8a, $J_{H8a-H8'a}$=11.7 Hz); 4.56 (d, 1H, H8'a) and Tables 2a and 2b.

NMR $^{13}$C (CDCl$_3$, 100 MHz) δ (ppm): 165.5 (OCOPh); 137.2, 137.1, 136.7, 135.2, 133.1, 132.8 (7C, quat. arom. C); 133.0, 129.8, 129.7, 129.1, 129.0, 128.5, 128.4, 128.2, 128.0, 127.9, 127.8, 127.6, 126.9, 126.1, 126.0, 125.8, 125.7 (arom. C); 102.0 (C7b); 101.3 (C7a); 74.0 (C8b); 71.3 (C8a) and Table 2c.

HRMS (ER): [M+Na]$^+$ C$_{51}$H$_{48}$NaO$_{12}$: theoretical m/z: 875.3044, measured m/z: 875.3040; [M+K]$^+$ C$_{51}$H$_{48}$KO$_{12}$: theoretical m/z: 891.2783, measured m/z: 891.2748

2.5/ benzyl 4,6-O-benzylidene-3-O-(2-methylnaphthyl)-β-D-glucopyranos-2-uloside (13a)

benzyl 4,6-O-benzylidene-2-C-hydroxyl-3-O-(2-methylnaphthyl)-β-D-glucopyranoside (13b)

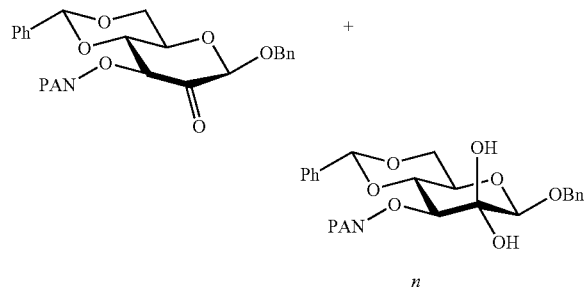

Compound 10 (43.5 mg, 0.087 mmol) is put into solution in 1 mL of a DMSO/acetic anhydride mixture (2:1; v/v). After stirring for 20 hours at ambient temperature, the medium is taken up in 50 mL of ethyl acetate and washed with a saturated aqueous solution of sodium bicarbonate and a saturated aqueous solution of sodium chloride. After drying (MgSO$_4$) and concentration of the organic phase, the compound is purified by silica gel chromatography [petroleum ether/ethyl acetate (3:1; v/v)] in order to obtain 33 mg of a 5:1 mixture of the sought compound 13a and the hydrated compound 13b, with a yield of 76%.
White solid; Rf (EP/AcOEt, 3:1) 0.3.
Product 13a:

NMR $^1$H (CDCl$_3$, 400 MHz) δ (ppm): 7.75-7.66 (m, 3H, arom. H); 7.57-7.54 (m, 1H, arom. H); 7.43-7.20 (m, 13H, arom. H); 5.49 (s, 1H, H7); 5.03 (d, 1H, H9, $J_{H9-H9'}$=12.7 Hz); 4.84 (d, 1H, H8, $J_{H8-H9'}$=12.0 Hz); 4.80 (d, 1H, H9'); 4.72 (s, 1H, H1); 4.62 (d, 1H, H8'); 4.35 (dd, 1H, H6, $J_{H5-H6}$=4.8 Hz, $J_{H5-H6'}$=10.4 Hz); 4.13 (d, 1H, H3, $J_{H3-H4}$=10.2 Hz); 3.90 (t, 1H, H4, $J_{H4-H5}$=10.2 Hz); 3.77 (t, 1H, H6', $J_{H5-H6'}$=10.4 Hz); 3.58 (ddd, 1H, H5).

NMR $^{13}$C (CDCl$_3$, 100 MHz) δ (ppm): 196.7 (C2); 136.8, 135.9, 134.6, 133.1, 133.0 (5C, quat. arom. C); 129.2, 128.6, 128.2, 128.1, 127.9, 127.6, 127.1, 126.7, 126.1, 126.0, 125.9, 125.7 (arom. C); 101.2 (C7); 99.0 (C1); 82.0 (C4); 81.8 (C3); 73.1 (C9); 70.5 (C8); 68.5 (C6); 66.4 (C5).

Product 13b:
NMR $^1$H (CDCl$_3$, 400 MHz) δ (ppm): 7.75-7.66 (m, 3H, arom. H); 7.63-7.59 (m, 1H, arom. H); 7.43-7.20 (m, 13H, arom. H); 5.49 (s, 1H, H7); 4.97 (d, 1H, H9, $J_{H9-H9'}$=11.9 Hz); 4.94 (d, 1H, H9'); 4.84 (d, 1H, H8, $J_{H8-H8'}$=11.7 Hz); 4.58 (d, 1H, H8'); 4.38 (s, 1H, H1); 4.28 (dd, 1H, H6, $J_{H5-H6}$=4.8 Hz, $J_{H6-H6'}$=10.4 Hz); 3.84 (t, 1H, H4, $J_{H3-H4}$=$J_{H4-H5}$=9.9 Hz); 3.80 (dd, 1H, H6', $J_{H5-H6'}$=9.7 Hz); 3.62 (d, 1H, H3); 3.34 (ddd, 1H, H5); 1.97, 1.95 (2s, 2H, OH2).

NMR $^{13}$C (CDCl$_3$, 100 MHz) δ (ppm): 136.9, 136.1, 134.8, 133.1, 133.0 (5C, quat. arom. C); 129.0, 128.6, 128.3, 128.2, 128.1, 127.9, 127.6, 127.1, 126.7, 126.2, 126.0, 125.9, 125.7 (arom. C); 101.4 (C7); 100.5 (C1); 93.9 (C2); 79.9 (C4); 79.8 (C3); 74.9 (C9); 71.5 (C8); 68.5 (C6); 66.5 (C5).

2.6/ benzyl 2-O-benzoyl-4,6-O-benzylidene-3-O-(2-methylnaphthyl)-β-D-glucopyranosyl-(1→3)-4,6-O-benzylidene-β-D-glucopyranos-2-uloside (Product 14a)

benzyl 2-O-benzoyl-4,6-O-benzylidene-3-O-(2-methylnaphthyl)-β-D-glucopyranosyl-(1→3)-4,6-O-benzylidene-2-C-hydroxyl-β-D-glucopyranoside (Product 14b)

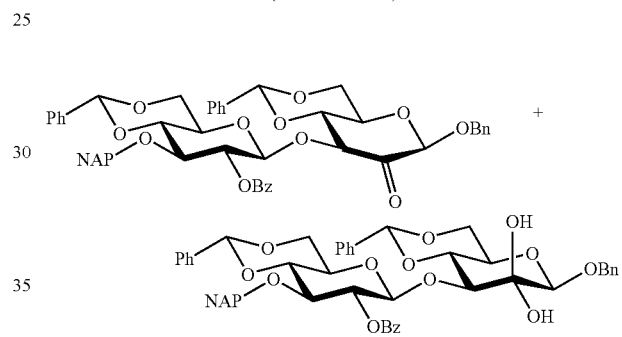

Compound 11 (6 mg, 0.007 mmol) is put into solution in 1 mL of a DMSO/acetic anhydride mixture (2:1; v/v). After stirring for 20 hours at ambient temperature, the medium is taken up in 50 mL of ethyl acetate and washed with a saturated aqueous solution of sodium bicarbonate and a saturated aqueous solution of sodium chloride. After drying (MgSO$_4$) and concentration of the organic phase, the compound is purified by silica gel chromatography [petroleum ether/ethyl acetate (2:1; v/v)] in order to obtain 6 mg of a 1:5 mixture of the sought compound 14a and the hydrated compound 14b, with a quantitative yield.
White solid; Rf (EP/AcOEt, 2:1) 0.3.
Product 14a:
NMR $^{13}$C (CDCl$_3$, 100 MHz) δ (ppm): Characteristic signal at 192.2 (C2a).
HRMS (ESI$^+$): [M+Na]$^+$ C$_{51}$H$_{46}$NaO$_{12}$: theoretical m/z: 873.2887; measured m/z: 873.2886; [M'+Na]$^+$ C$_{51}$H$_{48}$NaO$_{13}$: theoretical m/z: 891.2993, measured m/z: 891.2982.
Product 14b:
NMR $^1$H (CDCl$_3$, 400 MHz) δ (ppm): 7.92-7.88 (m, 2H, arom. H); 7.73-7.22 (m, 25H, arom. H); 5.56 (s, 1H, H7); 5.50 (s, 1H, H7); 5.38 (t, 1H, H2b, $J_{H1b-H2b}$=$J_{H2b-H3b}$=8.0 Hz); 4.96 (d, 1H, H8b, $J_{H8b-H8'b}$=12.4 Hz); 4.90 (d, 1H, H8a, $J_{H8a-H8'a}$=12.0 Hz); 4.89 (d, 1H, H8'b); 4.86 (d, 1H, H1b); 4.58 (d, 1H, H8'a); 4.34 (dd, 1H, H6b, $J_{H5b-H6b}$=4.9 Hz, $J_{H6b-H6'b}$=10.6 Hz); 4.30 (s, 1H, H1a); 4.27 (dd, 1H, H6a, $J_{H5a-H6a}$=5.1 Hz, $J_{H6a-H6'a}$=10.6 Hz); 3.99-3.76 (m, 5H, H4a, H6'a, H3b, H4b, H6'b); 3.75 (d, 1H, H3a, $J_{H3a-H4a}$=9.5 Hz);

3.48 (dt, 1H, H5b, $J_{H4b-H5b}=J_{H5b-H6'b}$=9.5 Hz); 3.36 (dt, 1H, H5a, $J_{H4a-H5a}=J_{H5a-H6'a}$=10.0 Hz).

NMR $^{13}$C (CDCl$_3$, 100 MHz) δ (ppm): 166.3 (OCOPh); 137.2, 137.1, 136.1, 135.1, 132.9 (quat. arom. C); 133.3, 133.0, 129.9, 129.5, 129.1, 129.0, 128.6, 128.5, 128.4, 128.3, 128.2, 128.1, 128.0, 127.9, 127.6, 127.0, 126.3, 126.2, 126.1, 125.9, 125.8 (arom. C); 103.0 (C1b); 101.2, 101.0 (C7); 100.4 (C1a); 93.4 (C2a); 81.9 (C3a); 81.0 (C4b); 78.1 (C4a); 77.6 (C3b); 74.4 (C2b); 73.9 (C8b); 71.4 (C8a); 68.6 (C6a); 68.4 (C6b); 66.8 (C5a); 65.9 (C5b).

2.7/ benzyl 4,6-O-benzylidene-3-O-(2-methylnaph-thyl)-β-D-mannopyranoside (Product 16)

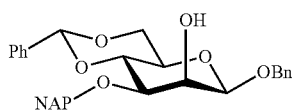

An equivalent of L-Selectride (1M in THF; 70 μL, 0.070 mmol) is added to a solution of the 13a/13b mixture (33 mg, 0.067 mmol) in THF (0.5 mL) at −80° C. After stirring for 15 minutes at −80° C., the medium is diluted with 10 mL of dichloromethane and washed with a 10% aqueous hydrochloric acid solution, a saturated aqueous solution of sodium bicarbonate and a saturated aqueous solution of sodium chloride. After drying over MgSO$_4$ and evaporation of the solvent, the compound is purified by silica gel chromatography [petroleum ether/ethyl acetate (3:1; v/v)] in order to obtain 28 mg of the sought mannoside compound 16 with a yield of 85%. Product 16: white solid; Rf (EP/AcOEt, 3:1) 0.3.

NMR $^1$H (CDCl$_3$, 400 MHz) δ (ppm): 7.85-7.79 (m, 3H, arom. H); 7.73-7.71 (m, 1H, arom. H); 7.55-7.30 (m, 13H, arom. H); 5.65 (s, 1H, H7); 4.99 (d, 1H, H9, $J_{H9-H9'}$=12.7 Hz); 4.96 (d, 1H, H9'); 4.94 (d, 1H, H8, $J_{H8-H8'}$=12.0 Hz); 4.65 (d, 1H, H8'); 4.52 (d, 1H, H1, $J_{H1-H2}$=1.0 Hz); 4.37 (dd, 1H, H6, $J_{H5-H6}$=5.1 Hz, $J_{H6-H6'}$=10.4 Hz); 4.21 (t, 1H, H4, $J_{H3-H4}=J_{H4-H5}$=9.4 Hz); 4.14 (dd, 1H, H2, $J_{H2-H3}$=3.3 Hz); 3.94 (t, 1H, H6', $J_{H5-H6'}$=10.4 Hz); 3.66 (dd, 1H, H3); 3.33 (ddd, 1H, H5).

NMR $^{13}$C (CDCl$_3$, 100 MHz) δ (ppm): 137.4, 136.5, 135.3, 133.1, 133.0 (5C, quat. arom. C); 129.2, 129.0, 128.6, 128.5, 128.3, 128.2, 128.1, 127.9, 127.6, 126.7, 126.2, 126.1, 125.9, 125.7 (arom. C); 101.6 (C7); 98.6 (C1; $^1J_{C1-H1}$=158 Hz); 78.4 (C4); 76.4 (C3); 72.4 (C9); 70.7 (C8); 70.0 (C2); 68.6 (C6); 66.9 (C5).

2.8/ benzyl 2-O-benzoyl-4,6-O-benzylidene-3-O-(2-methylnaphthyl)-β-D-glucopyranosyl-(1→3)-4,6-O-benzylidene-β-D-mannpyranoside (Product 17)

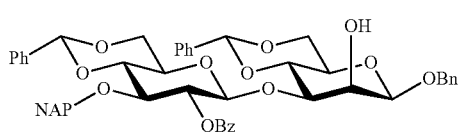

L-Selectride (1M solution in THF; 6 μL, 0.006 mmol) is added to the compound 14a/14b (5 mg, 0.006 mmol) in solu-tion in 1 mL of THF at −90° C. After stirring for 1 hour at low temperature, the medium is neutralized with acetic acid, diluted with 20 mL of dichloromethane and washed with a 10% aqueous hydrochloric acid solution, a saturated solution of sodium bicarbonate and a saturated aqueous solution of sodium chloride. After drying (MgSO$_4$) and concentration of the organic phase, 5 mg of the sought compound 17 (0.006 mmol) are obtained with a quantitative yield.

Product 17: white solid; Rf (EP/AcOEt, 2:1) 0.3.

NMR $^1$H (CDCl$_3$, 400 MHz) δ (ppm): 7.90-7.20 (m, 20H, arom. H); 5.55 (s, 1H, H7); 5.48 (s, 1H, H7); 5.35 (t, 1H, H2b, $J_{H1b-H2b}=J_{H2b-H3b}$=7.5 Hz); 4.94 (d, 1H, H8b, $J_{H8b-H8'b}$=12.2 Hz); 4.86 (d, 1H, H8'b); 4.81 (d, 1H, H8a, $J_{H8a-H8'a}$=11.9 Hz); 4.79 (d, 1H, H1b); 4.56 (d, 1H, H8'a); 4.37 (d, 1H, H1a, $J_{H1a-H2}$=0.9 Hz); 4.35-4.17 (m, 2H, H6a, H6b); 4.07 (t, 1H, H4b, $J_{H3b-H4b}$=9.3 Hz); 3.94 (t, 1H, H3a, $J_{H2a-H3a}=J_{H3a-H4a}$=9.0 Hz); 3.90-3.68 (m, 5H, H2a, H4a, H3b, H6'a, H6'b); 3.56-3.24 (m, 2H, H5a, H5b).

NMR $^{13}$C (CDCl$_3$, 100 MHz) δ (ppm): 166.3 (OCOPh); 137.2, 135.1, 133.2 (quat. arom. C); 129.9, 129.8, 129.7, 129.0, 128.5, 128.4, 128.3, 128.2, 128.1, 128.0, 127.9, 127.8, 127.5, 127.0, 126.3, 126.1, 126.0, 125.9, 125.8, 125.7 (arom. C); 101.2, 101.0 (C7); 100.4 (C1b); 98.3 (C1a); 81.8 (C3a); 80.9 (C4b); 78.4 (C4a); 77.7 (C3b); 74.0 (C2b); 73.7 (C8b); 70.5 (C8a); 69.4 (C2a); 68.6, 68.5 (C6a, C6b); 67.0 (C5a); 66.3 (C5b).

Example 3

Preparation of β-D-glucopyranosyl-(1→3)-β-D-glu-copyranosyl-(1→3)-β-D-glucopyranosyl-(1→3)-β-D-glucopyranosyl-(1→3)-β-D-glucopyranosyl-(1→3)-β-D-mannopyranose (Product A2)

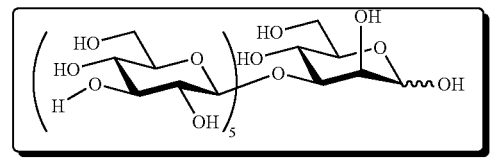

The desired product was prepared according to a protocol similar to that described for the product A1 by applying the successive stages [d], [c], [d], [c], then [e] to [i] to the product 9.

In this way the product A2 which is presented in the form of a white foam was obtained;

Rf (AcOEt/iPrOH/H$_2$O, 3:2:2) 0.2.

NMR $^1$H (D$_2$O, 400 MHz) δ (ppm): 5.19 (d, 1H, H1aα, $J_{H1a-H2a}$=2.2 Hz).

Other Signals:

NMR $^1$H (D$_2$O, 400 MHz) δ (ppm): 4.75 (d, 3H, 3H1, $J_{H1-H2}$=8.0 Hz); 4.71 (d, 2H, 2 H1, $J_{H1-H2}$=7.8 Hz); 3.93-3.81 (m, 8H, H3a, H4a, H6a, H6b, H6c, H6d, H6e, H6f); 3.80-3.63 (m, 11H, H2a, H3b, H3c, H3d, H3e, H6'a, H6'b, H6'c, H6'd, H6'e, H6'f); 3.55-3.40 (m, 11H, H2b, H2c, H2d, H2e, H3f, H4b, H4c, H4d, H4e, H5a, H5b, H5c, H5d, H5e, H5f); 3.36 (t, 1H, H4f, $J_{H3f-H4f}=J_{H4f-H5f}$=9.3 Hz); 3.31 (dd, 1H, H2f, $J_{H1f-H2f}$=8.0 Hz, $J_{H2f-H3f}$=9.3 Hz).

HRMS (ESI⁺): [M+Na]⁺ $C_{36}H_{62}NaO_{31}$: theoretical m/z: 1013.3173, measured m/z: 1013.3172; [M+K]⁺ $C_{36}H_{62}KO_{31}$: theoretical m/z: 1029.2912, measured m/z: 1029.2920.

Example 4

Preparation of β-D-glucopyranosyl-(1→3)-β-D-glucopyranosyl-(1→3)-mannitol (product B1) according to reaction diagram 1

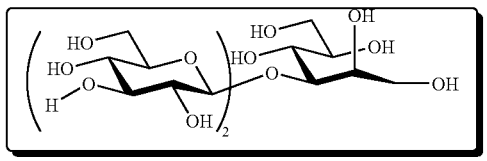

The deprotected trisaccharide A1 (25 mg, 0.049 mmol) is introduced into 10 mL of a methanol/water mixture (4:1; v/v). Sodium borohydride (19 mg, mmol) is added at ambient temperature and the medium is left under stirring for 10 days. The medium is then neutralized by the addition of a few drops of acetic acid then brought to dryness by coevaporation with a methanol/acetic acid mixture (9:1, v/v), then by coevaporation with methanol. After freeze-drying, the compound is purified by Sephadex gel G-10 permeation chromatography (eluent: water) and the fractions collected are freeze-dried in order to obtain the sought product B1 which is presented in the form of a white foam.

NMR ¹H (D₂O, 400 MHz) δ (ppm): 4.82 (d, 1H, H1c, $J_{H1c\text{-}H2c}$=8.0 Hz); 4.65 (d, 1H, H1b, $J_{H1b\text{-}H2b}$=8.1 Hz); 4.09-3.90 (m, 7H, H1a, H2a, H3a, H5a, H6a, H6b, H6c); 3.86-3.66 (m, 6H, H1'a, H4a, H6'a, H3b, H6'b, H6'c); 3.64-3.38 (m, 7H, H2b, H4b, H5b, H2c, H3c, H4c, H5c).

NMR ¹³C (D₂O, 100 MHz) δ (ppm): 103.1 (C1c); 102.5 (C1b); 84.4 (C3b); 77.3 (C3a); 76.3 (C5c); 75.8 (C3c); 75.5 (C5b); 73.7 (C2c); 73.4 (C2b); 70.9, 70.8 (2C, C2a, C5a); 69.9 (C4c); 69.6 (C4a); 68.8 (C4b); 63.4 (C6a); 62.6 (C1a); 61.2, 61.0 (2C, C6b, C6c).

Example 5

Preparation of the Product A1 According to Reaction Diagram 2

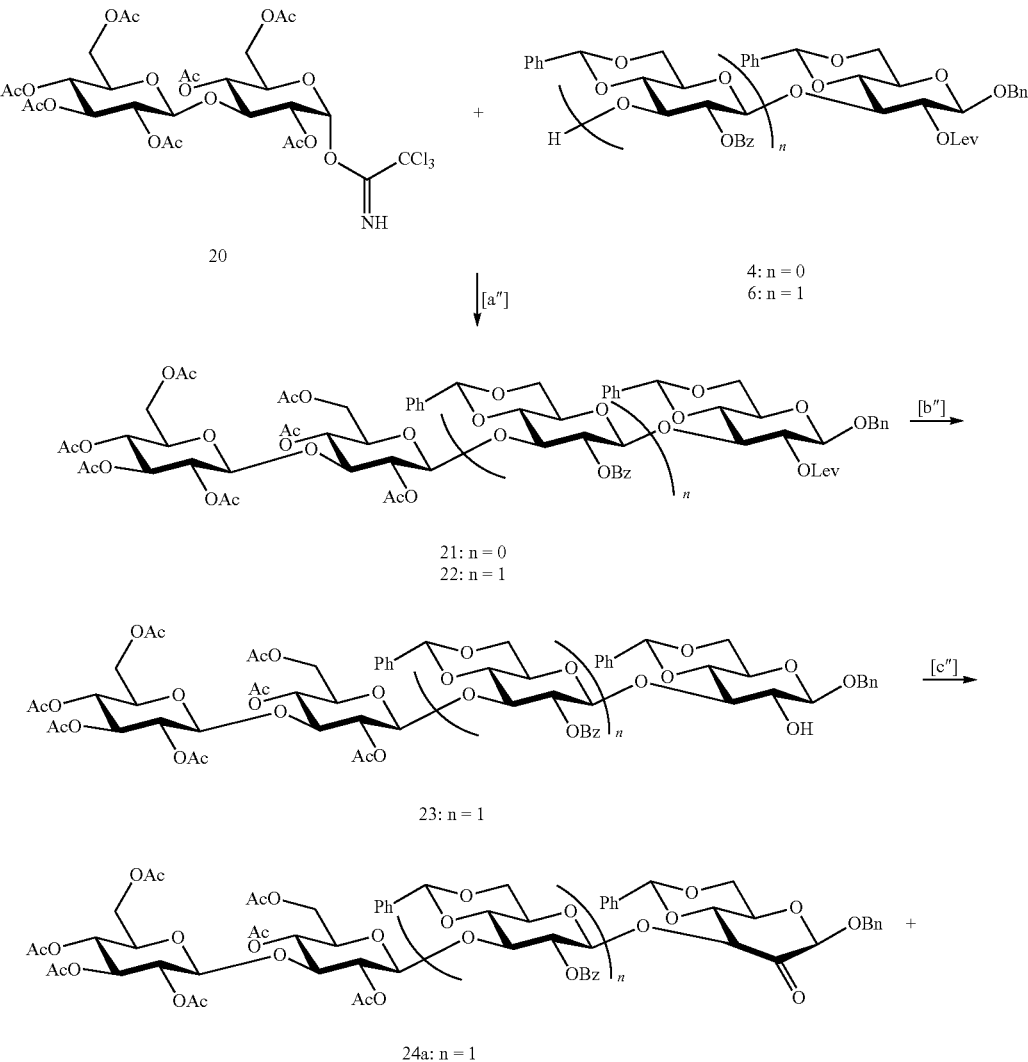

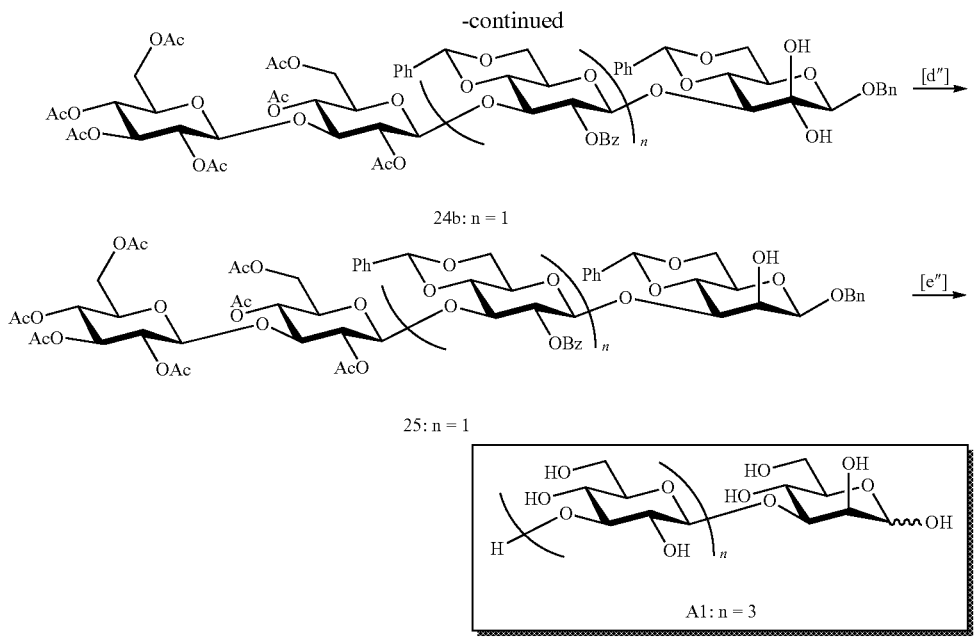

5.1/ Preparation of benzyl 2,3,4,6-tetra-O-acetyl-β-D-glucopyranosyl-(1→3)-2,4,6-tri-O-acetyl-β-D-glucopyranosyl-(1→3)-4,6-O-benzylidene-2-O-levulinoyl-β-D-glucopyranoside (Product 21)

The donor 20 [Blattner, R.; Furneaux, R. H.; Pakulski, Z. *Carbohydr. Res.* 2006, 341, 2115-2125.] (50 mg, 0.064 mmol) and the acceptor 4 (27 mg, 0.058 mmol) are introduced into anhydrous dichloromethane in a flask at −50° C., in the presence of a 4 Å molecular sieve. Trimethylsilyl triflate (0.53 µL, mmol) is then added and the mixture is stirred vigorously for 2 hours. Once the reaction has stopped, the medium is neutralized with triethylamine, filtered then concentrated. After purification by silica gel chromatography [petroleum ether/ethyl acetate (2:1; v/v)], 22 mg of the expected trisaccharide 21 are obtained with a yield of 35%.

Product 21: amorphous white solid; Rf (EP/AcOEt, 1:1) 0.2.

NMR $^1$H (CDCl$_3$, 400 MHz) δ (ppm): 7.46-7.43 (m, 2H, arom. H); 7.37-7.27 (m, 8H, arom. H); 5.53 (s, 1H, H7a); 5.10 (t, 1H, H3c, $J_{H2c-H3c}=J_{H3c-H4c}=9.3$ Hz); 5.04 (t, 1H, H4c, $J_{H4c-H5c}=9.3$ Hz); 5.02 (t, 1H, H2a, $J_{H1a-H2a}=7.7$ Hz, $J_{H2a-H3a}=9.5$ Hz); 4.95 (dd, 1H, H2b, $J_{H1b-H2b}=8.2$ Hz, $J_{H2b-H3b}=6.0$ Hz); 4.93 (dd, 1H, H4b, $J_{H3b-H4b}=7.3$ Hz, $J_{H4b-H5b}=9.7$ Hz); 4.87 (dd, 1H, H2c, $J_{H1c-H2c}=8.2$ Hz); 4.86 (d, 1H, H8a, $J_{H5a-H8'a}=12.2$ Hz); 4.62 (d, 1H, H1c); 4.57 (d, 1H, H8'a); 4.55 (d, 1H, H1b); 4.50 (d, 1H, H1a); 4.34 (dd, 1H, H6c, $J_{H5c-H6c}=2.0$ Hz, $J_{H6c-H6'c}=12.4$ Hz); 4.33 (dd, 1H, H6a, $J_{H5a-H6a}=4.6$ Hz, $J_{H6a-H6'a}=10.4$ Hz); 4.15-4.01 (m, 3H, H6b, H6'b, H6'c); 3.93 (t, 1H, H3a, $J_{H3a-H4a}=9.5$ Hz); 3.91 (dd, 1H, H3b); 3.79 (t, 1H, H6'a, $J_{H5a-H6'a}=10.4$ Hz); 3.69 (t, 1H, H4a, $J_{H4a-H5a}=9.5$ Hz); 3.69 (ddd, 1H, H5c, $J_{H5c-H6'c}=4.0$ Hz); 3.54 (ddd, 1H, H5b, $J_{H5b-H6b}=2.4$ Hz, $J_{H5b-H6'b}=4.0$ Hz); 3.40 (ddd, 1H, H5a); 2.87-2.80 (m, 1H, H10a); 2.70-2.62 (m, 2H, H10'a, H11a); 2.50-2.42 (m, 1H, H11'a); 2.20 (s, 3H, H13a); 2.04, 1.99, 1.97, 1.96, 1.94 (6 s, 21H, OCOCH$_3$).

NMR $^{13}$C (CDCl$_3$, 100 MHz) δ (ppm): 206.1 (C12a); 171.0 (C9a); 170.8, 170.5, 170.4, 169.3, 169.2, 169.1 (7C, OCOCH$_3$); 137.0, 136.8 (2C, quat. arom. C); 129.0, 128.5, 128.4, 128.3, 128.1, 128.0, 127.9, 127.8, 125.9 (arom. C); 100.9 (C7a); 100.7 (C1c); 100.1 (C1b); 99.8 (C1a); 78.7 (C3b); 78.6 (C4a); 77.7 (C3a); 73.8 (C2a); 73.0 (C3c); 72.6 (C2b); 71.5 (C5b); 71.4 (C5c); 70.9 (C2c); 70.7 (C8a); 68.5 (C6a); 68.1 (C4c); 68.0 (C4b); 66.5 (C5a); 62.2 (C6b); 61.6 (C6c); 37.6 (C11a); 30.1 (C13a); 27.6 (C10a); 21.0, 20.9, 20.7, 20.6, 20.5, 20.4 (7C, OCOCH$_3$).

5.2/ Preparation of benzyl 2,3,4,6-tetra-O-acetyl-β-D-glucopyranosyl-(1→3)-2,4,6-tri-O-acetyl-β-D-glucopyranosyl-(1→3)-2-O-benzoyl-4,6-O-benzylidene-β-D-glucopyranosyl-(1→3)-4,6-O-benzylidene-2-O-levulinoyl-β-D-glucopyranoside (Product 22)

The disaccharide donor 37 (106 mg, 0.136 mmol) and the acceptor 71 (100 mg, 0.123 mmol) are introduced into anhydrous dichloromethane in a flask at −50° C., in the presence of a 4 Å molecular sieve. Trimethylsilyl triflate (1.1 µL, 0.006 mmol) is added and the reaction medium is stirred for 60 minutes. The medium is neutralized with triethylamine, filtered then concentrated. After purification by silica gel chromatography [petroleum ether/ethyl acetate (1:1; v/v)], 146 mg of the tetrasaccharide orthoester are obtained with a yield of 83%. The compound thus obtained is directly involved in an intramolecular rearrangement reaction in the presence of trimethylsilyl triflate (2.5 µL, 0.014 mmol) in dichloromethane at 0° C. After stirring for 3 hours, the medium is neutralized with triethylamine, then concentrated. After purification by silica gel chromatography [petroleum ether/ethyl acetate (1:1; v/v)], 101 mg of the expected product 22 are obtained with a yield of 69%.

Product 22: white solid; MP (° C.) 119; Rf (EP/AcOEt, 1:1) 0.3.

NMR $^1$H (CDCl$_3$, 400 MHz) δ (ppm): 8.02-7.99 (m, 2H, arom. H); 7.61-7.12 (m, 18H, arom. H); 5.59 (s, 1H, H7b); 4.83 (d, 1H, H8a, $J_{H8a-H8'a}=12.2$ Hz); 4.57 (s, 1H, H7a); 4.56 (d, 1H, H8'a); 2.73-2.65 (m, 1H, H10a); 2.63-2.51 (m, 1H, H10'a); 2.48-2.40 (m, 1H, H11a); 2.35-2.26 (m, 1H, H1b); 2.08 (s, 3H, H13a); 2.08, 2.04, 2.01, 2.00, 1.97, 1.94 (7s, 21H, OCOCH$_3$) and Table 4a.

NMR $^{13}$C (CDCl$_3$, 100 MHz) δ (ppm): 206.0 (C12a); 171.2 (C9a); 170.8, 170.5, 170.3, 169.4, 169.3, 169.1, 168.7 (6C, OCOCH$_3$); 165.0 (OCOPh); 137.3, 136.9, 136.7 (3C, quat. arom. C); 133.3, 129.8, 129.7 (arom. C); 129.6 (quat. arom. C); 129.5, 128.5, 128.4, 128.3, 128.2, 127.9, 127.8, 126.5, 126.0, 125.8 (arom. C); 102.2 (C7b); 99.7 (C7a); 70.7 (C8a); 37.6 (C11a); 29.4 (C13a); 27.7 (C10a); 21.0, 20.9, 20.6, 20.5, 20.4, 20.3 (7C, OCOCH$_3$) and Table 4b.

HRMS (ESI$^+$): [M+Na]$^+$ C$_{71}$H$_{80}$NaO$_{31}$: theoretical m/z: 1451.4581, measured m/z: 1451.4579; [M+K]$^+$ C$_{71}$H$_{80}$KO$_{31}$: theoretical m/z: 1467.4321, measured m/z: 1467.4346.

5.3/ benzyl 2,3,4,6-tetra-O-acetyl-β-D-glucopyranosyl-(1→3)-2,4,6-tri-O-acetyl-β-D-glucopyranosyl-(1→3)-2-O-benzoyl-4,6-O-benzylidene-β-D-glucopyranosyl-(1→3)-4,6-O-benzylidene-β-D-glucopyranoside (Product 23)

The tetrasaccharide 22 (430 mg, 0.301 mmol) is put into solution in 6 mL of pyridine then 6 mL of a 1M solution of hydrazine in a pyridine/acetic acid mixture (3:2, v/v) is added dropwise. After stirring for 3 hours, the reaction is stopped by the addition of 1.7 mL of 2,4-pentane-dione and concentrated under reduced pressure. The medium is taken up in 50 mL of dichloromethane and washed with a 10% hydrochloric acid solution, a saturated aqueous solution of sodium bicarbonate and a saturated aqueous solution of sodium chloride. After drying (MgSO$_4$) and concentration, the product is purified by silica gel chromatography [petroleum ether/ethyl acetate (1:1; v/v)] in order to produce 260 mg of the deprotected compound 23 with a yield of 65%.

Product 23: white solid; MP (° C.) 136; Rf (EP/AcOEt, 1:1) 0.3; [α]$_D^{20}$ −29.6 (c=1.0, CH$_2$Cl$_2$).

NMR $^1$H (CDCl$_3$, 400 MHz) δ (ppm): 8.11-8.09 (dd, 2H, arom. H); 7.67-7.17 (m, 18H, arom. H); 5.61 (s, 1H, H7); 5.08 (s, 1H, H7); 4.92 (d, 1H, H8a, J$_{H8a-H'a}$=11.7 Hz); 4.61 (d, 1H, H8'a); 2.09, 2.03, 2.01, 2.00, 1.99 (7s, 21H, OCOCH$_3$) and Table 4a.

NMR $^{13}$C (CDCl$_3$, 100 MHz) δ (ppm): 170.8, 170.5, 170.2, 169.3, 169.2, 169.0, 168.6 (7C, OCOCH$_3$); 165.1 (OCOPh); 137.1, 137.0, 136.5 (3C, quat. arom. C); 133.3 (arom. C); 129.5 (quat. arom. C); 129.7, 129.1, 128.9, 128.8, 128.7, 128.5, 128.4, 128.2, 128.1, 128.0, 127.9, 127.8, 126.0, 125.8, 125.2 (arom. C); 101.4 (C7); 100.4 (C7); 71.3 (C8a); 20.6, 20.5, 20.4, 20.3, 20.2 (7C, OCOCH$_3$) and Table 4b.

5.4/ Preparation of benzyl 2,3,4,6-tetra-O-acetyl-β-D-glucopyranosyl-(1→3)-2,4,6-tri-O-acetyl-β-D-glucopyranosyl-(1→3)-2-O-benzoyl-4,6-O-benzylidene-β-D-glucopyranosyl-(1→3)-4,6-O-benzylidene-β-D-glucopyranos-2-uloside (Product 24a) and of benzyl 2,3,4,6-tetra-O-acetyl-β-D-glucopyranosyl-(1→3)-2,4,6-tri-O-acetyl-β-D-glucopyranosyl-(1→3)-2-O-benzoyl-4,6-O-benzylidene-β-D-glucopyranosyl-(1→3)-4,6-O-benzylidene-2-C-hydroxyl-β-D-glucopyranoside (Product 24b)

Pyridine (0.5 mL) and Dess-Martin periodinane (2.6 mL of a 15% solution) are added to a solution of the product 23 (260 mg, 0.195 mmol) in 5 mL of anhydrous dichloromethane. After 24 hours at ambient temperature, ethyl ether is added to the medium. The resultant precipitate is filtered on celite and the filtrate concentrated under reduced pressure. The residue is finally purified by silica gel chromatography [petroleum ether/ethyl acetate (1:1; v/v)], in order to produce 208 mg of the oxidized product 24a (yield=80%) in mixture (1:1) with its hydrated form 24b.

24a/24b: white solid; Rf (EP/AcOEt, 1:1) 0.2.

Product 24a: NMR $^1$H (CDCl$_3$, 400 MHz) δ (ppm): Characteristic signals 5.25 (s, 1H, H1a).

NMR $^{13}$C (CDCl$_3$, 100 MHz) δ (ppm): Characteristic signals 196.6 (C2a); 96.8 (C1a); 70.6 (C8a).

Product 24b: NMR $^1$H (CDCl$_3$, 400 MHz) δ (ppm): Characteristic signals 4.87 (s, 1H, H1a).

NMR $^{13}$C (CDCl$_3$, 100 MHz) δ (ppm): Characteristic signals 98.8 (C1a); 93.7 (C2a); 71.4 (C8a).

Other Signals (24a/24b):

NMR $^1$H (CDCl$_3$, 400 MHz) δ (ppm): 8.08-8.03 (m, 2H, arom. H); 7.67-7.45 (m, 8H, arom. H); 7.40-7.10 (m, 30H, arom. H); 5.65 (s, 1H, H7); 5.59 (s, 1H, H7); 5.26-5.18 (m, 2H, 2H2b); 5.14-4.80 (m, 14H, H2c, 2H2d, 2H3d, 2H4a, 2H4b, 2H8a, 2H1); 4.73 (d, 1H, H8a, J$_{H8a-H8'a}$=11.9 Hz); 4.66-4.48 (m, 6H, H3a, H8'a, 2H1, H6, H7); 4.42-4.26 (m, 6H, H3a, H1, H7, 3H6); 4.20-3.40 (m, 28H, 2H3b, 2H3c, 2H4c, 2H4d, 2H5a, 2H5b, 2H5c, 2H5d, 2H6'a, 2H6'b, 2H6'c, 2H6'd, 4H6); 2.08, 2.06, 2.04, 2.01, 2.00, 1.99, 1.98, 1.97, 1.96, 1.95 (14 s, 42H, OCOCH$_3$).

NMR $^{13}$C (CDCl$_3$, 100 MHz) δ (ppm): 170.8, 170.5, 170.3, 169.4, 169.3, 169.2, 169.1, 168.8 (10C, OCOCH$_3$); 165.3 (2C, OCOPh); 137.1, 137.0, 136.6, 136.0, 135.6 (6C, quat. arom. C); 133.7, 133.6, 129.9, 129.4, 129.3, 129.2, 129.1, 128.8, 128.7, 128.6, 128.5, 128.4, 128.3, 128.2, 127.9, 127.7, 126.4, 126.2, 125.9, 125.8 (arom. C, 2 quat. arom. C); 101.8, 101.6, 100.4, 100.2 (4C, C7); 100.9, 100.8, 100.6, 99.2, 98.8, 96.8 (8C, C1); 80.6, 79.8, 79.3, 79.0, 78.7, 78.1, 77.8, 77.4, 77.2, 77.1 (10C, C3a, C3b, C3c, C4a, C4b); 74.8 (2C, C2b); 73.3, 73.0, 72.8, 72.3 (4C, C2c, C3d); 71.6, 71.5 (4C, C5c, C5d); 71.0, 70.8 (2C, C2d); 68.7, 68.6, 68.4 (4C, C6a, C6b); 68.0, 67.9 (4C, C4c, C4d); 67.0, 66.8 (2C, C5a); 65.6, 65.1 (2C, C5b); 62.0 (2C, C6d); 61.6 (2C, C6c); 21.1, 20.7, 20.6, 20.5, 20.4, 20.3 (14C, OCOCH$_3$).

5.5/ benzyl 2,3,4,6-tetra-O-acetyl-β-D-glucopyranosyl-(1→3)-2,4,6-tri-O-acetyl-β-D-glucopyranosyl-(1→3)-2-O-benzoyl-4,6-O-benzylidene-β-D-glucopyranosyl-(1→3)-4,6-O-benzylidene-β-D-mannopyranoside (Product 25)

L-Selectride (1M solution in THF; 150 μL, 0.150 mmol) is added to the product 24a/24b (66 mg, 0.050 mmol) in solution in a dichloromethane/THF mixture at −90° C. After stirring for 2 hours at low temperature, the medium is neutralized by the addition of acetic acid, diluted with 20 mL of dichloromethane and washed with a saturated aqueous solution of hydrochloric acid, a saturated aqueous solution of sodium bicarbonate and water. After drying over MgSO$_4$ and concentration, the medium is purified by silica gel chromatography [dichloromethane/methanol (98:2; v/v)], in order to produce the desired reduced product 25 (66 mg, 0.050 mmol) with a quantitative yield.

Product 25: white solid; Rf (CH$_2$Cl$_2$/MeOH, 98:2) 0.2.

NMR $^1$H (CDCl$_3$, 400 MHz) δ (ppm): 8.08-8.03 (m, 2H, arom. H); 7.67-7.10 (m, 18H, arom. H); 5.62 (s, 1H, H7); 5.22 (m, 1H, H2b, J$_{H1b-H2b}$=J$_{H2b-H3b}$=5.1 Hz); 5.04 (t, 1H, H3d, J$_{H2d-H3d}$=J$_{H3d-H4d}$=8.0 Hz); 5.03-4.91 (m, 5H, H1b, H2c, H4c, H4d, H7); 4.90 (d, J$_{H1c-H2c}$=8.0 Hz); 4.63 (d, 1H, H8'a); 4.47 (d, 1H, H1a, J$_{H1a-H2a}$<1.0 Hz); 4.44 (d, 1H, H1d); 4.39-4.31 (m, 2H, H6a, H6c); 4.18-3.94 (m, 8H, H2a, H3b, H4a, H4b, H6b, H6d, H6'c, H6'd); 3.93-3.84 (m, 2H, H3a, H6'a); 3.75 (t, 1H, H3c, J$_{H2c-H3c}$=J$_{H3-H4c}$=9.3 Hz); 3.64 (t, 1H, H6'b, J$_{H5b-H6'b}$=J$_{H6b-H6'b}$=10.0 Hz); 3.62-3.52 (m, 3H, H5b, H5c, H5d); 3.34 (dt, 1H, H5a, $J_{H4a-H5a}=J_{H5a-H6'a}=9.8$ Hz, $J_{H5a-H6a}=4.6$ Hz); 2.05, 2.00, 1.97, 1.95, 1.94 (7s, 21H, OCOCH$_3$).

NMR $^{13}$C (CDCl$_3$, 100 MHz) δ (ppm): 170.8, 170.4, 170.3, 169.3, 169.2, 169.1, 168.9 (7C, OCOCH$_3$); 165.0 (OCOPh); 137.2, 137.1, 136.4, 129.2 (4C, quat. arom. C); 133.6, 129.7, 129.0, 128.8, 128.6, 128.5, 128.4, 128.3, 128.2, 128.0, 127.8, 126.1, 125.8 (arom. C); 101.7, (C7); 100.7 (C1d); 100.5 (C7); 99.7 (C1c); 98.3 (C1a); 97.3 (C1b); 78.7 (C3c); 78.4 (C3b); 77.5 (C4b); 76.3 (C4a); 75.7 (C3a); 74.2 (C2b); 72.9 (C3d); 72.4 (C2c); 71.5 (2C, C5c, C5d); 70.8 (C2d); 70.6 (C7a); 68.7 (C2a); 68.6 (C6b); 68.5 (C6a); 68.1 (C4c); 67.9 (C4d); 67.2 (C5a); 65.9 (C5b); 61.9 (C6d); 61.5 (C6c); 20.7, 20.6, 20.5, 20.4 (7C, OCOCH$_3$).

5.6/ Preparation of the product A1

Compound 25 (60 mg, 0.045 mmol) is dissolved in a dichloromethane/methanol mixture (2:1, v/v; 10 mL) then 2 equivalents of sodium methylate (0.1M in MeOH, 0.9 mL, 0.090 mmol) are added. After stirring for 6 hours at ambient temperature, the medium is neutralized by the addition of Amberlite IR120-H$^+$resin, filtered then concentrated under reduced pressure. The residue thus obtained is then dissolved in 10 mL of an ethyl acetate/methanol/dichloromethane mixture (2:2:1; v/v/v). After the addition of palladium acetate (60 mg, 0.267 mmol), the medium is stirred vigorously at ambient temperature under a hydrogen atmosphere for 7 days. After filtration on celite, the hydro-organic phase is extracted with dichloromethane, then brought to dryness by azeotropic coevaporation with absolute ethanol. The product A1 (30 mg) is then isolated with a quantitative yield in the last three stages.

Example 6

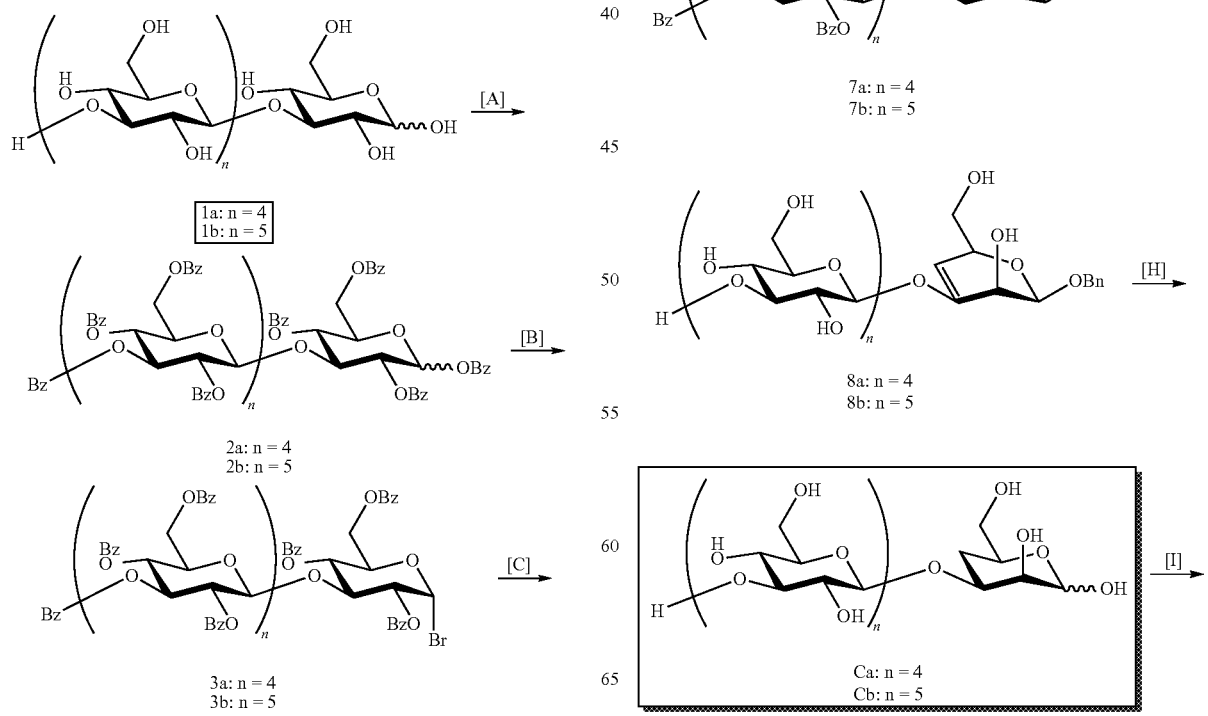

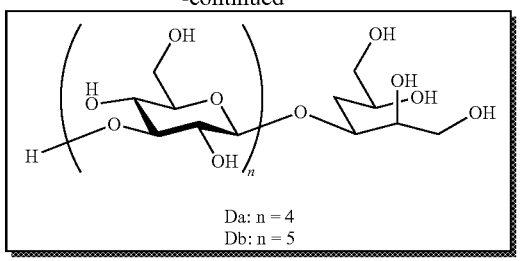

Da: n = 4
Db: n = 5

The product 1a is obtained as described in the Patent Application FR2804684

6.1/ Preparation of 2,3,4,6-tetra-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-1,2,4,6-tetra-O-benzoyl-(α,β)-D-glucopyranose (Product 2a)

The oligosaccharide 1a (150 mg, 0.181 mmol) is dissolved in pyridine (15 mL). The reaction medium is then cooled down to 0° C. then benzoyl chloride (4.2 mL, 36 mmol) is added. After stirring for 2 days at ambient temperature, the medium is evaporated, dissolved in dichloromethane then washed with a 10% aqueous hydrochloric acid solution, a saturated solution of sodium bicarbonate and a saturated solution of sodium chloride until neutrality is reached. The organic phase is then dried over MgSO₄ and evaporated. The residue is purified by silica gel chromatography [petroleum ether/ethyl acetate (3:2; v/v)] in order to produce the perbenzoylated derivative 2a in the form of a mixture of anomers α/β:1/1 with a yield of 94% (444 mg, 0.170 mmol).
Product 2a: colourless oil; Rf (EP/AcOEt, 1:1) 0.4.
NMR $^1$H (CDCl$_3$, 400 MHz) δ (ppm): Characteristic signals for 2a☐ 6.65 (d, 1H, H1a, $J_{H1a-H2a}$=3.6 Hz); 5.47 (t, 1H, H4a, $J_{H3a-H4a}$=$J_{H4a-H5a}$=9.4 Hz); 4.64 (t, 1H, H3a, $J_{H2a-3a}$=9.4 Hz). Characteristic signals for 2a☐ 6.07 (d, 1H, H1a, $J_{H1a-H2a}$=7.1 Hz); 5.57 (t, 1H, H4a, $J_{H3a-H4a}$=$J_{H4a-H5a}$=8.9 Hz); 4.25 (dt, 1H, H5a, $J_{H5a-H6a}$=4.3 Hz, $J_{H5a-H6'a}$=8.9 Hz).
NMR $^{13}$C (CDCl$_3$, 100 MHz) δ (ppm): Characteristic signals for 2a☐ 87.7 (C1a); 76.3 (C3a); 72.4 (C2a); 70.3 (C5a); 67.6 (C4a). Characteristic signals for 2a☐ 89.7 (C1a); 78.4 (C3a); 72.4 (2C, C2a, C5a); 67.6 (C4a); 62.0 (C6a).
Other Signals:
NMR $^1$H (CDCl$_3$, 400 MHz) δ (ppm): 8.08-7.92 (m, 68H, arom. H); 7.61-7.09 (m, 102H, arom. H); 5.45-5.37 (m, 3H, H2aβ, H3e); 5.26-5.18 (m, 5H, H2aα, H2e, H4e); 5.11-4.83 (m, 14H, H1b, H2b, H4b, H2c, H4c, H2d, H4d); 4.61-4.35 (m, 10H, H3aβ, H5aα, H6aβ, H6'aβ, H1e, H1d, H1e); 4.20-3.86 (m, 26H, H6aα, H6'aα, H3b, H6b, H6'b, H3c, H6c, H6'c, H3d, H6d, H6'd, H5e, H6e, H6'e); 3.80-3.65 (m, 6H, H5b, H5c, H5d).
NMR $^{13}$C (CDCl$_3$, 100 MHz) δ (ppm): 166.0, 165.9, 165.8, 165.7, 165.6, 165.4, 164.9, 164.8, 164.7, 164.6, 164.5, 164.3, 164.1, 163.8, 163.6, 163.5 (OCOPh); 133.3, 132.7, 130.0, 129.3, 129.2, 129.1, 129.0, 128.9, 128.7 (quat. arom. C); 133.8, 133.6, 133.4, 133.2, 133.1, 133.0, 132.9, 132.8, 132.6, 129.9, 129.7, 129.6, 129.5, 129.4, 128.6, 128.5, 128.4, 128.3, 128.2, 128.1, 128.0, 127.9 (arom. C); 101.4, 101.3, 101.0, 100.8, 100.7 (8C, C1b, C1c, C1d, C1e); 78.1, 77.5, 77.4, 77.2 (6C, C3b, C3c, C3d); 73.4, 73.3, 73.2 (4C, 2C2); 72.7, 72.6, 72.5, 72.4 (4C, C3e, C2); 71.8, 71.7, 71.6, 71.5 (8C, C5b, C5c, C5d, C5e); 71.3 (2C, C2e); 70.3, 70.2 (6C, C4b, C4c, C4d); 69.8 (2C, C4e); 63.5, 63.4, 63.1, 62.7 (9C, C6aα, C6b, C6c).

6.2/ Preparation of 2,3,4,6-tetra-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl-α-D-glucopyranosyl bromide (Product 3a)

The perbenzoylated oligosaccharide 2a (444 mg, 0.170 mmol) is put into solution in dichloromethane (10 mL), then 33% by wt hydrobromic acid in acetic acid (0.6 mL, 3.417 mmol) was added at 0° C. After stirring for 3.5 hours, the medium is diluted with dichloromethane then washed with a saturated aqueous solution of sodium bicarbonate. The organic phase is then dried over MgSO₄ and concentrated under reduced pressure in order to produce 435 mg of brominated compound 3a in quantitative manner.
Product 3a: colourless oil.
NMR $^1$H (CDCl$_3$, 400 MHz) δ (ppm): Characteristic signals 6.55 (d, 1H, H1a, $J_{H1a-H2a}$=4.1 Hz); 5.35 (t, 1H, H4a, $J_{H3a-H4a}$=$J_{H4a-H5a}$=9.9 Hz); 4.24 (dd, 1H, H6'a, $J_{H5a-H6'a}$=4.6 Hz, $J_{H6a-H6'a}$=12.4 Hz).
NMR $^{13}$C (CDCl$_3$, 100 MHz) δ (ppm): Characteristic signals 87.7 (C1a); 76.3 (C3a); 73.4 (C2a); 72.6 (C5a); 67.6 (C4a); 62.0 (C6a).
Other Signals:
NMR $^1$H (CDCl$_3$, 400 MHz) δ (ppm): 8.92-7.61 (m, 22H, arom. H); 7.48-6.93 (m, 58H, arom. H); 5.27 (t, 1H, H3e, $J_{H2e-H3e}$=$J_{H3e-H4e}$=9.7 Hz); 5.09 (dd, 1H, H2e, $J_{H1e-H2e}$=7.9 Hz); 5.08 (t, 1H, H4e, $J_{H4e-H5e}$=9.7 Hz); 4.93-4.86 (m, 3H, 2H2, H4); 4.80-4.70 (m, 4H, H2a, H1, 2H4); 4.50-4.33 (m, 6H, H3a, H5a, H6a, H1e, 2H1); 4.08-3.94 (m, 3H, H5e, H3, H6); 3.87-3.70 (m, 9H, 2H3, 7H6); 3.65-3.53 (m, 3H, H5b, H5c, H5d).
NMR $^{13}$C (CDCl$_3$, 100 MHz) δ (ppm): 165.9, 165.8, 165.7, 165.4, 164.9, 164.8, 164.7, 164.6, 164.5, 164.3, 163.8, 163.5 (16C, OCOPh); 133.8, 133.4, 133.2, 133.1, 133.0, 132.9, 132.8, 132.6, 129.9, 129.7, 129.6, 129.5, 129.4, 129.3, 129.2, 129.0, 128.7, 128.6, 128.5, 128.4, 128.3, 128.2, 128.1, 128.0, 127.9 (arom. C); 101.3, 101.0, 100.8, 100.7 (4C, C1b, C1c, C1d, C1e); 78.4, 78.1, 77.4 (3C, C3b, C3c, C3d); 73.3, 73.2, 72.7 (3C, C2b, C2c, C2d); 72.5 (C3e); 71.8, 71.7, 71.6, 71.5 (4C, C5b, C5c, C5d, C5e); 71.3 (C2e); 70.2 (3C, C4b, C4c, C4d); 69.8 (C4e); 63.4, 63.1 (4C, C6b, C6c, C6d, C6e).

6.3/ Preparation of 2,3,4,6-tetra-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl-2-D-gluhex-1-enopyranose (Product 4a)

The crude product previously obtained (3a: 435 mg, 0.170 mmol) is dissolved in dichloromethane (10 mL) then 1,8-diazabicyclo[5,4,0]undec-7-ene (40 μL, 0.270 mmol) is added. After stirring for 5.5 hours at ambient temperature, the medium is diluted with dichloromethane, washed with a 10% aqueous hydrochloric acid solution, with a saturated aqueous solution of sodium bicarbonate, then with a saturated aqueous solution of sodium chloride. The organic phase is dried (MgSO₄), evaporated and the sought product is obtained after purification on silica gel [petroleum ether/ethyl acetate (3:2; v/v)]. The target compound 4a (343 mg) is then isolated with a yield of 81%.

Product 4a: white solid; Rf (EP/AcOEt, 3:2) 0.4.

NMR $^1$H (CDCl$_3$, 400 MHz) δ (ppm): Characteristic signals 6.63 (s, 1H, H1a); 5.77 (d, 1H, H3a, $J_{H3a-H4a}$=3.3 Hz); 4.73 (dd, 1H, H6a, $J_{H5a-H6a}$=9.0 Hz, $J_{H6a-H6'a}$=12.6 Hz); 4.40 (dd, 1H, H6'a, $J_{H5a-H6'a}$=3.1 Hz).

NMR $^{13}$C (CDCl$_3$, 100 MHz) δ (ppm): Characteristic signals 138.2 (C1a); 74.1 (C5a); 72.3 (C4a); 68.7 (C3a); 61.6 (C6a).

Other Signals:

NMR $^1$H (CDCl$_3$, 400 MHz) δ (ppm): 8.14-7.70 (m, 26H, arom. H); 7.63-7.03 (m, 54H, arom. H); 5.38 (t, 1H, H3 e, $J_{H2e-H3e}$=$J_{H3e-H4e}$=9.5 Hz); 5.21 (dd, 1H, H2e, $J_{H1e-H2e}$=8.0 Hz); 5.20 (t, 1H, $J_{H4e-H5e}$=9.5 Hz); 5.17 (t, 1H, H2b, $J_{H1-H2b}$=$J_{H2b-H3b}$=8.8 Hz); 5.12 (t, 1H, H4b, $J_{H3b-H4b}$=$J_{H4b-H5b}$=10.5 Hz); 5.05-4.97 (m, 2H, H4c, H2d); 4.94 (d, 1H, H1b); 4.94-4.88 (m, 2H, H2c, H4d); 4.71 (d, 1H, H1e, $J_{H1c-H2c}$=6.7 Hz); 4.59 (d, 1H, H1e, $J_{H1e-H2e}$=8.0 Hz); 4.58-4.53 (m, 3H, H4a, H5a, H1d); 4.46 (dd, 1H, H6b, $J_{H5b-H6b}$=3.1 Hz, $J_{H6b-H6'b}$=12.2 Hz); 4.31 (dd, 1H, H3b); 4.25 (dd, 1H, H6'b, $J_{H5b-H6'b}$=6.6 Hz); 4.15-3.87 (m, 9H, H5b, H3c, H6c, H6'c, H3d, H6d, H6'd, H6e, H6'e); 3.80 (dt, 1H, H5d, $J_{H5d-H6d}$=4.9 Hz, $J_{H5d-H6'd}$=9.3 Hz); 3.76-3.68 (m, 2H, H5c, H5e).

NMR $^{13}$C (CDCl$_3$, 100 MHz) δ (ppm): 165.9, 165.8, 165.7, 165.4, 165.3, 165.1, 165.0, 164.8, 164.7, 164.6, 163.9, 163.7 (16C, OCOPh); 133.3, 133.2, 133.0, 132.9, 132.7, 130.1, 130.0, 129.9, 129.7, 129.6, 129.5, 129.3, 129.2, 129.1, 128.9, 128.7, 128.6, 128.5, 128.4, 128.3, 128.2, 128.1, 128.0, 127.8 (C2a, arom. C); 101.2 (C1b); 100.9 (C1c); 100.8 (C1e); 100.7 (C1d); 78.2, 78.0, 77.7 (3C, C3b, C3c, C3d); 73.5 (C2c); 73.2 (C2b); 72.8 (C2d); 72.7 (C5b); 72.6 (C3e); 72.1 (C5d); 71.6 (2C, C5c, C5e); 71.3 (C2e); 70.3 (C4c); 70.0 (C4d); 69.9, 69.8 (2C, C4b, C4e); 63.5, 63.4, 63.2 (3C, C6c, C6d, C6e); 63.1 (C6b).

6.5/ Preparation of 2,3,4,6-tetra-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-4,6-di-O-benzoyl-α-D-glucopyranos-2-ulosyl bromide (Product 5a)

Methanol (1.6 µL, 0.040 mmol) is added to the previously described compound 5a (48 mg, 0.019 mmol) in solution in dichloromethane (0.5 mL). After stirring for 10 minutes at ambient temperature, N-bromosuccinimide (10.8 mg, 0.060 mmol) is added at 0° C. Once the reaction has stopped, the medium is diluted with dichloromethane then washed with an iced saturated aqueous solution of sodium thiosulphate and with iced water. The organic phase is then dried over MgSO$_4$ and concentrated under reduced pressure in order to produce 5a with a quantitative yield (47 mg, 0.019 mmol).

Product 5a: colourless oil.

NMR $^1$H (CDCl$_3$, 400 MHz) δ (ppm): Characteristic signals 6.25 (s, 1H, H1a); 5.44 (t, 1H, H4a, $J_{H3a-H4a}$=$J_{H4a-H5a}$=10.1 Hz); 5.17 (d, 1H, H3a).

NMR $^{13}$C (CDCl$_3$, 100 MHz) δ (ppm): Characteristic signals 191.5 (C2a); 83.8 (C1a); 76.3 (C3a); 72.6 (C5a); 69.0 (C4a); 61.7 (C6a).

Other Signals:

NMR $^1$H (CDCl$_3$, 400 MHz) δ (ppm): 8.06-7.71 (m, 20H, arom. H); 7.61-7.12 (m, 55H, arom. H); 5.39 (t, 1H, H3e, $J_{H2e-H3e}$=$J_{H3e-H4e}$=9.5 Hz); 5.22 (dd, 1H, H2e, $J_{H1e-H2e}$=8.0 Hz); 5.21 (t, 1H, H4e, $J_{H4e-H5e}$=9.5 Hz); 5.10 (dd, 1H, H2b, $J_{H1b-H2b}$=8.2 Hz, $J_{H2b-H3b}$=9.3 Hz); 5.06-4.98 (m, 4H, H1b, H4b, H4c, H2d); 4.89 (t, 1H, H4d, $J_{H3d-H4d}$=$J_{H4d-H5d}$=9.5 Hz); 4.88 (dd, 1H, H2e, $J_{H1c-H2c}$=7.7 Hz, $J_{H2c-H3c}$=8.6 Hz); 4.74 (d, 1H, H1c, $J_{H1c-H2c}$=8.2 Hz); 4.69 (d, 1H, H1e); 4.66-4.55 (m, 3H, H5a, H6a, H1d); 4.39-4.26 (m, 2H, H3b, H6); 4.24-4.10 (m, 3H, 3H6); 4.05-3.86 (m, 8H, H5b, H3e, H3d, 5H6); 3.82-3.70 (m, 3H, H5c, H5d, H5e).

NMR $^{13}$C (CDCl$_3$, 100 MHz) δ (ppm): 167.1, 165.9, 165.8, 165.7, 165.4, 164.9, 164.7, 164.6, 164.3, 164.1, 163.9, 163.6 (15C, OCOPh); 133.6, 133.3, 133.2, 133.1, 133.0, 132.9, 132.8, 132.7, 130.3, 130.0, 129.8, 129.7, 129.6, 129.5, 129.4, 129.3, 129.2, 129.1, 129.0, 128.8, 128.7, 128.6, 128.5, 128.4, 128.3, 128.2, 128.1, 128.0, 127.8, 127.6 (arom. C); 101.0, 100.9, 100.7, 100.6 (4C, C1b, C1c, C1d, C1e); 78.2, 78.0, 77.7 (3C, C3b, C3c, C3d); 73.6, 73.1, 72.8 (3C, C2b, C2e, C2d); 72.6 (C3e); 71.9, 71.6 (4C, C5b, C5c, C5d, C5e); 71.3 (C2e); 70.1, 69.9, 69.8 (4C, C4b, C4c, C4d, C4e); 63.5, 63.4, 63.1 (4C, C6b, C6c, C6d, C6e).

6.6/ Preparation of benzyl 2,3,4,6-tetra-O-benzoyl*D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-6-O-benzoyl-4-deoxy-β-D-gluco-hex-3-enopyranos-2-uloside (Product 6a)

Procedure 1:

Benzyl alcohol (7 µL, 0.068 mmol) and ulosyl bromide 5a (82 mg, 0.034 mmol) are put into solution in dichloromethane (1.5 mL) in the presence of a molecular sieve. After stirring vigorously for 5 minutes, triphenylphosphine oxide (19 mg, 0.068 mmol) is added rapidly to the mixture. After stirring for 4 days at ambient temperature, the medium is filtered on celite and concentrated under reduced pressure. The sought product 6a (69 mg; 0.029 mmol) is obtained after purification on silica gel [petroleum ether/ethyl acetate (3:2; v/v)] with a yield of 85% in mixture with its hydrated form.

Product 6a: colourless oil; Rf (EP/AcOEt, 1:1) 0.5.

NMR $^1$H (CDCl$_3$, 400 MHz) δ (ppm): Characteristic signals 6.26 (d, 1H, H4a, $J_{H4a-H5a}$=3.6 Hz); 4.87 (s, 1H, H1a); 4.83 (d, 1H, H7a, $J_{H7a-H7'a}$=11.7 Hz); 4.68-4.61 (m, 1H, H5a); 4.60 (d, 1H, H7'a).

NMR $^{13}$C (CDCl$_3$, 100 MHz) δ (ppm): Characteristic signals 183.5 (C2a); 144.9 (C3a); 126.2 (C4a); 97.7 (C1a); 71.0 (C5a); 70.6 (C7a); 66.1 (C6a).

Procedure 2:

Silver triflate (5.2 mg, 0.020 mmol) is added to a solution of the donor 5a (50 mg, 0.020 mmol) and benzyl alcohol (4.4 µL, 0.040 mmol) in dichloromethane (0.75 mL) at 0° C. After stirring for 3 hours, the reaction medium is neutralized by the addition of triethylamine, the silver salts are filtered on celite and the filtrate is concentrated under vacuum. Purification on silica gel [petroleum ether/ethyl acetate (3:2; v/v)] makes it possible to obtain 38 mg (0.016 mmol) of the deoxy compound 6a with a yield of 75%.

Other Signals:

NMR $^1$H (CDCl$_3$, 400 MHz) δ (ppm): 8.10-7.70 (m, 20H, arom. H); 7.60-7.12 (m, 55H, arom. H); 5.39 (t, 1H, H3e, $J_{H2e-H3e}$=$J_{H3e-H4e}$=9.7 Hz); 5.28-5.17 (m, 5H, H1b, H2b, H4b, H2e, H4e); 5.09-5.02 (m, 4H, H2c, H4c, H2d, H4d); 4.95 (d, 1H, H1e, $J_{H1c-H2c}$=8.0 Hz); 4.63 (d, 1H, H1d, $J_{H1d-H2d}$=7.9 Hz); 4.61 (d, 1H, H1e, $J_{H1e-H2e}$=8.0 Hz); 4.53-4.40 (m, 3H, H6a, 2H6); 4.38-4.32 (m, 2H, H3b, H6); 4.25-4.18 (m, 2H, H6'a, H3); 4.15-3.90 (m, 8H, H5b, H3, H5, 5H6); 3.80-3.70 (m, 2H, H5e, H5).

NMR $^{13}$C (CDCl$_3$, 100 MHz) δ (ppm): 165.8, 165.7, 165.4, 164.9, 164.6, 164.5, 163.9, 163.8 (14C, OCOPh); 136.1 (quat. arom. C OCH$_2$Ph); 133.3, 133.2, 133.1, 133.0, 132.9, 132.7, 129.9, 129.8, 129.7, 129.6, 129.5, 129.4, 129.3, 129.2, 129.0, 128.8, 128.6, 128.5, 128.4, 128.3, 128.2, 128.1, 128.0, 127.8 (arom. C); 100.9 (2C, C1d, C1e); 100.1 (C1c); 98.3 (C1b); 78.3, 78.0 (2C, C3c, C3d); 76.8 (C3b); 73.7 (2C, C2c, C2d); 73.0 (C2b); 72.8 (C5b); 72.6 (C3e); 72.1 (1C, C5); 71.6 (C2e); 71.3 (2C, C5e, C5); 69.9, 69.8 (3C, C4c, C4d, C4e); 69.3 (C4b); 63.4 (2C, C6e, C6); 63.1 (2C, C6b, C6).

| HRMS (ESI+): | [M + Na]+ $C_{135}H_{11}NaO_{39}$ | theoretical m/z: 2377.6522 |
|---|---|---|
| | | measured m/z: 2377.6516 |

6.7/ Preparation of benzyl 2,3,4,6-tetra-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-6-O-benzoyl-4-deoxy-β-D-manno-hex-3-enopyranosyl (Product 7a)

Compound 6a (69 mg, 0.029 mmol) is solubilized in THF (0.7 mL) then L-Selectride (1M solution in THF; 28 μL, 0.028 mmol) is added at −78° C. After 90 minutes at −78° C., the reaction is assumed to have stopped and the medium is neutralized by the addition of a few drops of acetic acid. Once the medium has returned to ambient temperature, dichloromethane is added and the organic phase is washed with a 10% aqueous hydrochloric acid solution, a saturated aqueous solution of sodium bicarbonate and a saturated aqueous solution of sodium chloride. The desired compound 7a is thus obtained after drying (MgSO4) and concentration of the organic phase (68 mg; 0.029 mmol; 100%).
Product 7a: colourless oil; Rf (EP/AcOEt, 1:1) 0.5.
NMR $^1$H (CDCl$_3$, 500 MHz) δ (ppm): Characteristic signals 4.94 (d, 1H, H4a, $J_{H4a\text{-}H5a}$=1.1 Hz); 4.86 (d, 1H, $J_{H7a\text{-}H7'a}$=12.0 Hz); 4.59 (d, 1H, H7'a); 4.44 (d, 1H, H1a, $J_{H1a\text{-}H2a}$=2.2 Hz); 4.25-4.20 (m, 2H, H5a, H6a).
NMR $^{13}$C (CDCl$_3$, 100 MHz) δ (ppm): Characteristic signals 151.4 (C3a); 104.1 (C4a); 97.1 (C1a); 70.4 (C5a); 70.1 (C7a); 66.2 (C6a); 65.1 (C2a).
Other Signals:
NMR $^1$H (CDCl$_3$, 500 MHz) δ (ppm): 8.03-7.70 (m, 20H, arom. H); 7.61-7.13 (m, 55H, arom. H); 5.39 (t, 1H, H3e, $J_{H2e\text{-}H3e}$=$J_{H3e\text{-}H4e}$=9.6 Hz); 5.30 (t, 1H, H4b, $J_{H3b\text{-}H4b}$=$J_{H4b\text{-}H5b}$=8.3 Hz); 5.22 (dd, 1H, H2e, $J_{H1e\text{-}H2e}$=7.9 Hz); 5.20 (t, 1H, H4e, $J_{H4e\text{-}H5e}$=9.6 Hz); 5.18-5.16 (m, 2H, H1b, H2b); 5.07-4.98 (m, 4H, H2c, H4c, H2d, H4d); 4.85 (d, 1H, H1e, $J_{H1c\text{-}H2c}$=7.9 Hz); 4.62 (d, 2H, H1d, H1e, $J_{H1d\text{-}H2d}$=7.9 Hz); 4.51 (dd, 1H, H6, $J_{H5\text{-}H6}$=3.8 Hz, $J_{H6\text{-}H6'}$=12.3 Hz); 4.36-4.30 (m, 2H, H3b, H6); 4.20-4.14 (m, 2H, H6'a, H3); 4.12-3.90 (m, 10H, H2a, H5b, H3, H5, 6H6); 3.77-3.70 (m, 2H, H5e, H5).
NMR $^{13}$C (CDCl$_3$, 100 MHz) δ (ppm): 166.1, 165.9, 165.8, 165.7, 165.4, 164.9, 164.7, 164.3, 163.9, 163.8 (14C, OCOPh); 136.6 (quat. arom. C OCH$_2$Ph); 133.4, 133.2, 133.1, 133.0, 132.9, 132.7, 129.9, 129.7, 129.6, 129.5, 129.4, 129.3, 129.2, 129.0, 128.8, 128.6, 128.5, 128.4, 128.3, 128.2, 128.1, 128.0, 127.8 (arom. C); 100.9 (2C, C1d, C1e); 100.6 (C1c); 97.3 (C1b); 78.3, 77.9 (2C, C3c, C3d); 77.4 (C3b); 73.5 (1C, C2); 72.9 (2C, C2b, C2); 72.6 (C3e); 72.0 (C5b); 71.6 (3C, C5e, 2C5); 71.3 (C2e); 70.4 (2C, C4c, C4d); 69.8 (C4e); 69.3 (C4b); 63.5, 63.3, 63.1 (4C, C6b, C6c, C6d, C6e).

| HRMS (ESI+): | [M + Na]+ $C_{135}H_{112}NaO_{39}$ | theoretical m/z: 2379.6678 |
|---|---|---|
| | | measured m/z: 2379.6667 |
| | [M + K]+ $C_{135}H_{112}KO_{39}$ | theoretical m/z: 2395.6418 |
| | | measured m/z: 2395.6542 |

6.8/ Preparation of benzyl β-D-glucopyranosyl-(1→3)-β-D-glucopyranosyl-(1→3)-β-D-glucopyranosyl-(1→3)-β-D-glucopyranosyl-(1→3)-4-deoxy-β-D-manno-hex-3-enopyranosyl (Product 8a)

The compound 7a (65 mg, 0.028 mmol) in a methanol/dichloromethane mixture (2:1, v/v) then sodium methylate (1M solution in THF; 0.56 mL, 0.056 mmol) are introduced successively into a flask. After stirring for 6 hours at ambient temperature, the medium is neutralized by the addition of Amberlite IR120—H+ resin, filtered then concentrated under reduced pressure. The debenzoylated compound 8a is obtained after chromatography [dichloromethane/methanol (99:1; v/v)] with a quantitative yield (25 mg; 0.028 mmol).
Product 8a: colourless oil.
NMR $^1$H (CDCl$_3$, 400 MHz) δ (ppm): Characteristic signals 5.06 (d, 1H, H4a, $J_{H4a\text{-}H5a}$=1.5 Hz); 4.82 (d, 1H, H7a, $J_{H7a\text{-}H7'a}$=12.2 Hz); 4.60 (d, 1H, H7'a); 4.49 (d, 1H, H1a, $J_{H1a\text{-}H2a}$=1.8 Hz); 4.12-4.08 (m, 1H, H5a); 3.87 (d, 1H, H2a).
NMR $^{13}$C (CD$_3$OD, 100 MHz) δ (ppm): Characteristic signals 153.5 (C3a); 103.8 (C4a); 99.8 (C1a); 71.2 (C7a); 67.2 (C2a); 65.6 (C6a).
Other Signals:
NMR $^1$H (CD$_3$OD, 400 MHz) δ (ppm): 7.35-7.16 (m, 5H, arom. H); 4.71 (d, 1H, H1b, $J_{H1b\text{-}H2b}$=7.5 Hz); 4.54 (d 1H, H1, $J_{H1\text{-}H2}$=8.0 Hz); 4.53 (d, 1H, H1, $J_{H1\text{-}H2}$=7.8 Hz); 4.46 (d, 1H, H1e, $J_{H1e\text{-}H2e}$=7.8 Hz); 3.80-3.73 (m, 4H, 4H6); 3.60-3.43 (m, 10H, H6a, H6'a, H2b, 3H3, 4H6); 3.40-3.32 (m, 2H, H2c, H2d); 3.30-3.17 (m, 8H, H3e, 3H4, 4 H5); 3.16 (dd, 1H, H2e, $J_{H2e\text{-}H3e}$=9.3 Hz); 3.15 (t, 1H, H4e, $J_{H3e\text{-}H4e}$=$J_{H4e\text{-}H5e}$=9.8 Hz).
NMR $^{13}$C (CD$_3$OD, 100 MHz) δ (ppm): 138.9 (quat. arom. C OCH$_2$Ph); 129.6, 129.4, 128.9 (arom. C); 105.1, 104.6 (3C, C1c, C1d, C1e); 100.5 (C1b); 87.4, 87.2, 87.1 (3C, C3b, C3c, C3d); 78.1, 77.8, 77.7 (5C, C3e, C5b, C5c, C5d, C5e); 75.5 (C2e); 75.0, 74.9 (3C, C5a, C2c, C2d); 74.0 (C2b); 71.5 (C4e); 70.0, 69.9 (3C, C4b, C4c, C4d); 62.6, 62.5 (4C, C6b, C6c, C6d, C6e).

6.9/ Preparation of β-D-glucopyranosyl-(1→3)-β-D-glucopyranosyl-(1→3)-β-D-glucopyranosyl-(1→3)-β-D-glucopyranosyl-(1→3)-4-deoxy-(α,β)-D-mannopyranose (Product Ca)

After dissolution of compound 8a (24 mg, 0.027 mmol) in methanol, palladium acetate (25 mg, 0.111 mmol) is added to the medium. After stirring for 7 days under a hydrogen atmosphere at ambient temperature, the medium is filtered then concentrated under reduced pressure. Compound Ca is obtained after purification by Sephadex G-10 steric exclusion (eluent: water) and freeze-drying of the collected fractions (21 mg; 0.027 mmol; 100%).
Ca: white foam; Rf (AcOEt/iPrOH/H$_2$O, 3:2:2) 0.2.
NMR $^1$H (D$_2$O, 400 MHz) δ (ppm): Characteristic signals 5.12 (m, 1H, H1aα); 1.72-1.60 (m, 2H, H4a, H4'a).
NMR $^{13}$C (D$_2$O, 100 MHz) δ (ppm): Characteristic signals 96.0 (C1a); 67.2 (C2a); 61.0 (C6a); 28.8 (C4a).
Other Signals:
NMR $^1$H (D$_2$O, 400 MHz) δ (ppm): 4.68 (d, 2H, 2H1, $J_{H1\text{-}H2}$=8.2 Hz); 4.64 (d, 2H, 2 H1, $J_{H1\text{-}H2}$=8.0 Hz); 3.86-3.73 (m, 5H, H6a, H6b, H6c, H6d, H6e); 3.71-3.56 (m, 10H, H2a, H5a, H6'a, H3b, H6'b, H3c, H6'c, H3d, H6'd, H6'e); 3.55-3.33 (m, 13H, H3a, H5a, H2b, H4b, H5b, H2c, H4c, H5c, H2d, H4d, H5d, H3e, H5e); 3.31 (t, 1H, H4e, $J_{H3e\text{-}H4e}$=$J_{H4e\text{-}H5e}$=9.3 Hz); 3.24 (dd, 1H, H2e, $J_{H1e\text{-}H2e}$=8.0 Hz, $J_{H2e\text{-}H3e}$=9.3 Hz).

NMR $^{13}$C (D$_2$O, 100 MHz) δ (ppm): 103.1, 102.8 (4C, C1b, C1c, C1d, C1e); 84.5, 84.4 (4C, C3a, C3b, C3c, C3d); 76.3, 75.9, 75.8 (6C, C5a, C5b, C5c, C5d, C3e, C5e); 73.8, 73.6 (5C, C2a, C2b, C2c, C2d, C2e); 69.9 (C4e); 64.4 (3C, C4b, C4c, C4d); 61.0 (4C, C6b, C6c, C6d, C6e).

HRMS (ESI$^+$): [M + Na]$^+$ C$_{30}$H$_{52}$NaO$_{25}$ theoretical m/z: 835.2695
measured m/z: 835.2694

Example 7

The product 1b is prepared according to the procedure described in the Patent Application FR2804684, according to the procedure of Example 6.

7.1/ Preparation of 2,3,4,6-tetra-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-1,2,4,6-tetra-O-benzoyl-(α,β)-D-glucopyranose (Product 2b)

The oligosaccharide 2a (200 mg, 0.202 mmol) is dissolved in pyridine (20 mL). The reaction medium is then cooled down to 0° C. then benzoyl chloride (5.2 mL, 44.4 mmol) is added. After stirring for 2 days at ambient temperature, the medium is evaporated, dissolved in dichloromethane then washed with a 10% aqueous hydrochloric acid solution, with a saturated solution of sodium bicarbonate and a saturated solution of sodium chloride until neutrality is reached. The organic phase is then dried over MgSO$_4$ and evaporated. The residue is purified by silica gel chromatography [petroleum ether/ethyl acetate (1:1; v/v)] in order to produce the perbenzoylated derivative 2a in the faun of a mixture of anomers a/13:1/1 with a yield of 85% (545 mg, 0.178 mmol).
Product 2b: colourless oil; Rf (EP/AcOEt, 1:1) 0.4.
NMR $^1$H (CDCl$_3$, 400 MHz) δ (ppm): Characteristic signals for 2bα 6.60 (d, 1H, H1a, J$_{H1a-H2a}$=3.8 Hz); 5.42 (t, 1H, H4a, J$_{H3a-H4a}$=J$_{H4a-H5a}$=9.8 Hz); Characteristic signals for 2bβ 6.02 (d, 1H, H1a, J$_{H1a-H2a}$=7.1 Hz); 5.52 (t, 1H, H4a, J$_{H3a-H4a}$=J$_{H4a-H5a}$=9.0 Hz); 4.23-4.18 (m, 1H, H5a).
NMR $^{13}$C (CDCl$_3$, 100 MHz) δ (ppm): Characteristic signals for 2bα 89.7 (C1a); 76.3 (C3a); 72.7 (C2a); 70.2 (C5a); 68.8 (C4a); Characteristic signals for 2bβ 92.0 (C1a); 78.3 (C3a); 72.9 (C5a); 72.5 (C2a); 68.8 (C4a); 62.7 (C6a).
Other Signals:
NMR $^1$H (CDCl$_3$, 400 MHz) δ (ppm): 8.01-7.65 (m, 60H, arom. H); 7.55-7.01 (m, 140H, arom. H); 5.36-5.30 (m, 3H, H2aβ, H3f); 5.20-5.12 (m, 5H, H2aα, H2f, H4f); 5.07-4.89 (m, 8H, 2H2, 2H4); 4.88-4.72 (m, 10H, H1b, 2H2, 2H4); 4.61-4.30 (m, 13H, H3aα, H3aβ, H5aα, H6aβ, H6'4β, H1c, H1d, H1e, H1f); 4.12-3.78 (m, 32H, H6aα, H6'aα, H3b, H6b, H6'b, H3c, H6c, H6'c, H3d, H6d, H6'd, H3e, H6e, H6'e, H5f, H6f, H6'f); 3.73-3.56 (m, 8H, H5b, H5c, H5d, H5e).
NMR $^{13}$C (CDCl$_3$, 100 MHz) δ (ppm): 166.0, 165.9, 165.8, 165.7, 165.4, 164.9, 164.7, 164.6, 164.4, 164.3, 164.1, 163.8, 163.6, 163.5 (OCOPh); 133.5, 133.2, 133.1, 133.0, 132.8, 132.6, 130.0, 129.9, 129.7, 129.6, 129.5, 129.4, 129.3, 129.2, 129.1, 129.0, 128.9, 128.7; 128.6, 128.5, 128.4, 128.2, 128.0, 127.9 (arom. C); 101.4, 101.0, 100.9, 100.8, 100.7 (10C, C1b, C1c, C1d, C1e, C1f); 78.3, 78.2, 78.1, 77.9 (8C, C3b, C3c, C3d, C3e); 73.3, 73.2, 73.1 (6C, 3C2); 72.9 (2C, C2); 72.5 (C3f); 72.1 (C5f); 71.7, 71.6 (8C, C5b, C5c, C5d, C5e); 71.3 (2C, C2f); 70.2 (4C, 2C4); 70.0 (4C, 2C4); 69.8 (2C, C4f); 63.7, 63.4, 63.1 (11C, C6aα, C6b, C6c, C6d, C6e, C6f).

HRMS (ESI$^+$): [M + Na]$^+$ C$_{176}$H$_{142}$NaO$_{51}$ theoretical m/z: 3093.8416
measured m/z: 3093.8418
[M + K]$^+$ C$_{176}$H$_{142}$KO$_{51}$ theoretical m/z: 3109.8155
measured m/z: 3109.8119

7.2/ Preparation of 2,3,4,6-tetra-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl+D-glucopyranosyl-(1→3)-2,4,6-tri-O-benzoyl-α-D-glucopyranosyl bromide (Product 3b)

The bromination of compound 2b (643 mg, 0.209 mmol) is carried out as described for 3a in dichloromethane (15 mL) in the presence of hydrobromic acid (1.1 mL, 6.364 mmol) in order to produce 633 mg of brominated compound 3b in a quantitative manner.
Product 3b: colourless oil.
NMR $^1$H (CDCl$_3$, 400 MHz) δ (ppm): Characteristic signals 6.68 (d, 1H, H1a, J$_{H1a-H2a}$=3.8 Hz); 5.48 (t, 1H, H4a, J$_{H3a-H4a}$=J$_{H4a-H5a}$=9.7 Hz); 4.82 (dd, 1H, H2a, J$_{H2a-H3a}$=9.7 Hz); 4.61 (t, 1H, H3a); 4.60 (dd, 1H, H6a, J$_{H5a-H6a}$=3.8 Hz, J$_{H6a-H6'a}$=12.2 Hz); 4.55-4.51 (m, 1H, H5a); 4.37 (dd, 1H, H6'a, J$_{H5a-H6'a}$=4.2 Hz).
NMR $^{13}$C (CDCl$_3$, 100 MHz) δ (ppm): Characteristic signals 87.7 (C1a); 76.3 (C3a); 73.4 (C2a); 72.7 (C5a); 67.6 (C4a); 62.0 (C6a).
Other Signals:
NMR $^1$H (CDCl$_3$, 400 MHz) δ (ppm): 8.00-7.71 (m, 26H, arom. H); 7.61-7.03 (m, 69H, arom. H); 5.39 (t, 1H, H3f, J$_{H2f-H3f}$=J$_{H3f-H4f}$=9.7 Hz); 5.22 (dd, 1H, H2f, J$_{H1f-H2f}$=7.8 Hz); 5.21 (t, 1H, H4f, J$_{H4f-H5f}$=9.7 Hz); 5.05-4.97 (m, 4H, 3H2, H4); 4.94 (t, 1H, H4, J$_{H4-H5}$=9.3 Hz); 4.88 (d, 1H, H1, J$_{H1-H2}$=8.2 Hz); 4.87-4.77 (m, 3H, H2, 2H4); 4.55 (d, 1H, H1f); 4.49 (d, 1H, H1, J$_{H1-H2}$=7.7 Hz); 4.42 (d, 1H, H1, J$_{H1-H2}$=7.5 Hz); 4.40 (d, 1H, H1, J$_{H1-H2}$=7.5 Hz); 4.19-4.12 (m, 2H, H3, H6); 4.08-3.81 (m, 12H, 3H3, 9H6); 3.77-3.71 (m, 1H, H5f); 3.71-3.60 (m, 4H, H5b, H5c, H5d, H5e).
NMR $^{13}$C (CDCl$_3$, 100 MHz) δ (ppm): 165.9, 165.8, 165.7, 165.4, 164.9, 164.8, 164.7, 164.6, 164.5, 164.3, 163.8, 163.5 (19C, OCOPh); 133.8, 133.4, 133.2, 133.1, 133.0, 132.8, 132.6, 129.9, 129.7, 129.6, 129.5, 129.4, 129.3, 129.2, 129.1, 129.0, 128.9, 128.7, 128.6, 128.5, 128.4, 128.3, 128.2, 128.1, 128.0, 127.9 (arom. C); 101.3, 101.0, 100.8, 100.7 (5C, C1b, C1c, C1d, C1e, C1f); 78.4, 78.1, 77.8, 77.4 (4C, C3b, C3c, C3d, C3e); 73.3, 73.2, 72.9 (4C, C2b, C2c, C2d, C2e); 72.5 (C3f); 71.8, 71.6 (5C, C5b, C5c, C5d, C5e, CM); 71.3 (C2f); 70.2 (4C, C4b, C4c, C4d, C4e); 69.8 (C4f); 63.5, 63.4, 63.1 (5C, C6b, C6c, C6d, C6e, C6f).

7.3/ Preparation of 2,3,4,6-tetra-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl-2-D-gluhex-1-enopyranose (Product 4b)

Compound 3b (550 mg, 0.181 mmol) is involved in an elimination reaction following the same procedure as that described for 4a in dichloromethane (10 mL) in the presence of DBU (35 μL, 0.235 mmol). Purification on a silica gel column [petroleum ether/ethyl acetate (3:2; v/v)] makes it possible to obtain 458 mg of the desired product 4b with a yield of 85%.

4b: white solid; Rf (EP/AcOEt, 1:1) 0.5.

NMR $^1$H (CDCl$_3$, 400 MHz) δ (ppm): Characteristic signals 6.54 (s, 1H, H1a); 5.69 (d, 1H, H3a, $J_{H3a-H4a}$=1.6 Hz); 4.64 (dd, 1H, H6a, $J_{H5a-H6a}$=8.8 Hz, $J_{H6a-H6'a}$=12.4 Hz); 4.32 (dd, 1H, H6'a, $J_{H5a-H6'a}$=2.4 Hz).

NMR $^{13}$C (CDCl$_3$, 100 MHz) δ (ppm): Characteristic signals 138.2 (C1a); 74.1 (C5a); 72.3 (C4a); 68.6 (C3a); 61.6 (C6a).

Other Signals:

NMR $^1$H (CDCl$_3$, 400 MHz) δ (ppm): 7.95-7.62 (m, 25H, arom. H); 7.51-6.93 (m, 70H, arom. H); 5.29 (t, 1H, H3f, $J_{H2f-H3f}$=$J_{H3f-H4f}$=9.7 Hz); 5.12 (dd, 1H, H2f, $J_{H1f-H2f}$=8.0 Hz); 5.11 (t, 1H, H4f, $J_{H4f-H5f}$=9.7 Hz); 5.10-5.12 (m, 1H, H2b, H4b); 4.96-4.80 (m, 4H, H1, 2H2, H4); 4.78-4.71 (m, 3H, H2, 2H4); 4.60 (d, 1H, H1, $J_{H1-H2}$=8.0 Hz); 4.52-4.44 (m, 3H, H4a, H5a, H1); 4.42-4.35 (m, 3H, 2H1, H6, $J_{H1-H2}$=8.0 Hz); 4.07-4.01 (m, 1H, H5b); 3.98 (dd, 1H, H6, $J_{H5-H6}$=3.5 Hz, $J_{H6-H6'}$=11.9 Hz); 3.93-3.75 (m, 1H, 3H3c, 8H6); 3.74-3.55 (m, 4H, H5c, H5d, H5e, H5f).

NMR $^{13}$C (CDCl$_3$, 100 MHz) δ (ppm): 165.8, 165.7, 165.4, 165.2, 165.1, 164.9, 164.7, 164.6, 163.8, 163.7, 163.6 (19C, OCOPh); 133.3, 133.2, 133.1, 133.0, 132.9, 132.8, 132.7, 132.6, 129.9, 129.8, 129.7, 129.6, 129.5, 129.4, 129.3, 129.2, 129.1, 129.0, 128.8, 128.6, 128.5, 128.4, 128.3, 128.2, 128.1, 128.0, 127.9, 127.7 (C2a, arom. C); 101.2 (C1b); 100.9, 100.8 100.7 (4C, C1c, C1d, C1e, C1f); 78.2, 78.0 (4C, C3b, C3c, C3d, C3e); 73.3 (1C, C2); 73.1 (C2b); 73.0 (C2); 72.7 (C5b); 72.6 (2C, C3f, C2); 72.0, 71.8, 71.6 (4C, C5c, C5d, C5e, C5f); 71.3 (C2f); 70.2, 70.1, 69.8, 69.7 (5C, C4b, C4c, C4d, C4e, C4f); 63.5, 63.3, 63.1 (5C, C6b, C6c, C6d, C6e, C6f).

| HRMS (ESI$^+$): | [M + Na]$^+$ C$_{169}$H$_{136}$NaO$_{49}$ | theoretical m/z: 2971.8048 |
| --- | --- | --- |
| | | measured m/z: 2971.8034 |
| | [M + K]$^+$ C$_{169}$H$_{136}$KO$_{49}$ | theoretical m/z: 2987.7787 |
| | | measured m/z: 2987.7811 |

7.4/ Preparation of 2,3,4,6-tetra-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-4,6-di-O-benzoyl-α-D-glucopyranos-2-ulosyl bromide (Product 5b)

Compound 5b was obtained following the same procedure as that described for the preparation of 5a from 4b (124 mg, 0.042 mmol) in 1.5 mL of dichloromethane, NBS (22.4 mg, 0.126 mmol) and methanol (3.4 μL, 0.084 mmol) with a quantitative yield (123 mg, 0.042 mmol).

Product 5b: colourless oil.

NMR $^1$H (CDCl$_3$, 400 MHz) δ (ppm): Characteristic signals 6.25 (s, 1H, H1a); 5.44 (t, 1H, H4a, $J_{H3a-H4a}$=$J_{H4a-H5a}$=10.2 Hz); 5.16 (d, 1H, H3a).

NMR $^{13}$C (CDCl$_3$, 100 MHz) δ (ppm): 1 Characteristic signals 91.5 (C2a); 83.9 (C1a); 76.3 (C3a); 72.6 (C5a); 69.0 (C4a); 61.7 (C6a).

Other Signals:

NMR $^1$H (CDCl$_3$, 400 MHz) δ (ppm): 8.09-7.70 (m, 25H, arom. H); 7.60-6.84 (m, 65H, arom. H); 5.37 (t, 1H, H3f, $J_{H2f-H3f}$=$J_{H3f-H4f}$=9.7 Hz); 5.20 (dd, 1H, H2f, $J_{H1f-H2f}$=8.0 Hz); 5.19 (t, 1H, H4f, $J_{H4f-H5f}$=9.7 Hz); 5.10 (dd, 1H, H2b, $J_{H1b-H2b}$=8.1 Hz, $J_{H2b-H3b}$=9.1 Hz); 5.07-4.96 (m, 4H, H1b, H2, H4); 4.92-4.78 (m, 4H, 2H2, 2H4); 4.73 (d, 1H, H1, $J_{H1-H2}$=8.0 Hz); 4.66 (d, 1H, H1, $J_{H1-H2}$=8.0 Hz); 4.65-4.57 (m, 2H, H5a, H6); 4.54 (d, 1H, H1, $J_{H1-H2}$=8.0 Hz); 4.49 (d, 1H, H1, $J_{H1-H2}$=7.7 Hz); 4.47-4.41 (m, 1H, H6); 4.35 (dd, 1H, H6, $J_{H5-H6}$=4.9 Hz, $J_{H6-H6'}$=12.4 Hz); 4.28 (t, 1H, H3b, $J_{H3b-H4b}$=9.1 Hz); 4.19 (dd, 1H, H6, $J_{H5-H6}$=3.5 Hz, $J_{H6-H6'}$=12.2 Hz); 4.12 (dd, 1H, H6, $J_{H5-H6}$=6.2 Hz, $J_{H6-H6'}$=12.2 Hz); 4.05-3.81 (m, 11H, H5b, H3c, H3d, H3e, 7H6); 3.80-3.62 (m, 4H, H5c, H5d, H5e, H5f).

NMR $^{13}$C (CDCl$_3$, 100 MHz) δ (ppm): 165.9, 165.8, 165.7, 165.4, 164.9, 164.7, 164.6, 164.3, 163.8, 163.6 (18C, OCOPh); 133.6, 133.3, 133.2, 133.1, 133.0, 132.9, 132.6, 130.0, 129.8, 129.7, 129.6, 129.5, 129.4, 129.3, 129.2, 129.1, 129.0, 128.8, 128.6, 128.4, 128.3, 128.2, 128.1, 127.9 (arom. C); 101.0, 100.9, 100.7, 100.6 (5C, C1b, C1c, C1d, C1e, C1f); 78.3, 78.2, 78.1, 78.0 (4C, C3b, C3c, C3d, C3e); 73.5, 73.1, 73.0, 72.8 (4C, C2b, C2c, C2d, C2e); 72.6 (C3f); 71.9, 71.8, 71.6 (5C, C5b, C5c, C5d, C5e, C5f); 71.3 (C2f); 70.2, 70.1, 70.0, 69.8 (5C, C4b, C4c, C4d, C4e, C4f); 63.6, 63.5, 63.4, 63.3, 63.2 (5C, C6b, C6c, C6d, C6e, C6f).

7.5/ Preparation of benzyl 2,3,4,6-tetra-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-6-O-benzoyl-4-deoxy-β-D-gluco-hex-3-enopyranos-2-uloside (Product 6b)

Benzyl alcohol (7 μL, 0.068 mmol) and ulosyl bromide 5b (183 mg, 0.063 mmol) are put into solution in dichloromethane (1.5 mL) in the presence of a molecular sieve. After stirring vigorously for 5 minutes, triphenylphosphine oxide (19 mg, 0.068 mmol) is rapidly added to the mixture. After stirring for 4 days at ambient temperature, the medium is filtered on celite, concentrated under reduced pressure and purified by chromatography on silica [petroleum ether/ethyl acetate (3:2; v/v)]. After evaporation of the solvents, the crude product thus obtained is dissolved in benzene (8 mL), then water (200 μL, 11.1 mol) and sodium bicarbonate (200 mg, 2.381 mmol) are added. The medium is then taken to 80° C. for 1.5 hours. After returning to ambient temperature, the suspension is dried over MgSO4, filtered and concentrated under vacuum in order to produce the product 6b (120 mg; 0.029 mmol) with an overall yield of 67%.

Product 6b: colourless oil; Rf (EP/AcOEt, 1:1) 0.5.

NMR $^1$H (CDCl$_3$, 400 MHz) δ (ppm): Characteristic signals 6.26 (d, 1H, H4a, $J_{H4a-H5a}$=3.5 Hz); 4.87 (s, 1H, H1a); 4.83 (d, 1H, H7a, $J_{H7a-H7'a}$=11.7 Hz); 4.71-4.65 (m, 1H, H5a); 4.60 (d, 1H, H7'a).

NMR $^{13}$C (CDCl$_3$, 100 MHz) δ (ppm): Characteristic signals 183.6 (C2a); 144.9 (C3a); 126.3 (C4a); 97.7 (C1a); 71.0 (C5a); 70.6 (C7a); 66.1 (C6a).

Other Signals:

NMR $^1$H (CDCl$_3$, 400 MHz) δ (ppm): 8.06-7.71 (m, 25H, arom. H); 7.60-7.12 (m, 65H, arom. H); 5.37 (t, 1H, H3f, $J_{H2f-H3f}=J_{H3f-H4f}=9.5$ Hz); 5.30-5.16 (m, 5H, H1b, H2b, H2f, H4b, H4f); 5.07-4.94 (m, 6H, H2c, H2d, H2e, H4c, H4d, H4e); 4.90 (d, 1H, H1e, $J_{H1c-H2c}=8.0$ Hz); 4.57 (d, 1H, H1, $J_{H1-H2}=8.2$ Hz); 4.55 (d, 2H, H$_1$, $J_{H1-H2}=8.0$ Hz); 4.54-4.43 (m, 3H, H6a, 2H6); 4.38-4.32 (m, 2H, H3b, H6); 4.24-4.20 (m, 2H, H3, H6'a); 4.16-4.04 (m, 4H, H6'a, H3, H5, H6); 4.02-3.82 (m, 8H, H3, 2H5, 5H6); 3.76-3.64 (m, 3H, H5f, 2H5).

NMR $^{13}$C (CDCl$_3$, 100 MHz) δ (ppm): 165.9, 165.8, 165.7, 165.4, 164.9, 164.7, 164.6, 164.4, 163.8, 163.6 (15C, OCOPh); 136.1 (quat. arom. C OCH$_2$Ph); 133.3, 133.1, 133.0, 132.9, 132.6, 130.0, 129.8, 129.7, 129.6, 129.5, 129.4, 129.3, 129.2, 129.1, 129.0, 128.8, 128.7, 128.6, 128.5, 128.4, 128.2, 128.1, 128.0 (arom. C); 101.0, 100.9, 100.8 (3C, C1d, C1e, C1f); 100.2 (C1c); 98.4 (C1b); 78.3, 78.2, 78.1 (3C, C3c, C3d, C3e); 77.6 (C3b); 73.3, 73.0, 72.9 (5C, C2b, C5b, C2c, C2d, C2e); 72.6 (C3f); 72.1, 72.0, 71.8 (3C, C5); 71.6 (C2f); 71.3 (2C, C5f, C5); 70.1, 70.0 (3C, C4c, C4d, C4e); 69.8 (C4f); 69.3 (C4b); 63.5, 63.4 (3C, C6f, 2C6); 63.2, 63.1 (2C, C6b, C6).

| HRMS (ESI$^+$): | [M + Na]$^+$ C$_{162}$H$_{132}$NaO$_{47}$ | theoretical m/z: 2851.7837 |
| | | measured m/z: 2852.7830 |
| | [M + K]$^+$ C$_{162}$H$_{132}$KO$_{47}$ | theoretical m/z: 2867.7576 |
| | | measured m/z: 2867.7508 |

7.6/ Preparation of benzyl 2,3,4,6-tetra-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)-2,4,6-tri-O-benzoyl-β-D-glucopyranosyl-(1→3)6-O-benzoyl-4-deoxy-β-D-manno-hex-3-enopyranosyl (Product 7b)

The reduction of compound 6b (104 mg, 0.036 mmol) is carried out following the same procedure as that described for 7a in the presence of L-Selectride (1M solution in THF; 50 μL, 0.050 mmol) in THF (1 mL). The compound 7b (105 mg; 0.036 mmol) is thus obtained in a quantitative manner after treatments.

Product 7b: colourless oil; Rf (EP/AcOEt, 1:1) 0.5.

NMR $^1$H (CDCl$_3$, 400 MHz) δ (ppm): Characteristic signals 4.96 (d, 1H, H4a, $J_{H4a-H5a}<1.0$ Hz); 4.60 (d, 1H, H7'a, $J_{H7a-H7'a}=11.7$ Hz); 4.45 (d, 1H, H1a, $J_{H1a-H2a}=2.2$ Hz); 4.28-4.22 (m, 2H, H5a, H6a).

NMR $^{13}$C (CDCl$_3$, 100 MHz) δ (ppm): Characteristic signals 151.4 (C3a); 104.1 (C4a); 97.0 (C1a); 70.3 (C5a); 70.0 (C7a); 66.2 (C6a); 65.1 (C2a).

Other Signals:

NMR $^1$H (CDCl$_3$, 400 MHz) δ (ppm): 8.04-7.73 (m, 25H, arom. H); 7.60-7.10 (m, 65H, arom. H); 5.39 (t, 1H, H3f, $J_{H2f-H3f}=J_{H3f-H4f}$9.7 Hz); 5.34 (t, 1H, H4b, $J_{H3b-H4b}=J_{H4b-H5b}=$8.6 Hz); 5.22 (dd, 1H, H2f, $J_{H1f-H2f}=7.7$ Hz); 5.21 (t, 1H, H4f, $J_{H4f-H5f}=9.7$ Hz); 5.19 (dd, 1H, H2b, $J_{H1b-H2b}=7.1$ Hz, $J_{H2b-H3b}=9.5$ Hz); 5.18 (d, 1H, H1b); 5.06-4.97 (m, 3H, H2, 2H4); 4.90-4.81 (m, 4H, H7a, 2H2, H4); 4.58 (d, 3H, 3H1, $J_{H1-H2}=7.7$ Hz); 4.53 (dd, 1H, H6, $J_{H5-H6}=3.3$ Hz, $J_{H6-H6'}=12.2$ Hz); 4.49 (d, 1H, H1, $J_{H1-H2}=8.0$ Hz); 4.39-4.32 (m, 2H, H3b, H6); 4.20-4.06 (m, 4H, H6'a, H3, H5, H6); 4.00-3.83 (m, 12H, H2a, H5f, 3H3, 7H6); 3.76-3.71 (m, 4H, 4H5).

NMR $^{13}$C (CDCl$_3$, 100 MHz) δ (ppm): 166.1, 165.9, 165.8, 165.7, 165.4, 164.9, 164.7, 164.6, 164.5, 164.4, 164.2, 163.8, 163.6 (17C, OCOPh); 136.5 (quat. arom. C OCH$_2$Ph); 133.4, 133.2, 133.1, 133.0, 132.9, 132.6, 129.9, 129.8, 129.7, 129.6, 129.5, 129.4, 129.3, 129.2, 129.1, 129.0, 128.9, 128.7, 128.6, 128.5, 128.4, 128.3, 128.2, 128.1, 128.0, 127.9 (arom. C); 101.0, 100.9, 100.7, 100.6 (4C, C1c, C1d, C1e, C1f); 97.3 (C1b); 78.2 (3C, C3c, C3d, C3e); 77.5 (C3b); 73.4, 73.1 (3C, C2c, C2d, C2e); 72.9 (C2b); 72.5 (C3f); 71.9 (C5b); 71.7 (1C, C5); 71.6 (3C, C5f, 2C5); 71.2 (C2f); 70.1 (2C, C4); 69.7 (C4f); 69.3, 69.2 (2C, C4b, C2); 63.4, 63.3, 63.1 (5C, C6b, C6c, C6d, C6e, C6f).

| HRMS (ESI$^+$): | [M + Na]$^+$ C$_{162}$H$_{134}$NaO$_{47}$ | theoretical m/z: 2853.7993 |
| | | measured m/z: 2853.7994 |
| | [M + K]$^+$ C$_{162}$H$_{134}$KO$_{47}$ | theoretical m/z: 2869.7732 |
| | | measured m/z: 2869.7650 |

7.7/ Preparation of benzyl II-D-glucopyranosyl-(1→3)-β-D-glucopyranosyl-(1→3)-β-D-glucopyranosyl-(1→3)-β-D-glucopyranosyl-(1→3)-β-D-glucopyranosyl-(1→3)-4-deoxy-β-D-manno-hex-3-enopyranosyl (Product 8b)

Compound 7b (105 mg, 0.036 mmol) is involved in a debenzoylation reaction following the same procedure as that described for 8a in a dichloromethane/methanol mixture (3:2; v/v) (2.5 mL) in the presence of MeONa (0.1 M solution in MeOH, 0.71 mL, 0.71 mmol). Purification on a silica gel column [ethyl acetate/methanol (3:2; v/v)] makes it possible to obtain 8b (38 mg) with a quantitative yield.

Product 8b: colourless oil.

NMR $^1$H (CD$_3$OD, 400 MHz) δ (ppm): Characteristic signals 5.06 (d, 1H, H4a, $J_{H4a-H5a}=1.6$ Hz); 4.82 (d, 1H, H7a, $J_{H7a-H7'a}=11.9$ Hz); 4.60 (d, 1H, H7'a); 4.49 (d, 1H, H1a, $J_{H1a-H2a}=1.8$ Hz); 4.12-4.08 (m, 1H, H5a); 3.88 (d, 1H, H2a).

NMR $^{13}$C (CD$_3$OD, 100 MHz) δ (ppm): Characteristic signals 153.5 (C3a); 103.9 (C4a); 99.8 (C1a); 71.2 (C7a); 67.2 (C2a); 65.6 (C6a).

Other Signals:

NMR $^1$H (CD$_3$OD, 400 MHz) δ (ppm): 7.30-7.17 (m, 5H, arom. H); 4.71 (d, 1H, H1b, $J_{H1b-H2b}=7.7$ Hz); 4.55 (d, 3H, H1c, H1d, H1e, $J_{H1-H2}=7.8$ Hz); 4.47 (d, 1H, H1f, $J_{H1f-H2f}=8.0$ Hz); 3.81-3.72 (m, 5H, 5H6); 3.62-3.44 (m, 12H, H6a, H6'a, H2b, 3H3, 5 H6); 3.40-3.34 (m, 3H, H2c, H2d, H2e); 3.32-3.14 (m, 12H, H2f, H3f, H4f, 4H4, 5 H5).

NMR $^{13}$C (CD$_3$OD, 100 MHz) δ (ppm): 138.9 (quat. arom. C OCH$_2$Ph); 129.4, 129.3, 128.9, 128.7 (arom. C); 105.2, 104.7 (4C, C1c, C1d, C1e, C1f); 100.5 (C1b); 87.4, 87.3, 87.1 (4C, C3b, C3c, C3d, C3e); 78.1, 77.8 (6C, C3f, C5b, C5c, C5d, C5e, C5f); 75.5 (C2f); 75.0, 74.9 (4C, C2c, C2d, C2e, C5a); 74.0 (C2b); 71.5 (C4f); 70.0, 69.9 (4C, C4b, C4c, C4d, C4e); 62.6, 62.5 (5C, C6b, C6c, C6d, C6e, C6f).

7.8/ Preparation of β-D-glucopyranosyl-(1→3)-β-D-glucopyranosyl-(1→3)-β-D-glucopyranosyl-(1→3)-β-D-glucopyranosyl-(1→3)-β-D-glucopyranosyl-(1→3)-4-deoxy-(α,β)-D-mannopyranose (Product Cb)

Compound 8b (60 mg, 0.056 mmol) is reduced and debenzylated following the same procedure as that described for Ca, namely by hydrogenolysis in the presence of palladium acetate (60 mg, 0.267 mmol). Purification on a Sephadex G-10 column leads in a quantitative manner to the desired product Cb in α/β mixture where compound a is by far the majority component.
Product Cb: white foam.
NMR $^1$H (D$_2$O, 400 MHz) δ (ppm): Characteristic signals 5.14 (d, 1H, H1aα, $J_{H1a-H2a}$=3.3 Hz); 1.75-1.60 (m, 2H, H4a).
NMR $^{13}$C (D$_2$O, 100 MHz) δ (ppm): Characteristic signals 96.0 (C1aα); 61.0 (C6a); 26.0 (C4a).
Other Signals:
NMR $^1$H (D$_2$O, 400 MHz) δ (ppm): 4.70 (d, 3H, H1, $J_{H1-H2}$=8.0 Hz); 4.66 (d, 2H, H1, $J_{H1-H2}$=8.2 Hz); 3.86-3.78 (m, 6H, H6a, H6b, H6c, H6d, H6e, H6f); 3.73-3.60 (m, 11H, H3a, H3b, H3c, H3d, H3e, H6'a, H6'b, H6'c, H6'd, H6'e, H6'f); 3.50-3.36 (m, 16H, H2a, H2b, H2c, H2d, H2e, H3f, H4b, H4c, H4d, H4e, H5a, H5b, H5c, H5d, H5e, H5f); 3.31 (t, 1H, H4f, $J_{H3f-H4f}=J_{H4f-H5f}$=9.3 Hz); 3.26 (dd, 1H, H2f, $J_{H1f-H2f}$=8.0 Hz, $J_{H2f-H3f}$=9.0 Hz).
NMR $^{13}$C (D$_2$O, 100 MHz) δ (ppm): 103.1, 102.8 (5C, C1b, C1c, C1d, C1e, C1f); 84.5, 84.3 (5C, C3a, C3b, C3c, C3d, C3e); 76.3, 75.9 (6C, C3f, C5a, C5b, C5c, C5d, C5e, C5f); 73.8, 73.6 (6C, C2a, C2b, C2c, C2d, C2e, C2f); 69.9 (C4f); 68.4 (4C, C4b, C4c, C4d, C4e); 61.0 (5C, C6b, C6c, C6d, C6e, C6f).

HRMS (ESI$^+$):  [M + Na]$^+$ C$_{36}$H$_{62}$NaO$_{30}$  theoretical m/z: 997.3224
measured m/z: 997.3201

7.9/ Preparation of β-D-glucopyranosyl-(1→3)-β-D-glucopyranosyl-(1→3)-β-D-glucopyranosyl-(1→3)-β-D-glucopyranosyl-(1→3)-β-D-glucopyranosyl-(1→3)-4-deoxy-D-mannitol (Product Db)

Compound Cb (40 mg, 0.041 mmol) is dissolved in a methanol/water mixture (4:1, v/v) then 10 equivalents of sodium borohydride (15.5 mg, 0.411 mmol) are added. After stirring for a week at ambient temperature, the medium is neutralized by the addition of a few drops of acetic acid, concentrated under reduced pressure, coevaporated 3 times with 10 mL of a methanol/acetic acid mixture (9:1, v/v) and finally with 3 times 10 mL of methanol. Compound Db is obtained after purification on a gel permeation column (Sephadex G-10, eluent: water) and freeze-drying of the fractions collected.
Product Db: white foam.
NMR $^1$H (D$_2$O, 400 MHz) δ (ppm): Characteristic signals 3.97-3.90 (m, 1H, H3a); 1.70-1.40 (m, 2H, H4a).
NMR $^{13}$C (D$_2$O, 100 MHz) δ (ppm): Characteristic signals 76.3 (C3a); 71.0 (C2a, C5a); 66.1 (C6a); 63.0 (C1a); 25.3 (C4a).
Other Signals:
NMR $^1$H (D$_2$O, 400 MHz) δ (ppm): 4.70 (d, 3H, H1, $J_{H1-H2}$=8.0 Hz); 4.66 (d, 2H, H1, $J_{H1-H2}$=8.0 Hz); 3.87-3.76 (m, 9H, H1a, H2a, H5a, H6a, H6b, H6c, H6d, H6e, H6f); 3.72-3.51 (m, 12H, H1'a, H3a, H3b, H3c, H3d, H3e, H6'a, H6'b, H6'c, H6'd, H6'e, H6'f); 3.50-3.36 (m, 14H, H2b, H2c, H2d, H2e, H3f, H4b, H4c, H4d, H4e, H5b, H5c, H5d, H5e, H5f); 3.31 (t, 1H, H4f, $J_{H3f-H4f}=J_{H4f-H5f}$=9.3 Hz); 3.26 (dd, 1H, H2f, $J_{H1f-H2f}$=8.0 Hz, $J_{H2f-H3f}$=9.3 Hz).
NMR $^{13}$C (D$_2$O, 100 MHz) δ (ppm): 103.1, 102.8 (5C, C1b, C1c, C1d, C1e, C1f); 84.5, 84.3 (4C, C3b, C3c, C3d, C3e); 76.3 (C50; 75.9 (5C, C3f, C5a, C5b, C5c, C5d, C5e); 73.8, 73.6 (5C, C2b, C2c, C2d, C2e, C2f); 69.9 (C4f); 68.4, 68.2 (4C, C4b, C4c, C4d, C4e); 61.0 (5C, C6b, C6c, C6d, C6e, C60.

HRMS (ESI$^+$):  [M + Na]$^+$ C$_{36}$H$_{64}$NaO$_{30}$  theoretical m/z: 999.3380
measured m/z: 999.3411

Examples 8 to 11 show the biological activities of compounds of the invention.
In these examples, the tested compounds are:
LAM5: laminaripentaose,
LAM7: laminariheptaose,
A2 is the compound prepared according to Example 3,
A0 represents the following compound:

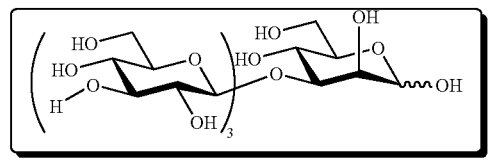

The control used is PBS.
The dosages used are 100 μg/mouse.

Example 8

Effect of LAM5, LAM7, A2 and A0 on the Phagocytosis of Peripheral Blood Cells

One or other of a control, LAM5, LAM7, A0 or A20 were injected, by peritoneal route, into a group of Balb/c mice (Jackson laboratory, Bar Harbor, Me., USA). 24 hours after the injection the mice were sacrificed. The peripheral blood was recovered from the orbital plexus in heparin (5 IU/ml) (Sigma)
After counting, a test for phagocytosis of HEMA particles (synthetic microspheres prepared from 2-hydroxyethyl-methacrylate copolymer) was carried out as described in: Rembaum et al., 1976, Vetvicka et al. 1982, Bilej et al., 1989. 0.1 ml of heparinized fresh blood was added to 0.05 ml of diluted HEMA particles (5×108/ml) and incubated for 60 minutes at 37° C. under occasional moderate stirring.
At the end of the incubation, the cell suspension was smeared onto microscope slides. The smears were evaluated under an optical microscope after Giemsa staining.

Cells surrounding at least three particles were considered to be positive.

The average results are represented graphically in FIG. 1. They clearly show that both A0 and A2 strongly stimulate phagocytosis in the monocytes and the granulocytes.

Example 9

Effect of the Oligosaccharides on the Phagocytosis of Cells Obtained from the Peritoneal Cavity

One or other of a control, LAM7, LAM5, A0 or A2 were injected, by intraperitoneal route, into a group of Balb/c mice (Jackson laboratory, Bar Harbor, Me., USA).

After 24 hours, the mice were sacrificed, the peritoneal cells were collected in a Hanks medium (Sigma).

After counting of the cells in a haemocytometer, the peritoneal cells were diluted to $1 \times 10^7$ in an RPMI 1640 medium (Sigma) with 5% foetal calf serum (Hyclone, Logan, Utah, USA).

$2 \times 10^6$ cells in 0.2 ml of RPMI 1640 medium with 5% foetal calf serum added were mixed with the same volume of HEMA particles ($5 \times 10^8$/ml).

The suspension was incubated for 60 minutes at 37° C. under occasional moderate stirring. The incubation was stopped by centrifugation (150 g for 5 minutes) and the pellet was replaced in suspension.

The macrophages with ingested particles were counted under an optical microscope in smears stained with Accustain (modified Wright stain, Sigma).

The cells surrounding at least six particles were considered as being positive.

The average results are represented graphically in FIG. 2. They show that both A0 and A2 strongly stimulate phagocytosis both in the monocytes and the granulocytes of peritoneal macrophages.

Example 10

Effect of A0 and A2 on a Differential Count in the Blood

By using the same experimental groups as in Example 8, two additional microscope slides were prepared from each experimental sample. After Giemsa staining, the presence of individual types of cells i.e. monocytes, lymphocytes and granulocytes were evaluated for each slide with an optical microscope.

The average results are represented graphically in FIG. 3. They show that both A0 and A2 increase the number of monocytes and granulocytes in the peripheral blood.

Example 11

Effect of A0 and A2 on a Differential Count in the Peritoneal Cells

By using the same experimental groups as in Example 8, two additional microscope slides of each experimental sample were prepared. After Giemsa staining, the presence of individual types of cells i.e. macrophages, lymphocytes and mastocytes were evaluated for each slide with an optical microscope.

The average results are represented graphically in FIG. 4. They show that both A0 and A2 increase the number of monocytes and granulocytes in the peritoneal cavity.

TABLE 1a

NMR $^1$H chemical shifts and multiplicity of the monosaccharides corresponding to the formula:

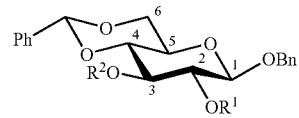

| Compound | | | δ (ppm)/ $J_{Hn-Hn+1}$ | | | | | | |
|---|---|---|---|---|---|---|---|---|---|
| n° | $R^1$ | $R^2$ | H-1/$J_{1,2}$ | H-2/$J_{2,3}$ | H-3/$J_{3,4}$ | H-4/$J_{4,5}$ | H-5/$J_{5,6}$ | H-6/$J_{6,6'}$ | H-6'/$J_{6',5}$ |
| 3 | Lev | NAP | 4.51/8.1 | 5.12/9.1 | 3.76/9.1 | 3.83/9.1 | 3.44/5.1 | 4.39/10.4 | 3.85/10.4 |
| 4 | Lev | H | 4.56/8.0 | 4.99/9.1 | 3.61/9.1 | 3.86/9.1 | 3.42/5.1 | 4.36/10.4 | 3.80/10.4 |
| 10 | H | NAP | 4.50/7.6 | 3.70/8.9 | 3.72/8.9 | 3.76/9.9 | 3.45/5.1 | 4.38/10.2 | 3.84/10.2 |

TABLE 1b

NMR $^{13}$C chemical shifts and multiplicity of the monosaccharides corresponding to the formula:

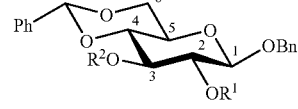

| Compound | | | δ (ppm) | | | | | |
|---|---|---|---|---|---|---|---|---|
| n° | $R^1$ | $R^2$ | C-1 | C-2 | C-3 | C-4 | C-5 | C-6 |
| 3 | Lev | NAP | 100.1 | 73.2 | 78.1 | 81.5 | 66.2 | 68.6 |
| 4 | Lev | H | 99.8 | 74.5 | 72.0 | 80.5 | 66.2 | 68.5 |
| 10 | H | NAP | 102.2 | 74.5 | 80.0 | 81.3 | 66.5 | 68.7 |

TABLE 2a

NMR $^1$H chemical shifts and multiplicity of the monosaccharides corresponding to the formula:

$$\text{Ph}\begin{matrix} \\ \end{matrix}\overset{O}{\underset{R^2O}{\diagdown}}\overset{}{\underset{(b)}{\diagup}}\overset{Ph}{\diagdown}\overset{O}{\underset{OBz}{\diagup}}\overset{O}{\underset{6}{\diagdown}}\overset{O}{\underset{(a)}{\diagup}}\overset{}{\underset{OR^1}{\diagdown}}\text{OBn}$$

| | | | Unit (b) | | | | | | Unit (a) | | | | | |
|---|---|---|---|---|---|---|---|---|---|---|---|---|---|---|
| Compound | | | H-1/ | H-2/ | H-3/ | H-4/ | H-5/ | H-6/ | H-6'/ | H-1/ | H-2/ | H-3/ | H-4/ | H-5/ | H-6/ | H-6'/ |
| n° | $R^1$ | $R^2$ | $J_{1,2}$ | $J_{2,3}$ | $J_{3,4}$ | $J_{4,5}$ | $J_{5,6}$ | $J_{6,6'}$ | $J_{6',5}$ | $J_{1,2}$ | $J_{2,3}$ | $J_{3,4}$ | $J_{4,5}$ | $J_{5,6}$ | $J_{6,6'}$ | $J_{6',5}$ |
| 5 | Lev | NAP | 4.93/ | 5.26/ | 3.85/ | 3.95/ | 3.43/ | 4.13/ | 3.68/ | 4.45/ | 5.06/ | 3.97/ | 3.80/ | 3.43/ | 4.35/ | 3.81/ |
| | | | 7.1 | 7.1 | 9.1 | 9.1 | 4.9 | 10.4 | 10.4 | 7.8 | 8.9 | 8.9 | 8.9 | 4.9 | 10.4 | 10.4 |
| 6 | Lev | H | 5.02/ | 5.14/ | 3.99/ | 3.75/ | 3.46/ | 4.18/ | 3.70/ | 4.49/ | 5.09/ | 4.04/ | 3.78/ | 3.49/ | 4.39/ | 3.82/ |
| | | | 6.8 | 7.1 | 9.3 | 9.3 | 5.1 | 10.6 | 10.6 | 7.5 | 8.4 | 9.1 | 9.1 | 4.8 | 10.6 | 10.6 |
| 11 | H | NAP | 4.95/ | 5.36/ | 3.96/ | 3.75/ | 3.38/ | 4.19/ | 3.62/ | 4.37/ | 3.50/ | 3.88/ | 3.77/ | 3.45/ | 4.32/ | 3.78/ |
| | | | 7.1 | 7.5 | 9.1 | 9.1 | 4.9 | 10.4 | 10.4 | 7.8 | 8.6 | 9.0 | 9.0 | 5.1 | 10.6 | 10.6 |

TABLE 2b

NMR $^{13}$C chemical shifts and multiplicity of the monosaccharides corresponding to the formula:

| Compound | | | Unit (b) | | | | | | Unit (a) | | | | | |
|---|---|---|---|---|---|---|---|---|---|---|---|---|---|---|
| n° | $R^1$ | $R^2$ | C-1 | C-2 | C-3 | C-4 | C-5 | C-6 | C-1 | C-2 | C-3 | C-4 | C-5 | C-6 |
| 5 | Lev | NAP | 100.1 | 74.0 | 78.1 | 80.7 | 65.9 | 68.6 | 99.8 | 72.9 | 77.5 | 79.7 | 66.3 | 68.6 |
| 6 | Lev | H | 100.0 | 75.6 | 72.5 | 80.5 | 65.8 | 68.6 | 99.7 | 72.9 | 77.6 | 79.6 | 66.2 | 68.6 |
| 11 | H | NAP | 101.1 | 74.0 | 77.8 | 81.3 | 66.0 | 68.6 | 102.1 | 74.1 | 79.2 | 81.1 | 66.5 | 68.7 |

TABLE 3a

NMR $^1$H chemical shifts and multiplicity of the monosaccharides corresponding to the formula:

| | | | Unit (c) | | | | | | | Unit (b) | | | | | | |
|---|---|---|---|---|---|---|---|---|---|---|---|---|---|---|---|---|
| Compound | | | H-1/ | H-2/ | H-3/ | H-4/ | H-5/ | H-6/ | H-6'/ | H-1/ | H-2/ | H-3/ | H-4/ | H-5/ | H-6/ | H-6'/ |
| n° | $R^1$ | $R^2$ | $J_{1,2}$ | $J_{2,3}$ | $J_{3,4}$ | $J_{4,5}$ | $J_{5,6}$ | $J_{6,6'}$ | $J_{6',5}$ | $J_{1,2}$ | $J_{2,3}$ | $J_{3,4}$ | $J_{4,5}$ | $J_{5,6}$ | $J_{6,6'}$ | $J_{6',5}$ |
| 7 | Lev | NAP | 5.14/ | 5.39/ | 4.05/ | 3.98- | 3.62- | 4.27/ | 3.76/ | 5.12/ | 5.16- | 4.15- | 3.98- | 3.69- | 4.15- | 3.49/ |
| | | | 7.5 | 8.2 | 8.0 | 3.87/ | 3.52/ | 10.6 | 10.6 | 4.2 | 5.11/ | 4.08/ | 3.87/ | 3.60/ | 4.08/ | 10.4 |
| | | | | | | nd | 5.1 | | | | nd | nd | nd | nd | 10.4 | |
| 8 | Lev | H | 5.14/ | 5.20/ | 3.94/ | 3.62/ | 3.49/ | 4.19/ | 3.66/ | 5.11/ | 5.14- | 4.09- | 4.09- | 3.66- | 4.09- | 3.44/ |
| | | | 7.8 | 7.8 | 7.8 | 7.8 | 4.9 | 10.4 | 10.4 | 4.0 | 5.10/ | 4.03/ | 4.03/ | 3.57/ | 4.03/ | 10.0 |
| | | | | | | | | | | | nd | nd | nd | nd | 10.0 | |
| 12 | H | NAP | 5.12/ | 5.40/ | 3.92/ | 3.95/ | 3.53/ | 4.29/ | 3.79/ | 5.13/ | 5.18/ | 4.02/ | 4.21/ | 3.64/ | 4.09/ | 3.52/ |
| | | | 8.0 | 8.0 | 9.0 | 9.0 | 4.9 | 10.4 | 10.4 | 4.2 | 4.2 | 8.0 | 10.2 | 4.6 | 10.0 | 10.0 |

TABLE 3a-continued

<table>
<tr><th colspan="15">δ (ppm)/multiplicity<br>Unit (a)</th></tr>
<tr><th colspan="3">Compound</th><th>H-1/</th><th>H-2/</th><th>H-3/</th><th>H-4/</th><th>H-5/</th><th>H-6/</th><th>H-6'/</th></tr>
<tr><th>n°</th><th>$R^1$</th><th>$R^2$</th><th>$J_{1,2}$</th><th>$J_{2,3}$</th><th>$J_{3,4}$</th><th>$J_{4,5}$</th><th>$J_{5,6}$</th><th>$J_{6,6'}$</th><th>$J_{6',5}$</th></tr>
<tr><td>7</td><td>Lev</td><td>NAP</td><td>4.33/<br>8.0</td><td>4.60/<br>8.8</td><td>3.92/<br>9.3</td><td>3.02/<br>9.3</td><td>3.31/<br>5.1</td><td>4.27/<br>10.4</td><td>3.58/<br>10.4</td></tr>
<tr><td>8</td><td>Lev</td><td>H</td><td>4.29/<br>7.8</td><td>4.64/<br>9.2</td><td>3.89/<br>9.2</td><td>2.98/<br>9.2</td><td>3.27/<br>4.9</td><td>4.23/<br>10.4</td><td>3.53/<br>10.4</td></tr>
<tr><td>12</td><td>H</td><td>NAP</td><td>4.27/<br>8.0</td><td>2.85/<br>8.0</td><td>3.73/<br>8.8</td><td>3.39-<br>3.32/<br>nd</td><td>3.39-<br>3.32/<br>3.8</td><td>4.32/<br>11.0</td><td>3.75/<br>11.0</td></tr>
</table>

TABLE 3b

NMR $^{13}$C chemical shifts and multiplicity of the monosaccharides corresponding to the formula:

<table>
<tr><th colspan="3">Compound</th><th colspan="6">Unit (c)</th><th colspan="6">Unit (b)</th><th colspan="6">Unit (a)</th></tr>
<tr><th colspan="21">δ (ppm)</th></tr>
<tr><th>n°</th><th>$R^1$</th><th>$R^2$</th><th>C-1</th><th>C-2</th><th>C-3</th><th>C-4</th><th>C-5</th><th>C-6</th><th>C-1</th><th>C-2</th><th>C-3</th><th>C-4</th><th>C-5</th><th>C-6</th><th>C-1</th><th>C-2</th><th>C-3</th><th>C-4</th><th>C-5</th><th>C-6</th></tr>
<tr><td>7</td><td>Lev</td><td>NAP</td><td>98.0</td><td>73.2</td><td>76.1</td><td>81.4</td><td>66.1</td><td>68.7</td><td>97.3</td><td>72.2</td><td>77.6</td><td>78.1</td><td>65.1</td><td>68.7</td><td>99.6</td><td>73.8</td><td>73.5</td><td>78.7</td><td>66.2</td><td>68.5</td></tr>
<tr><td>8</td><td>Lev</td><td>H</td><td>97.8</td><td>74.6</td><td>72.4</td><td>80.8</td><td>66.0</td><td>68.6</td><td>97.4</td><td>72.3</td><td>76.2</td><td>78.7</td><td>65.1</td><td>68.7</td><td>99.6</td><td>73.7</td><td>73.7</td><td>77.6</td><td>66.2</td><td>68.5</td></tr>
<tr><td>12</td><td>H</td><td>NAP</td><td>98.6</td><td>73.3</td><td>78.2</td><td>81.3</td><td>66.1</td><td>68.6</td><td>99.6</td><td>73.5</td><td>77.9</td><td>77.6</td><td>65.1</td><td>68.7</td><td>102.0</td><td>74.7</td><td>76.7</td><td>78.8</td><td>66.6</td><td>68.6</td></tr>
</table>

TABLE 3'a

NMR $^1$H chemical shifts and multiplicity of the monosaccharides corresponding to the formula:

<table>
<tr><th colspan="2"></th><th colspan="14">δ (ppm)/multiplicity</th></tr>
<tr><th colspan="2"></th><th colspan="7">Unit (c)</th><th colspan="7">Unit (b)</th></tr>
<tr><th colspan="2">Compound</th><th>H-1/</th><th>H-2/</th><th>H-3/</th><th>H-4/</th><th>H-5/</th><th>H-6/</th><th>H-6'/</th><th>H-1/</th><th>H-2/</th><th>H-3/</th><th>H-4/</th><th>H-5/</th><th>H-6/</th><th>H-6'/</th></tr>
<tr><th>n°</th><th>$R^1$</th><th>$J_{1,2}$</th><th>$J_{2,3}$</th><th>$J_{3,4}$</th><th>$J_{4,5}$</th><th>$J_{5,6}$</th><th>$J_{6,6'}$</th><th>$J_{6',5}$</th><th>$J_{1,2}$</th><th>$J_{2,3}$</th><th>$J_{3,4}$</th><th>$J_{4,5}$</th><th>$J_{5,6}$</th><th>$J_{6,6'}$</th><th>$J_{6',5}$</th></tr>
<tr><td>18</td><td>Bz</td><td>4.97/<br>7.5</td><td>5.34/<br>7.5</td><td>4.11/<br>9.3</td><td>3.94/<br>9.3</td><td>3.48/<br>4.8</td><td>4.24/<br>10.4</td><td>3.74/<br>10.4</td><td>4.84/<br>6.2</td><td>5.26/<br>6.2</td><td>3.82/<br>9.5</td><td>4.05/<br>nd</td><td>3.55/<br>4.6</td><td>4.18/<br>10.2/</td><td>3.74/<br>10.2</td></tr>
<tr><td>19</td><td>H</td><td>4.57/<br>7.7</td><td>3.79-<br>3.68/<br>9.5</td><td>3.83/<br>9.5</td><td>3.66/<br>9.5</td><td>3.38/<br>4.8</td><td>4.30/<br>10.4</td><td>3.75/<br>10.4</td><td>4.57/<br>5.1</td><td>3.79-<br>3.68/<br>nd</td><td>3.79-<br>3.68/<br>m</td><td>3.79-<br>3.68/<br>m</td><td>3.38/<br>4.8</td><td>4.30/<br>10.4</td><td>3.76/<br>10.4</td></tr>
</table>

<table>
<tr><th colspan="2">Compound</th><th colspan="7">δ (ppm)/multiplicity<br>Unit (a)</th></tr>
<tr><th>n°</th><th>$R^1$</th><th>H-1/$J_{1,2}$</th><th>H-2/$J_{2,3}$</th><th>H-3/$J_{3,4}$</th><th>H-4/$J_{4,5}$</th><th>H-5/$J_{5,6}$</th><th>H-6/$J_{6,6'}$</th><th>H-6'/$J_{6',5}$</th></tr>
<tr><td>18</td><td>Bz</td><td>4.35/0.7</td><td>3.82/10.2</td><td>3.70/9.3</td><td>3.94/9.3</td><td>3.25/4.8</td><td>4.32/10.4</td><td>3.76/10.4t</td></tr>
<tr><td>92</td><td>H</td><td>4.59/<1.0</td><td>4.19/2.7</td><td>3.92/9.5</td><td>4.12/9.5</td><td>3.45/5.1</td><td>4.37/10.6</td><td>3.92/10.6</td></tr>
</table>

TABLE 3'b

NMR $^{13}C$ chemical shifts and multiplicity of the monosaccharides corresponding to the formula:

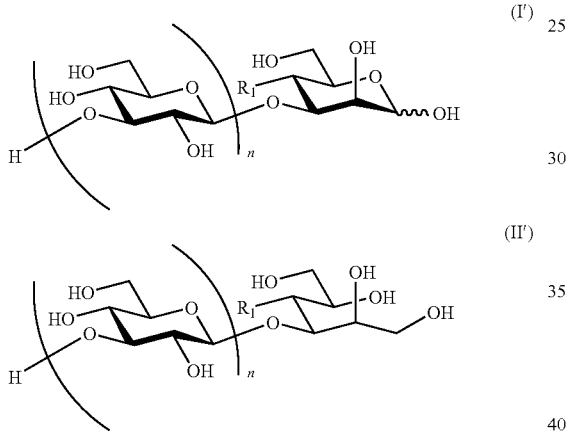

| Compound | | δ (ppm) | | | | | | | | | | | | | | | | | |
|---|---|---|---|---|---|---|---|---|---|---|---|---|---|---|---|---|---|---|---|
| | | Unit (c) | | | | | | Unit (b) | | | | | | Unit (a) | | | | | |
| n° | $R^1$ | C-1 | C-2 | C-3 | C-4 | C-5 | C-6 | C-1 | C-2 | C-3 | C-4 | C-5 | C-6 | C-1 | C-2 | C-3 | C-4 | C-5 | C-6 |
| 18 | Bz | 100.1 | 73.5 | 77.8 | 80.9 | 66.0 | 68.6 | 98.8 | 74.0 | 78.0 | 78.3 | 66.1 | 68.6 | 98.3 | 68.9 | 77.0 | 76.5 | 67.0 | 68.4 |
| 19 | H | 105.7 | 73.0 | 83.6 | 78.6 | 66.9 | 68.3 | 101.3 | 75.1 | 79.9 | 80.8 | 66.7 | 68.5 | 98.1 | 69.4 | 76.9 | 76.3 | 67.1 | 68.4 |

The invention claimed is:

1. A compound of general formula (I') or of general formula (II'):

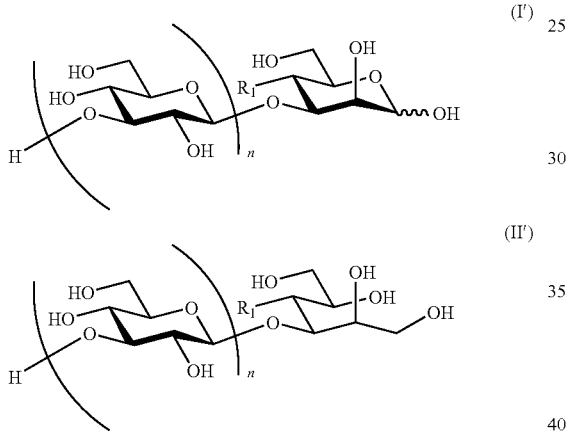

in which $R_1$ represents H or OH and n is an integer from 2 to 10.

2. Compound according to claim 1, wherein said compound is selected from β-D-glucopyranosyl-(1→3)-β-D-glucopyranosyl-(1→3)-(α,β)-D-mannopyranose;

β-D-glucopyranosyl-(1→3)-β-D-glucopyranosyl-(1→3)-β-D-glucopyranosyl-(1→3)-β-D-glucopyranosyl-(1→3)-β-D-glucopyranosyl-(1→3)-β-D-mannopyranose;

β-D-glucopyranosyl-(1→3)-β-D-glucopyranosyl-(1→3)-4-deoxy-(α,β)-D-deoxy-mannopyranose;

β-D-glucopyranosyl-(1→3)-β-D-glucopyranosyl-(1→3)-mannitol;

β-D-glucopyranosyl-(1→3)-β-D-glucopyranosyl-(1→3)-4-deoxy-mannitol;

β-D-glucopyranosyl-(1→3)-β-D-glucopyranosyl-(1-3)-β-D-glucopyranosyl-(1→3)-β-D-glucopyranosyl-(1→3)-β-D-glucopyranosyl-(1→3)-mannitol;

β-D-glucopyranosyl-(1→3)-β-D-glucopyranosyl-(1→3)-β-D-glucopyranosyl-(1→3)-β-D-glucopyranosyl-(1→3)-β-D-glucopyranosyl-(1→3)-4-deoxy-(α,β)-D-mannopyranose; and β-D-glucopyranosyl-(1→3)-β-D-glucopyranosyl-(1→3)-β-D-glucopyranosyl-(1→3)-β-D-glucopyranosyl-(1→3)-β-D-glucopyranosyl-(1→3)-4-deoxy-mannitol.

3. Method for the preparation of compounds according to claim 1, comprising a reaction between a glycosyl donor of formula (D) below and a glycosyl acceptor of formula (A) below:

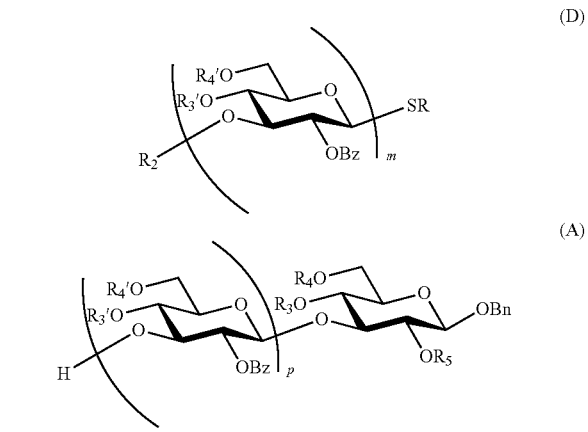

in which m is an integer from 1 to 9;

p is an integer from 0 to 9;

R represents alkyl or aryl;

$R_2$ represents allyl, methylnaphthyl, benzyl, paramethoxybenzyl, halogenoacetyl;

$R_3$ and $R_4$, on the one hand, and $R_3'$ and $R_4'$, on the other hand, together form an ethylidyl, isopropylidyl, hexafluoroisopropylidyl, cyclopentylidyl, cyclohexylidyl, cycloheptylidyl, butylidyl, 1-tertiobutylethylidyl, benzylidyl, methoxybenzylidyl, 1-phenylbenzylidyl radical or $R_3$, $R_4$, $R_3'$ and $R_4'$ represent each independently of each other a benzyl, chlorobenzyl, nitrobenzyl, allyl, triarylmethyl, trialkylsilyl, ester;

$R_5$ represents H, a levulinoyl, acetyl, chloroacetyl, fluorenylmethyloxycarbonyl, trialkylsilyl group, provided that none of $R_3$, $R_4$, $R_3'$, $R_4'$ is identical to $R_5$.

4. Method according to claim 3, wherein the compound of formula (A) is

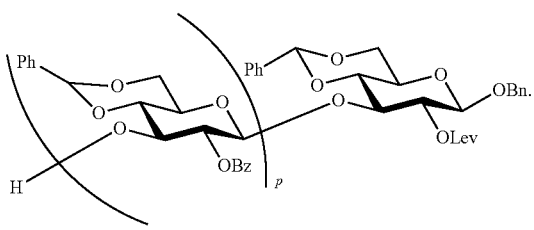

5. Method according to claim 3, wherein the compound of formula (D) is

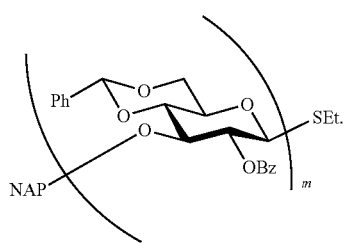

6. Method for the preparation of compounds according to claim 1, comprising a stage of epimerization in position 2 of the terminal entity.

7. Medicaments comprising the compound according to claim 1.

8. Compound as defined in claim 1 for the implementation of a method for the treatment of a disease chosen from the group including tumour, cancer, viral disease, bacterial disease, fungal disease, disease of the immune system, autoimmune disease or disease linked to a deficiency in immunostimulation, in warm-blooded animals and human beings.

9. Compound according to claim 1 wherein n is an integer equal to 2, 3 or 4.

10. Method according to claim 3 wherein m is an integer equal to 2, 3 or 4.

11. Method according to claim 3 wherein p is an integer equal to 2, 3 or 4.

12. Method according to claim 3 wherein R represents ethyl, methyl, propyl, butyl, phenyl or tolyl.

13. Method according to claim 3 wherein the halogenoacetyl group of $R_2$ is selected from chloroacetyl, bromoacetyl and iodoacetyl.

14. Method according to claim 3 wherein the trialkylsilyl group of $R_3$, $R_4$, $R_3'$, $R_4'$ and $R_5$ is selected from triethylsilyl, tri-iso-propylsilyl and tertiobutyldimethylsilyl.

15. Method according to claim 3 wherein the ester group of $R_3$, $R_4$, $R_3'$ and $R_4'$ is selected from acetyl, chloroacetyl, benzoyl, pivaloyl.

16. Method according to claim 3 wherein $R_5$ represents a levulinoyl group.

\* \* \* \* \*